US009000192B2

(12) United States Patent
Yamada et al.

(10) Patent No.: US 9,000,192 B2
(45) Date of Patent: Apr. 7, 2015

(54) CATALYST FOR ASYMMETRIC HYDROGENATION AND METHOD FOR MANUFACTURING OPTICALLY ACTIVE CARBONYL COMPOUND USING THE SAME

(75) Inventors: Shinya Yamada, Kanagawa (JP); Hironori Maeda, Kanagawa (JP); Yoji Hori, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 13/881,181

(22) PCT Filed: Nov. 29, 2011

(86) PCT No.: PCT/JP2011/078012
§ 371 (c)(1),
(2), (4) Date: Apr. 24, 2013

(87) PCT Pub. No.: WO2012/074128
PCT Pub. Date: Jun. 7, 2012

(65) Prior Publication Data
US 2013/0217895 A1    Aug. 22, 2013

(30) Foreign Application Priority Data

Nov. 29, 2010  (JP) ................................ 2010-265556

(51) Int. Cl.
| | | |
|---|---|---|
| *B01J 31/26* | (2006.01) | |
| *C07B 35/02* | (2006.01) | |
| *B01J 23/38* | (2006.01) | |
| *B01J 23/40* | (2006.01) | |
| *B01J 23/44* | (2006.01) | |
| *B01J 23/46* | (2006.01) | |
| *C07B 53/00* | (2006.01) | |
| *C07C 45/62* | (2006.01) | |
| *C07D 207/12* | (2006.01) | |
| *C07D 317/08* | (2006.01) | |
| *C07D 333/22* | (2006.01) | |
| *B01J 31/02* | (2006.01) | |
| *B01J 31/04* | (2006.01) | |

(52) U.S. Cl.
CPC *B01J 31/26* (2013.01); *B01J 23/38* (2013.01); *B01J 23/40* (2013.01); *B01J 23/44* (2013.01); *B01J 23/46* (2013.01); *C07B 53/00* (2013.01); *C07B 2200/07* (2013.01); *C07C 45/62* (2013.01); *C07D 207/12* (2013.01); *C07D 317/08* (2013.01); *C07D 333/22* (2013.01); *C07B 35/02* (2013.01); *B01J 31/0209* (2013.01); *B01J 31/0237* (2013.01); *B01J 31/0245* (2013.01); *B01J 31/04* (2013.01); *B01J 2231/643* (2013.01)

(58) Field of Classification Search
CPC ............ B01J 23/38; B01J 23/40; B01J 23/44; B01J 23/46; B01J 31/26; C07C 45/62; C07C 47/21; C07D 207/12; C07D 317/08; C07D 333/22; C07B 35/02; C07B 53/00

USPC ............. 549/78, 446; 558/423; 502/167; 568/350
See application file for complete search history.

(56) References Cited

U.S. PATENT DOCUMENTS

| | | | |
|---|---|---|---|
| 4,237,072 | A | 12/1980 | Aviron-Violet et al. |
| 4,879,389 | A | 11/1989 | Achiwa |
| 7,534,921 | B2 | 5/2009 | Jakel et al. |
| 2001/0031858 | A1 | 10/2001 | Breipohl et al. |
| 2004/0225109 | A1 | 11/2004 | Breipohl et al. |
| 2006/0161024 | A1 | 7/2006 | MacMillan et al. |
| 2008/0269528 | A1 | 10/2008 | Jakel et al. |
| 2010/0324338 | A1 | 12/2010 | Maeda et al. |

FOREIGN PATENT DOCUMENTS

| | | |
|---|---|---|
| JP | 54-14911 A | 2/1979 |
| JP | 64-19085 A | 1/1989 |
| JP | 2003-523364 A | 8/2003 |
| JP | 2008-515843 A | 5/2008 |

(Continued)

OTHER PUBLICATIONS

Corma, A., "Heterogenised catalysts on zeolites. Synthesis of new chiral Rh (I) complexes with (2S, 4R) trans-4-RCOO-2-(t-butylaminocarbonyl) pyrrolidines and (2S, 4S)-cis-4-RCONH-2-(t-butylaminocarbonyl) pyrrolidines . . . " Journal of Organometallic Chemistrty, 544(2), 147-156.*

Corma, A., "Heterogenised catalysts on zeolites. Synthesis of new chiral Rh (I) complexes with (2S, 4R) trans-4-RCOO-2-(t-butylaminocarbonyl) pyrrolidines and (2S, 4S)-cis-4-RCONH-2-(t-butylaminocarbonyl) pyrrolidines . . . " Journal of Organometallic Chemistry, 1997, 544(2), 147-156.*

International Search Report (PCT/ISA/210), dated Mar. 6, 2012, issued by the International Searching Authority in counterpart International Patent Application No. PCT/JP2011/078012.

(Continued)

*Primary Examiner* — Noble Jarrell
*Assistant Examiner* — John Mauro
(74) *Attorney, Agent, or Firm* — Sughrue Mion, PLLC

(57) ABSTRACT

The present invention provides a catalyst used for manufacturing an optically active carbonyl compound by selective asymmetric hydrogenation of an α, β-unsaturated carbonyl compound, which is insoluble in a reaction mixture, and a method for manufacturing the corresponding optically active carbonyl compound. Particularly, the invention provides a catalyst for obtaining an optically active citronellal useful as a flavor or fragrance, by selective asymmetric hydrogenation of citral, geranial or neral. The invention relates to a catalyst for asymmetric hydrogenation of an α, β-unsaturated carbonyl compound, which comprises: a powder of at least one metal selected from metals belonging to Group 8 to Group 10 of the Periodic Table, or a metal-supported substance in which the at least one metal is supported on a support; an optically active cyclic nitrogen-containing compound; and an acid, and also relates to a method for manufacturing an optically active carbonyl compound using the same.

6 Claims, No Drawings

(56) References Cited

FOREIGN PATENT DOCUMENTS

WO 2010/140636 A1 12/2010
WO 2011/108672 A2 9/2011

OTHER PUBLICATIONS

Written Opinion (PCT/ISA/237), dated Mar. 6, 2012, issued by the International Searching Authority in counterpart International Patent Application No. PCT/JP2011/078012.

Farkas, G., et al., "New chiral auxiliaries in enantioselective heterogeneous catalytic hydrogenations: (−) and (=) -dihydro-apovincaminic acid. Comparison with (−) -dihydro-apovincaminic acid ethyl ester. III," Journal of Molecular Catalysis A: Chemical 138, 1999, pp. 123-127.

Farkas, G., et al., "Enantioselective hydrogenation of isophorone over Pd catalysts in the presence of (−) -dihydroapovincaminic acid ethyl ester The effect of reduction method of Pd Blacks on the enantiomeric excess," Journal of Molecular Catalysis A: Chemical 170, 2001, pp. 101-107.

Fogassy, Gabriella, et al., "Enantioselective hydrogenation of exocyclic alpha, beta-unsaturated ketones Part II. Hydrogenation in the presence of (S)-proline," Journal of Molecular Catalysis A: Chemical 179, 2002, pp. 101-106.

Sipos, E., et al., "Enantioselective hydrogenation of isophorene with titania supported Pd catalysts modified by (−) -dihydroapovincaminic acid ethyl ester effect of the support of the reduction method," Journal of Molecular Catalysis A: Chemical 179, 2002, pp. 107-112.

Fogassy, Gabriella, et al., "Enantioselective hydrogenation of exocyclic alpha, beta-unsaturated ketones Part III. Hydrogenation with Pd in the presence of cinchonidine," Journal of Molecular Catalysis A: Chemical 192, 2003, pp. 189-194.

Ouellet, Stephane, et al., "Enantioselective Organocatalytic Transfer Hydrogenation Reactions using Hantzsch Esters," American Chemical Society, Accounts of Chemical Research, vol. 40, No. 12, 2007, pp. 1327-1339.

Doyaguez, Elisa, et al., "Asymmetric Aldol Reaction Catalyzed by a Heterogenized Proline on a Mesoporous Support. The Role of the Nature of Solvents," American Chemical Society, Journal of Chemical Society, vol. 72, No. 24, Oct. 24, 2007, pp. 9353-9356.

* cited by examiner

CATALYST FOR ASYMMETRIC HYDROGENATION AND METHOD FOR MANUFACTURING OPTICALLY ACTIVE CARBONYL COMPOUND USING THE SAME

TECHNICAL FIELD

The present invention relates to a catalyst for asymmetric hydrogenation, and a method for producing an optically active carbonyl compound, namely an optically active aldehyde or an optically active ketone, by conducting selective asymmetric hydrogenation of carbon-carbon double bond of an $\alpha,\beta$-unsaturated carbonyl compound using the catalyst for asymmetric hydrogenation.

BACKGROUND ART

Conventionally, there has been made attempts for conducting asymmetric hydrogenation of carbon-carbon double bond of $\alpha,\beta$-unsaturated aldehyde using hydrogen gas, and there is known methods for conducting asymmetric hydrogenation of neral or geranial for the purpose of obtaining optically active citronellal which is particularly important as a flavor or fragrance (Patent Literatures 1 and 2). Since these methods are methods for hydrogenating carbon-carbon double bond with hydrogen gas using a small amount of a homogeneous catalyst, auxiliaries are not required so that a large amount of waste is not generated.

There has been reported asymmetric hydrogenation of carbon-carbon double bond of $\alpha,\beta$-unsaturated ketone using a combination of Pd black, Pd/C or Pd/TiO$_2$ and (−)-dihydroapovincamic acid ethyl ester, proline or cinchonidine (Non-Patent Literatures 1 to 5).

In addition, there has been reported hydrogen transfer type asymmetric hydrogenation reaction of an $\alpha,\beta$-unsaturated compound using an organic asymmetric catalyst and Hantzsch ester (Patent Literature 3 and Non-Patent Literature 6).

CITATION LIST

Patent Literature

Patent Literature 1: JP-A-54-14911
Patent Literature 2: JP-T-2008-515843 (the term "JP-T" as used herein means a published Japanese translation of a PCT patent application)
Patent Literature 3: U.S. Patent Publication No. 2006/0161024

Non-Patent Literatures

Non-Patent Literature 1: Journal of Molecular Catalysis A: Chemical 1999, 138, 123-127
Non-Patent Literature 2: Journal of Molecular Catalysis A: Chemical 2001, 170, 101-107
Non-Patent Literature 3: Journal of Molecular Catalysis A: Chemical 2002, 179, 101-106
Non-Patent Literature 4: Journal of Molecular Catalysis A: Chemical 2002, 179, 107-112
Non-Patent Literature 5: Journal of Molecular Catalysis A: Chemical 2003, 192, 189-194
Non-Patent Literature 6: Acc. Chem. Res. 2007, 40, 1327-1339

SUMMARY OF INVENTION

Technical Problem

However, the catalyst used by the methods of Patent Literatures 1 and 2 is a homogeneous catalyst which uses expensive rhodium metals and the like, and it is difficult to recover the catalyst because it dissolves in the reaction solution.

In the methods of Non-Patent Literatures 1 to 5, there are examples using only isophorone and a special exocyclic ketone, and the catalyst system of the invention is not used.

The methods of using organic catalyst described in Non-Patent Literature 6 and Patent Literature 3 are economically disadvantageous as a method for producing an optically active aldehyde or an optically active ketone, because a catalyst quantity of about 20% by mol based on the raw material unsaturated aldehyde or unsaturated ketone is required and the Hantzsch ester as the substrate of hydrogenation is required in an amount of equal to or larger than the raw material unsaturated aldehyde or unsaturated ketone.

Accordingly, concern has been directed toward the development of a method for easily recovering a catalyst by the use of heterogeneous catalyst such as a solid catalyst which does not dissolve in the reaction solution.

In addition, an asymmetric hydrogenation reaction of an $\alpha,\beta$-unsaturated aldehyde using heterogeneous catalyst such as a solid catalyst has not been known.

An object of the invention relates to a method for conducting asymmetric hydrogenation of carbon-carbon double bond of an $\alpha,\beta$-unsaturated carbonyl compound using, as a catalyst for asymmetric hydrogenation, a heterogeneous catalyst which can be easily separated from the reaction solution and thereby obtaining corresponding optically active aldehyde or optically active ketone. Particularly, it relates to a method for obtaining optically active citronellal by hydrogenating citral, geranial or neral by asymmetric hydrogenation reaction.

Solution to Problem

The present inventors have conducted intensive studies with the aim of solving the above-mentioned problems and found as a result that a corresponding optically active aldehyde or optically active ketone can be obtained by conducting asymmetric hydrogenation of an $\alpha,\beta$-unsaturated carbonyl compound using a specific metal powder or metal-supported substance, a specific optically active cyclic nitrogen-containing compound and an acid, thereby resulting in the accomplishment of the invention.

In addition, after completion of the reaction, the optically active cyclic nitrogen-containing compound and metal powder or metal-supported substance can be easily recovered from the reaction system and reused again as the catalyst for asymmetric hydrogenation.

That is, the invention includes the following respective embodiments.

[1] A catalyst for asymmetric hydrogenation of an $\alpha,\beta$-unsaturated carbonyl compound, which comprises:
a powder of at least one metal selected from metals belonging to Group 8 to Group 10 of the Periodic Table, or a metal-supported substance in which at least one metal selected from metals belonging to Group 8 to Group 10 of the Periodic Table is supported on a support;
an optically active cyclic nitrogen-containing compound represented by the following general formula (1):

[Chem. 1]

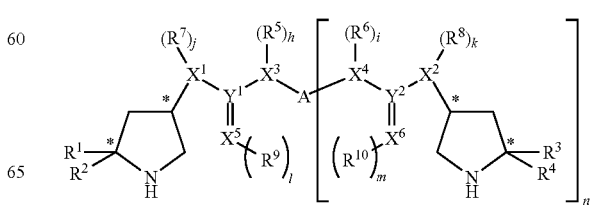

(1)

wherein $R^1$, $R^2$, $R^3$, $R^4$, $R^5$, $R^6$, $R^7$, $R^8$, $R^9$ and $R^{10}$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amido group which may have a substituent group, a siloxy group which may have a substituent group, an aromatic heterocyclic group which may have a substituent group or an aliphatic heterocyclic group which may have a substituent group, wherein $R^1$ and $R^2$ are different from each other, and $R^3$ and $R^4$ are different from each other, h, i, j, k, l and m represents an integer of 0 or 1, n represents an integer of 0 to 3, and * represents an asymmetric carbon atom, A represents, when n=0, a hydrogen atom, a hetero atom which may have a substituent group, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amido group which may have a substituent group, an aromatic heterocyclic group which may have a substituent group, an aliphatic heterocyclic group which may have a substituent group, an oligomer chain, or a polymer chain, and A represents, when n=1 to 3, a hetero atom which may have a substituent group, an alkylene group which may have a substituent group, an alkylene group which includes an arylene group and may have a substituent group, an alkylene group which includes a cycloalkylene group and may have a substituent group, an alkylene group which includes a hetero atom and may have a substituent group, a divalent aliphatic hydrocarbon cyclic group which may have a substituent group, a divalent aliphatic heterocyclic group which may have a substituent group, a divalent aromatic hydrocarbon cyclic group which may have a substituent group, a divalent aromatic heterocyclic group which may have a substituent group, an oligomer chain, or a polymer chain, $R^5$ and $R^6$, $R^5$ and A, or $R^6$ and A may form a ring, $X^1$, $X^2$, $X^3$, $X^4$, $X^5$ and $X^6$ each independently represent an oxygen atom, a nitrogen atom, a phosphorus atom or a sulfur atom, and $Y^1$ and $Y^2$ each independently represent a carbon atom, a silicon atom or a sulfur atom; and an acid.

[2] The catalyst for asymmetric hydrogenation according to [1], wherein the metal is selected from the group consisting of nickel, ruthenium, rhodium, iridium, palladium and platinum.

[3] A method for manufacturing an optically active carbonyl compound represented by the following general formula (3):

[Chem. 2]

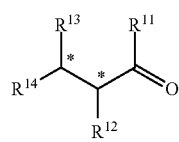

(3)

wherein $R^{11}$, $R^{12}$, $R^{13}$ and $R^{14}$ are the same as defined in the following formula (2), and two * mean that at least one * represents an asymmetric carbon atom, wherein the method comprises conducting asymmetric hydrogenation of an α, β-unsaturated carbonyl compound represented by the following general formula (2) by using the catalyst for asymmetric hydrogenation according to [1] or [2]:

[Chem. 3]

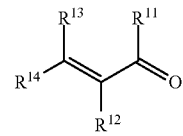

(2)

wherein $R^{11}$, $R^{12}$, $R^{13}$ and $R^{14}$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, an alkoxycarbonyl group which may have a substituent group, or an aralkyloxy group which may have a substituent group; $R^{11}$ and $R^{12}$, $R^{11}$ and $R^{13}$, $R^{11}$ and $R^{14}$, $R^{12}$ and $R^{14}$, or $R^{13}$ and $R^{14}$ may form a ring; when a ring is not formed by $R^{11}$ and $R^{12}$ or $R^{11}$ and $R^{13}$, and $R^{12}$ does not represent a hydrogen atom, $R^{13}$ and $R^{14}$ may be the same or different from each other; and when a ring is not formed by $R^{11}$ and $R^{12}$ or $R^{11}$ and $R^{13}$, and $R^{12}$ represents a hydrogen atom, $R^{13}$ and $R^{14}$ do not represent a hydrogen atom and are different from each other.

[4] The method according to [3], wherein the α, β-unsaturated carbonyl compound is geranial, neral or citral.

[5] The method according to [3], wherein the α, β-unsaturated carbonyl compound is an α, β-unsaturated ketones having from 5 to 18 carbon atoms.

Advantageous Effects of Invention

As described in the foregoing, as the catalyst of the asymmetric hydrogenation reaction, the invention uses an optically active cyclic nitrogen-containing compound and an acid as additives which contribute to the enantio-selectivity, together with a metal powder or metal-supported substance.

The asymmetric hydrogenation catalyst of the invention does not require a reaction step for preparing a catalyst like the conventional asymmetric hydrogenation catalyst. In the invention, asymmetric hydrogenation is carried out by simply mixing a raw material compound, an optically active cyclic nitrogen-containing compound, a metal powder or metal-supported substance and an acid. Thus, the operation is convenient and the metal powder or metal-supported substance and optically active cyclic nitrogen-containing compound can be recovered and reused, which is industrially advantageous.

In addition, in the case of using, as a substrate, each of a Z-configuration or E-configuration compound regarding the double bond at the α-position and β-position of the α,β-unsaturated carbonyl compound, when using the catalyst of the invention, the configuration of the formed optically active carbonyl compound depends on the configuration of the optically active cyclic nitrogen-containing compound to be used. Thus, according to the invention, even when a mixture (i.e., citral) of the Z-configuration compound and E-configuration compound is used as the substrate, an optically active carbonyl compound having the same configuration can be produced.

DESCRIPTION OF EMBODIMENTS

The following describes the invention in detail.

Herein, "% by weight" and "part by weight" have the same meanings as "% by mass" and "part by mass", respectively.
<Catalyst>

According to the invention, an α,β-unsaturated carbonyl compound is used as the substrate, and an optically active aldehyde or an optically active ketone, which is an optically active carbonyl compound, is produced by subjecting this to asymmetric hydrogenation using the catalyst of the invention. First, the catalyst of the invention is described.
(Metal)

The catalyst of the invention is a catalyst for asymmetric hydrogenation of an α,β-unsaturated carbonyl compound, which comprises a powder of at least one metal selected from metals belonging to Group 8 to Group 10 of the Periodic Table, or a metal-supported substance in which at least one metal selected from metals belonging to Group 8 to Group 10 of the Periodic Table is supported on a support, an optically active cyclic nitrogen-containing compound represented by the general formula (1) and an acid.

The following describes the powder of at least one metal selected from metals belonging to Group 8 to Group 10 of the Periodic Table and the metal-supported substance in which at least one metal selected from metals belonging to Group 8 to Group 10 of the Periodic Table is supported on a support.

As the metals belonging to Group 8 to Group 10 of the Periodic Table, Ni (nickel), Ru (ruthenium), Rh (rhodium), Ir (iridium), Pd (palladium)) and Pt (platinum) are desirable, and Pd is particularly desirable.

As the metal powder, Pd black, Pt black, and Raney nickel can be mentioned.

As the metal-supported substance, those in which the above-mentioned metals are supported on a support are used, and those in which these metals are supported on supports such as carbon, silica, alumina, silica-alumina, zeolite, a metal oxide, a metal halide, a metal sulfide, a metal sulfonate, a metal nitrate, a metal carbonate or a metal phosphate are suitably used. Among these, a substance in which palladium or platinum is supported on a support is desirable.

As illustrative metal-supported substance, Ru/C, Rh/C, Pd/C, Ir/C, Pt/C, Pd/C(en)(palladium/carbon-ethylenediamine complex), Pd/Fib(palladium-fibroin), Pd/PEI(palladium-polyethyleneimine), Pd/Al$_2$O$_3$, Pd/SiO$_2$, Pd/TiO$_2$, Pd/ZrO$_2$, Pd/CeO$_2$, Pd/ZnO, Pd/CdO, Pd/TiO$_2$, Pd/SnO$_2$, Pd/PbO, Pd/As$_2$O$_3$, Pd/Bi$_2$O$_3$, Pd/Sb$_2$O$_5$, Pd/V$_2$O$_5$, Pd/Nb$_2$O$_5$, Pd/Cr$_2$O$_3$, Pd/MoO$_3$, Pd/WO$_3$, Pd/BeO, Pd/MgO, Pd/CaO, Pd/SrO, Pd/BaO, Pd/Y$_2$O$_3$, Pd/La$_2$O$_3$, Pd/Na$_2$O, Pd/K$_2$O, Pd/CdS, Pd/ZnS, Pd/MgSO$_4$, Pd/CaSO$_4$, Pd/SrSO$_4$, Pd/BaSO$_4$, Pd/CuSO$_4$, Pd/ZnSO$_4$, Pd/CdSO$_4$, Pd/Al$_2$(SO$_4$)$_3$, Pd/FeSO$_4$, Pd/Fe$_2$(SO$_4$)$_3$, Pd/CoSO$_4$, Pd/NiSO$_4$, Pd/Cr$_2$(SO$_4$)$_3$, Pd/KHSO$_4$, Pd/K$_2$SO$_4$, Pd/(NH$_4$)$_2$SO$_4$, Pd/Zn(NO$_3$)$_2$, Pd/Ca(NO$_3$)$_2$, Pd/Bi(NO$_3$)$_3$, Pd/Fe(NO$_3$)$_3$, Pd/Na$_2$CO$_3$, Pd/K$_2$CO$_3$, Pd/KHCO$_3$, Pd/KNaCO$_3$, Pd/CaCO$_3$, Pd/SrCO$_3$, Pd/BaCO$_3$, Pd/(NH$_4$)$_2$CO$_3$, Pd/Na$_2$WO$_4$.2H$_2$O, Pd/KCN, Pd/BPO$_4$, Pd/AlPO$_4$, Pd/CrPO$_4$, Pd/FePO$_4$, Pd/Cu$_3$(PO$_4$)$_2$, Pd/Zn$_3$(PO$_4$)$_2$, Pd/Mg$_3$(PO$_4$)$_2$, Pd/Ti$_3$(PO$_4$)$_4$, Pd/Zr$_3$(PO$_4$)$_4$, Pd/Ni$_3$(PO$_4$)$_2$, Pd/AgCl, Pd/CuCl, Pd/CaCl$_2$, Pd/AlCl$_3$, Pd/TiCl$_3$, Pd/SnCl$_2$, Pd/CaF$_2$, Pd/BaF$_2$, Pd/AgClO$_4$, Pd/Mg(ClO$_4$)$_2$, Pd/Zeolite, Pd/SiO$_2$—Al$_2$O$_3$, Pd/SiO$_2$—TiO$_3$, Pd/SiO$_2$—ZrO$_2$, Pd/SiO$_2$—BeO, Pd/SiO$_2$—MgO, Pd/SiO$_2$—CaO, Pd/SiO$_2$—SrO, Pd/SiO$_2$—BaO, Pd/SiO$_2$—ZnO, Pd/SiO$_2$—TiO$_2$, Pd/SiO$_2$—ZrO$_2$, Pd/SiO$_2$—Ga$_2$O$_3$, Pd/SiO$_2$—Y$_2$O$_3$, Pd/SiO$_2$—La$_2$O$_3$, Pd/SiO$_2$—MoO$_3$, Pd/SiO$_2$—WO$_3$, Pd/SiO$_2$—V$_2$O$_5$, Pd/SiO$_2$—ThO$_2$, Pd/Al$_2$O$_3$—MgO, Pd/Al$_2$O$_3$—ZnO, Pd/Al$_2$O$_3$—CdO, Pd/Al$_2$O$_3$—B$_2$O$_3$, Pd/Al$_2$O$_3$—ThO$_2$, Pd/Al$_2$O$_3$—TiO$_2$, Pd/Al$_2$O$_3$—ZrO$_2$, Pd/Al$_2$O$_3$—V$_2$O$_5$, Pd/Al$_2$O$_3$—MoO$_3$, Pd/Al$_2$O$_3$—WO$_3$, Pd/Al$_2$O$_3$—Cr$_2$O$_3$, Pd/Al$_2$O$_3$—Mn$_2$O$_3$, Pd/Al$_2$O$_3$—Fe$_2$O$_3$, Pd/Al$_2$O$_3$—Co$_3$O$_4$, Pd/Al$_2$O$_3$—NiO, Pd/TiO$_2$—CuO, Pd/TiO$_2$—MgO, Pd/TiO$_2$—ZnO, Pd/TiO$_2$—CdO, Pd/TiO$_2$—ZrO$_2$, Pd/TiO$_2$—SnO$_2$, Pd/TiO$_2$—Bi$_2$O$_3$, Pd/TiO$_2$—Sb$_2$O$_5$, Pd/TiO$_2$—V$_2$O$_5$, Pd/TiO$_2$—Cr$_2$O$_3$, Pd/TiO$_2$—MoO$_3$, Pd/TiO$_2$—WO$_3$, Pd/TiO$_2$—Mn$_2$O$_3$, Pd/TiO$_2$—Fe$_2$O$_3$, Pd/TiO$_2$—Co$_3$O$_4$, Pd/TiO$_2$—NiO, Pd/ZrO$_2$—CdO, Pd/ZnO—MgO, Pd/ZnO—Fe$_2$O$_3$, Pd/MoO$_3$—CoO—Al$_2$O$_3$, Pd/MoO$_3$—NiO—Al$_2$O$_3$, Pd/TiO$_2$—SiO$_2$—MgO, Pd/MoO$_3$—Al$_2$O$_3$—MgO, Pd/Heteropoly acids, Pt/SiO$_2$, Pt/Al$_2$O$_3$, and Pt/Zeolite, Rh/Al$_2$O$_3$ can be mentioned.

(Optically Active Cyclic Nitrogen-Containing Compound)

Next, the optically active cyclic nitrogen-containing compound which is used as a catalyst component of the invention and represented by the general formula (1) is described.

[Chem. 4]

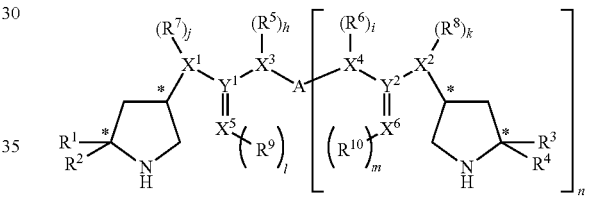

(1)

In the formula (1), $R^1$, $R^2$, $R^3$, $R^4$, $R^5$, $R^6$, $R^7$, $R^8$, $R^9$ and $R^{10}$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amido group which may have a substituent group, a siloxy group which may have a substituent group, an aromatic heterocyclic group which may have a substituent group or an aliphatic heterocyclic group which may have a substituent group, wherein $R^1$ and $R^2$ are different from each other, and $R^3$ and $R^4$ are different from each other.

In the formula (1), h, i, j, k, l and m represents an integer of 0 or 1, n represents an integer of 0 to 3, and * represents an asymmetric carbon atom.

In the formula (1), A represents, when n=0, a hydrogen atom, a hetero atom which may have a substituent group, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amido group which may have a substituent group, an aromatic heterocyclic group which may have a substituent group, an aliphatic heterocyclic group which may have a substituent group, an oligomer chain, or a polymer chain.

Further, A represents, when n=1 to 3, a hetero atom which may have a substituent group, an alkylene group which may have a substituent group, an alkylene group which includes an arylene group and may have a substituent group, an alkylene group which includes a cycloalkylene group and may have a substituent group, an alkylene group which includes a hetero atom and may have a substituent group, a divalent aliphatic hydrocarbon cyclic group which may have a substituent group, a divalent aliphatic heterocyclic group which may have a substituent group, a divalent aromatic hydrocarbon cyclic group which may have a substituent group, a divalent aromatic heterocyclic group which may have a substituent group, an oligomer chain, or a polymer chain.

$R^5$ and $R^6$, $R^5$ and A, or $R^6$ and A may form a ring.

$X^1$, $X^2$, $X^3$, $X^4$, $X^5$ and $X^6$ each independently represent an oxygen atom, a nitrogen atom, a phosphorus atom or a sulfur atom.

$Y^1$ and $Y^2$ each independently represent a carbon atom, a silicon atom or a sulfur atom.

Next, the alkyl group, cycloalkyl group, alkenyl group, aryl group, aralkyl group, alkoxy group, carboxyl group, alkoxycarbonyl group, amido group, siloxy group, aromatic heterocyclic group and aliphatic heterocyclic group, as the groups represented by $R^1$, $R^2$, $R^3$, $R^4$, $R^5$, $R^6$, $R^7$, $R^8$, $R^9$ and $R^{10}$, are described. Each of these groups may have a substituent group.

As the alkyl group, a chain or branched alkyl group having from 1 to 30 carbon atoms, preferably from 1 to 10 carbon atoms, can be mentioned, and illustrative examples thereof include a methyl group, ethyl group, n-propyl group, isopropyl group, n-butyl group, 2-butyl group, isobutyl group, tert-butyl group, n-pentyl group, 2-pentyl group, 3-pentyl group, tert-pentyl group, 2-methylbutyl group, 3-methylbutyl group, 2,2-dimethylpropyl group, 1,2-dimethylpropyl group, n-hexyl group, 2-hexyl group, 3-hexyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, heneicosyl group, and docosyl group.

In addition, these alkyl groups may have a substituent group, and as the substituent group of alkyl groups, examples thereof include an alkenyl group, an alkynyl group, an aryl group, an aliphatic heterocyclic group, an aromatic heterocyclic group, an alkoxy group, a trialkylsiloxy group, an alkylenedioxy group, an aryloxy group, an aralkyloxy group, a heteroaryloxy group, an amino group, a substituted amino group, an alkyl halide group, a cycloalkyl group, a hydroxyl group, and a halogen atom.

The alkenyl group as the substituent group of the alkyl group includes a straight chain or branched alkenyl group having from 2 to 20 carbon atoms, preferably from 2 to 10 carbon atoms, more preferably from 2 to 6 carbon atoms, and illustrative examples thereof include vinyl group, propenyl group, 1-butenyl group, pentenyl group, hexenyl group and the like.

The alkynyl group as the substituent group of the alkyl group includes a straight chain or branched alkynyl group having from 2 to 15 carbon atoms, preferably from 2 to 10 carbon atoms, more preferably from 2 to 6 carbon atoms, and illustrative examples thereof include ethynyl group, 1-propynyl group, 2-propynyl group, 1-butynyl group, 3-butynyl group, pentinyl group, hexynyl group and the like.

As the aryl group as the substituent group of the alkyl group, an aryl group having from 6 to 20 carbon atoms can be mentioned, and illustrative examples thereof include phenyl group, tolyl group, isopropylphenyl group, xylyl group, t-butylphenyl group, adamantylphenyl group, trifluoromethylphenyl group, naphthyl group, anthryl group, phenanthryl group, biphenyl group, 4-(2'-p-tolylpropyl)phenyl group, mesityl group, methoxyphenyl group, dimethoxyphenyl group, 4-(3',4',5',6',7',8',9',10'-heptadecafluorodecyl)phenyl group, fluorophenyl group and the like.

The aliphatic heterocyclic group as the substituent group of the alkyl group includes a group which has 2 to 14 carbon atoms and contains, as heterogeneous atoms, at least one, preferably 1 to 3 hetero atoms such as nitrogen atom, oxygen atom and sulfur atom. Preferable examples thereof include a 5- or 6-membered monocyclic aliphatic heterocyclic group and a polycyclic or condensed ring aliphatic heterocyclic group. As the aliphatic heterocyclic group, illustrative examples thereof include 2-oxo-1-pyrrolidinyl group, piperidino group, piperazinyl group, morpholino group, tetrahydrofuryl group, tetrahydropyranyl group, tetrahydrothienyl group and the like.

The aromatic heterocyclic group as the substituent group of the alkyl group includes a group which has 2 to 15 carbon atoms and contains, as heterogeneous atoms, at least one, preferably 1 to 3 hetero atoms such as nitrogen atom, oxygen atom and sulfur atom. Preferable examples thereof include a 5- or 6-membered monocyclic aromatic heterocyclic group and a polycyclic or condensed ring aromatic heterocyclic group. As the aromatic heterocyclic group, illustrative examples thereof include furyl group, methylfuryl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, benzothiazolyl group and the like.

As the alkoxy group as the substituent group of the alkyl group, a straight chain or branched alkoxy group having from 1 to 8 carbon atoms can be mentioned, and illustrative examples thereof include methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group, cyclopentyloxy group, cyclohexyloxy group and the like.

As the trialkylsiloxy group as the substituent group of the alkyl group, examples thereof include trimethylsiloxy group, triethylsiloxy group, and dimethyl-tert-butylsiloxy group.

As the alkylenedioxy group as the substituent group of the alkyl group, an alkylenedioxy group having from 1 to 3 carbon atoms can be mentioned, and illustrative examples thereof include methylenedioxy group, ethylenedioxy group, propylenedioxy group, isopropylidenedioxy group and the like.

As the aryloxy group as the substituent group of the alkyl group, an aryloxy group having from 6 to 15 carbon atoms can be mentioned, and illustrative examples thereof include phenoxy group, naphthyloxy group, anthryloxy group, tolyloxy group, xylyloxy group, 4-phenylphenoxy group, 3,5-diphenylphenoxy group, 4-mesitylphenoxy group, 3,5-bis(trifluoromethyl)phenoxy group and the like.

As the aralkyloxy group as the substituent group of the alkyl group, an aralkyloxy group having from 7 to 12 carbon atoms can be mentioned, and illustrative examples thereof include benzyloxy group, 2-phenylethoxy group, 1-phenylpropoxy group, 2-phenylpropoxy group, 3-phenylpropoxy group, 1-phenylbutoxy group, 2-phenylbutoxy group, 3-phenylbutoxy group, 4-phenylbutoxy group, 1-phenylpentyloxy group, 2-phenylpentyloxy group, 3-phenylpentyloxy group, 4-phenylpentyloxy group, 5-phenylpentyloxy group, 1-phenylhexyloxy group, 2-phenylhexyloxy group, 3-phenylhexyloxy group, 4-phenylhexyloxy group, 5-phenylhexyloxy group, 6-phenylhexyloxy group and the like.

The heteroaryloxy group as the substituent group of the alkyl group includes a heteroaryloxy group which has 2 to 14 carbon atoms and contains, as heterogeneous atoms, at least one, preferably 1 to 3 hetero atoms such as nitrogen atom, oxygen atom and sulfur atom, and illustrative examples thereof include 2-pyridyloxy group, 2-pyrazyloxy group, 2-pyrimidyloxy group, 2-quinolyloxy group and the like.

As the substituted amino group as the substituent group of the alkyl group, examples thereof include mono- or di-alkylamino groups such as N-methylamino group, N,N-dimethylamino group, N,N-diethylamino group, N,N-diisopropylamino group, N-cyclohexylamino group, pyrrolidyl group, piperidyl group and morpholyl group; mono- or di-arylamino group such as N-phenylamino group, N,N-diphenylamino group, N-naphthylamino group and N-naphthyl-N-phenylamino group; mono- or di-aralkylamino group such as N-benzylamino group and N,N-dibenzylamino group.

As the alkyl halide group as the substituent group of the alkyl group, a perhalogenoalkyl group is desirable, and examples thereof include trifluoromethyl group, pentafluoroethyl group, heptafluoropropyl group, undecafluoropentyl group, heptadecafluorooctyl group, undecafluorocyclohexyl group, dichloromethyl group and the like.

As the cycloalkyl group as the substituent group of the alkyl group, examples thereof include cyclopropyl group, cyclobutyl group, cyclopentyl group, cyclohexyl group, 1-methylcyclohexyl group and the like.

As the halogen atom as the substituent group of the alkyl group, examples thereof include fluorine atom, chlorine atom, bromine atom, and iodine atom.

As the cycloalkyl group, examples thereof include cyclopropyl group, cyclobutyl group, cyclopentyl group, cyclohexyl group, and 1-methylcyclohexyl group.

These cycloalkyl groups may have a substituent group, and as the substituent group, the substituent groups described in the aforementioned description on the substituent group of the alkyl group can be mentioned.

As the alkenyl group, a chain or branched or cyclic alkenyl group having from 2 to 20 carbon atoms, preferably from 2 to 10 carbon atoms, can be mentioned. As illustrative alkenyl groups, examples thereof include vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-cyclopentenyl group, 3-cyclopentenyl group, 1-hexenyl group, 2-hexenyl group, 3-hexenyl group, 4-hexenyl group, 5-hexenyl group, 4-methyl-3-pentenyl group, 4,8-dimethyl-3,7-nonadienyl group, 1-cyclohexenyl group, and 3-cyclohexenyl group.

These alkenyl groups may have a substituent group, and as the substituent group, the groups described in the aforementioned description on the substituent group of the alkyl group can be mentioned.

As the aryl group, an aryl group having from 6 to 20 carbon atoms can be mentioned, and illustrative examples thereof include phenyl group, tolyl group, isopropylphenyl group, xylyl group, t-butylphenyl group, adamantylphenyl group, trifluoromethylphenyl group, naphthyl group, anthryl group, phenanthryl group, biphenyl group, 4-(2'-p-tolylpropyl)phenyl group, mesityl group, methoxyphenyl group, dimethoxyphenyl group, 4-(3',4',5',6',7',8',9',10'-heptadecafluorodecyl)phenyl group, and fluorophenyl group.

These aryl groups may have a substituent group, and as the substituent group, the groups described in the description on the substituent group of the alkyl group can be mentioned.

As the aralkyl group, an aralkyl group having from 7 to 45 carbon atoms, and illustrative examples thereof include benzyl group, tolylmethyl group, xylylmethyl group, mesitylmethyl group, 4-phenylphenylmethyl group, 3-phenylphenylmethyl group, 2-phenylphenylmethyl group, 4-mesitylphenylmethyl group, 1-naphthylmethyl group, 2-naphthylmethyl group, 9-anthrylmethyl group, 9-phenanthrylmethyl group, 3,5-diphenylphenylmethyl group, 2-phenylethyl group, 1-phenylpropyl group, 3-naphthylpropyl group, diphenylmethyl group, ditolylmethyl group, dixylylmethyl group, dimesitylmethyl group, di(4-phenylphenyl)methyl group, di(3-phenylphenyl)methyl group, di(2-phenylphenyl)methyl group, di(4-mesitylphenyl)methyl group, di-1-naphthylmethyl group, di-2-naphthylmethyl group, di-9-anthrylmethyl group, di-9-phenanthrylmethyl group, bis(3,5-diphenylphenyl)methyl group, triphenylmethyl group, tritolylmethyl group, trixylylmethyl group, trimesitylmethyl group, tri(4-phenylphenyl)methyl group, tri(3-phenylphenyl)methyl group, tri(2-phenylphenyl)methyl group, tri(4-mesitylphenyl)methyl group, tri-1-naphthyl methyl group, tri-2-naphthylmethyl group, tri-9-anthrylmethyl group, tri-9-phenanthrylmethyl group, tris(3,5-diphenylphenyl)methyl group, trimethylsiloxyphenylmethyl group, trimethylsiloxydiphenyl methyl group, trimethylsiloxyditolyl methyl group, trimethyl siloxydi(4-t-butylphenyl)methyl group, trimethylsiloxydixylylmethyl group, trimethylsiloxydi(2-phenylphenyl)methyl group, trimethylsiloxydi(3-phenylphenyl)methyl group, trimethylsiloxydi(4-phenylphenyl)methyl group, trimethylsiloxybis(3,5-diphenylphenyl)methyl group, trimethylsiloxydi(4-mesitylphenyl)methyl group, and trimethylsiloxybis(3,5-ditrifluoromethylphenyl)methyl group.

These aralkyl groups may have a substituent group, and as the substituent group, the groups described in the description on the substituent group of the alkyl group can be mentioned.

As the alkoxy group, an alkoxy group having from 1 to 30 carbon atoms, and illustrative examples thereof include methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group, cyclopentyloxy group, cyclohexyloxy group, dicyclopentylmethoxy group, dicyclohexylmethoxy group, tricyclopentyl methoxy group, tricyclohexylmethoxy group, phenylmethoxy group, diphenylmethoxy group, and triphenylmethoxy group.

These alkoxy groups may have a substituent group, and as the substituent group, the groups described in the description on the substituent group of the alkyl group can be mentioned.

As the carboxyl group, a carboxyl group having from 1 to 30 carbon atoms, and illustrative examples thereof include acetoxy group, n-propanoyloxy group, isopropanoyloxy group, n-butanoyloxy group, 2-butanoyloxy group, isobutanoyloxy group, tert-butanoyloxy group, n-pentanoyloxy group, 2-methylbutanoyloxy group, 3-methylbutanoyloxy group, 2,2-dimethylpropanoyloxy group, n-hexanoyloxy group, 2-methylpentanoyloxy group, 3-methylpentanoyloxy group, 4-methylpentanoyloxy group, 5-methylpentanoyloxy group, cyclopentanoyloxy group, cyclohexanoyloxy group, dicyclopentylacetoxy group, dicyclohexylacetoxy group, tricyclopentylacetoxy group, tricyclohexylacetoxy group, phenylacetoxy group, diphenylacetoxy group, triphenylacetoxy group, benzoyloxy group, and naphthoyloxy group.

These carboxyl groups may have a substituent group, and as the substituent group, the groups described in the description on the substituent group of the alkyl group can be mentioned.

As the alkoxycarbonyl group, an alkoxycarbonyl group having from 1 to 30 carbon atoms, and illustrative examples thereof include methoxycarbonyl group, ethoxycarbonyl group, n-propoxycarbonyl group, isopropoxycarbonyl group, n-butoxycarbonyl group, 2-butoxycarbonyl group, isobutoxycarbonyl group, tert-butoxycarbonyl group, n-pentyloxycarbonyl group, 2-methylbutoxycarbonyl group, 3-methylbutoxycarbonyl group, 2,2-dimethylpropoxycarbonyl group, n-hexyloxycarbonyl group, 2-methylpentyloxycarbonyl group, 3-methylpentyloxycarbonyl group, 4-methylpentyloxycarbonyl group, 5-methylpentyloxycarbonyl group, cyclopentyloxycarbonyl group, cyclohexyloxycarbonyl group, dicyclopentylmethoxycarbonyl group, dicyclohexylmethoxycarbonyl group, tricyclopentylmethoxycarbonyl group, tricyclohexylmethoxycarbonyl group, phenylmethoxycarbonyl group, and diphenylmethoxycarbonyl group, triphenylmethoxycarbonyl group.

These alkoxycarbonyl groups may have a substituent group, and as the substituent group, the groups described in the description on the substituent group of the alkyl group can be mentioned.

As the amido group, an amido group having from 1 to 30 carbon atoms, and illustrative examples thereof include acetamido group, n-propionamido group, isopropionamido group, n-butanamido group, 2-butanamido group, isobutanamido group, tert-butanamido group, n-pentanamido group, 2-methylbutanamido group, 3-methylbutanamido group, 2,2-dimethyl propionamido group, n-hexanamido group, 2-methylpentanamido group, 3-methylpentanamido group, 4-methylpentanamido group, 5-methylpentanamido group, cyclopentanamido group, cyclohexanamido group, dicyclopentylacetamido group, dicyclohexylacetamido group, tricyclopentylacetamido group, tricyclohexylacetamido group, phenylacetamido group, diphenylacetamido group, triphenylacetamido group, benzamido group, and naphthalenamido group.

These amido groups may have a substituent group, and as the substituent group, the groups described in the description on the substituent group of the alkyl group can be mentioned.

As the siloxy group, examples thereof include trimethylsiloxy group, triethylsiloxy group, and dimethyl-tert-butylsiloxy group.

These siloxy groups may have a substituent group, and as the substituent group, the groups described in the description on the substituent group of the alkyl group can be mentioned.

The aromatic heterocyclic group includes a group which has from 2 to 15 carbon atoms and contains, as heterogeneous atoms, at least one, preferably from 1 to 3 hetero atoms such as nitrogen atom, oxygen atom and sulfur atom. Preferable examples thereof include a 5- or 6-membered monocyclic aromatic heterocyclic group and a polycyclic or condensed ring aromatic heterocyclic group. As illustrative examples of the aromatic heterocyclic group, examples thereof include furyl group, methylfuryl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, and benzothiazolyl group.

These aromatic heterocyclic groups may have a substituent group, and as the substituent group, the groups described in the description on the substituent group of the alkyl group can be mentioned.

As the aliphatic heterocyclic group, examples thereof include a group which has from 2 to 14 carbon atoms and contains, as heterogeneous atoms, at least one, preferably from 1 to 3 hetero atoms such as nitrogen atom, oxygen atom and sulfur atom. Preferable examples thereof include a 5- or 6-membered monocyclic aliphatic heterocyclic group and a polycyclic or condensed ring aliphatic heterocyclic group. As the aliphatic heterocyclic group, illustrative examples thereof include 2-oxo-1-pyrrolidinyl group, piperidino group, piperazinyl group, morpholino group, tetrahydrofuryl group, tetrahydropyranyl group, and tetrahydrothienyl group.

These aliphatic heterocyclic groups may have a substituent group, and as the substituent group, the groups described in the description on the substituent group of the alkyl group can be mentioned.

Among these, as each of $R^1$ to $R^4$, a hydrogen atom, an alkyl group which may have a substituent group, and an aralkyl group which may have a substituent group are desirable, and particularly, a hydrogen atom and an alkyl group substituted by a phenyl group which may have a substituent group are desirable.

Among these, as each of $R^5$ to $R^{10}$, a hydrogen atom, an alkyl group which may have a substituent group, a cycloalkyl group which may have a substituent group, and an aryl group which may have a substituent group are desirable, and particularly, a hydrogen atom, an alkyl group which may have a substituent group, a phenyl group which may have a substituent group, and a cyclohexyl group which may have a substituent group are desirable.

Next, A is described.

A represents, when n=0, a hydrogen atom, a hetero atom which may have a substituent group, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amido group which may have a substituent group, an aromatic heterocyclic group which may have a substituent group or an aliphatic heterocyclic group which may have a substituent group, an oligomer chain, or a polymer chain.

As the hetero atom, an oxygen atom, a nitrogen atom, a silicon atom and the like can be mentioned.

These hetero atoms may have a substituent group, and as the substituent group, examples thereof include a hydrogen atom, an alkyl group, an alkenyl group, an alkynyl group, an aryl group, an aliphatic heterocyclic group and an aromatic heterocyclic group, and illustrative examples thereof include the groups which are enumerated in the description of $R^1$ to $R^{10}$ or the groups which are enumerated in the description on the substituent group of the alkyl group in the description of $R^1$ to $R^{10}$.

The alkyl groups which may have a substituent group include the cycloalkyl group which may have a substituent group, the alkenyl group which may have a substituent group, the aryl group which may have a substituent group, the aralkyl group which may have a substituent group, the alkoxy group which may have a substituent group, the carboxyl group which may have a substituent group, the alkoxycarbonyl group which may have a substituent group, the amido group which may have a substituent group, the aromatic heterocyclic group which may have a substituent group, the aliphatic heterocyclic group which may have a substituent group, and the groups described in the description of $R^1$ to $R^{10}$.

As the oligomer chain, generally used ones can be mentioned, including oligomer chains such as polystyrene, polyethylene glycol, polyacrylate, polymethacrylate, polyester, polyamide, polyethylene, polypropylene, polycarbonate, polyurethane and polypeptide, and copolymers thereof.

As the polymer chain, generally used ones can be mentioned, and examples thereof include polymer chains such as polystyrene, polyethylene glycol, polyacrylate, polymethacrylate, polyester, polyamide, polyethylene, polypropylene, polycarbonate, polyurethane and polypeptide, and copolymers thereof.

Among these, a hydrogen atom, an alkyl group which may have a substituent group, a cycloalkyl group which may have a substituent group, and an aryl group which may have a substituent group are desirable, and particularly, a hydrogen atom, an alkyl group which may have a substituent group, a phenyl group which may have a substituent group, and a cyclohexyl group which may have a substituent group are desirable.

The hetero atom, the alkylene group, the alkylene group which includes an arylene group, the alkylene group which includes a cycloalkylene group, the alkylene group which includes a hetero atom, the divalent aliphatic hydrocarbon cyclic group, the divalent aliphatic heterocyclic group, the divalent aromatic hydrocarbon cyclic group, the divalent aromatic heterocyclic group, the oligomer chain, and the polymer chain, as A when n=1 to 3, are described. Each of these groups may have a substituent group.

As the hetero atom, an oxygen atom, a nitrogen atom, and a silicon atom can be mentioned.

These hetero atoms may have a substituent group, and as the substituent group, examples thereof include a hydrogen atom, an alkyl group, an alkenyl group, an alkynyl group, an aryl group, an aliphatic heterocyclic group and an aromatic heterocyclic group, and illustrative examples thereof include the groups which are enumerated in the description of $R^1$ to $R^{10}$ or the groups which are enumerated as the substituent group of the alkyl group described in the description of $R^1$ to $R^{10}$.

As the alkylene group, examples thereof include a chain or branched alkyl group having from 1 to 30 carbon atoms, preferably from 1 to 10 carbon atoms, from which one hydrogen atom is removed, and illustrative examples thereof include the alkyl group described in the description of $R^1$ to $R^{10}$, from which one hydrogen atom is removed.

These alkylene groups may have a substituent group, and as the substituent group, the substituent group of the alkyl group described in the description of $R^1$ to $R^{10}$ can be mentioned.

As the alkylene group including an arylene group, the aforementioned alkylene group including an arylene group can be mentioned. As the arylene group, the divalent aromatic hydrocarbon cyclic group that will be described later can be mentioned. The arylene group may have a substituent group, and as the substituent group, the substituent group of the alkyl group described in the description of $R^1$ to $R^{10}$ can be mentioned.

These alkylene groups including arylene group may have a substituent group, and as the substituent group, the substituent group of the alkyl group described in the description of $R^1$ to $R^{10}$ can be mentioned.

As the alkylene group including a cycloalkylene group, the aforementioned alkylene group including a cycloalkylene group can be mentioned. As the cycloalkylene group, the divalent aliphatic hydrocarbon cyclic group that will be described later can be mentioned. The cycloalkylene group may have a substituent group, and as the substituent group, the substituent group of the alkyl group described in the description of $R^1$ to $R^{10}$ can be mentioned.

These alkylene groups including cycloalkylene group may have a substituent group, and as the substituent group, the substituent group of the alkyl group described in the description of $R^1$ to $R^{10}$ can be mentioned.

As the alkylene group including a hetero atom, the aforementioned alkylene group including a hetero atom can be mentioned. As the hetero atom, an oxygen atom, a nitrogen atom and silicon atom can be mentioned.

These alkylene groups including a hetero atom may have a substituent group, and as the substituent group, the substituent group of the alkyl group described in the description of $R^1$ to $R^{10}$ can be mentioned.

As the divalent aliphatic hydrocarbon cyclic group, a divalent group derived from the cycloalkyl group described in the description of $R^1$ to $R^{10}$ can be mentioned.

These divalent aliphatic hydrocarbon cyclic groups may have a substituent group, and as the substituent group, the substituent group of the alkyl group described in the description of $R^1$ to $R^{10}$ can be mentioned.

As the divalent aliphatic heterocyclic group, a divalent group derived from the aliphatic heterocyclic group described in the description of $R^1$ to $R^{10}$ can be mentioned.

These divalent aliphatic heterocyclic groups may have a substituent group, and as the substituent group, the substituent group of the alkyl group described in the description of $R^1$ to $R^{10}$ can be mentioned.

As the divalent aromatic hydrocarbon cyclic group, a divalent group derived from the aryl group described in the description of $R^1$ to $R^{10}$ can be mentioned.

These divalent aromatic hydrocarbon cyclic groups may have a substituent group, and as the substituent group, the substituent group of the alkyl group described in the description of $R^1$ to $R^{10}$ can be mentioned.

As the divalent aromatic heterocyclic group, a divalent group derived from the aromatic heterocyclic group described in the description of $R^1$ to $R^{10}$ can be mentioned.

These divalent aromatic heterocyclic groups may have a substituent group, and as the substituent group, the substituent group of the alkyl group described in the description of $R^1$ to $R^{10}$ can be mentioned.

The divalent aliphatic hydrocarbon cyclic group, divalent aliphatic heterocyclic group, divalent aromatic hydrocarbon cyclic group, and divalent aromatic heterocyclic group may have a polycyclic structure.

A may be connected to an alkylene group, an alkylene group which includes an arylene group, an alkylene group which includes a cycloalkylene group, an alkylene group which includes a hetero atom, a divalent aliphatic hydrocarbon cyclic group, a divalent aliphatic heterocyclic group, a divalent aromatic hydrocarbon cyclic group, and a divalent aromatic heterocyclic group.

As the oligomer chain, generally used ones can be mentioned, and examples thereof include oligomer chains such as polystyrene, polyethylene glycol, polyacrylate, polymethacrylate, polyester, polyamide, polyethylene, polypropylene, polycarbonate, polyurethane and polypeptide, and copolymers thereof.

As the polymer chain, generally used ones can be mentioned, and examples thereof include polymer chains such as polystyrene, polyethylene glycol, polyacrylate, polymethacrylate, polyester, polyamide, polyethylene, polypropylene, polycarbonate, polyurethane and polypeptide, and copolymers thereof.

As A when n=1 to 3, among these, an alkylene group, an alkylene group including an arylene group, an alkylene group including a cycloalkylene group, a divalent aliphatic hydrocarbon cyclic group, and a divalent aromatic hydrocarbon cyclic group are desirable. Further, an alkylene group, an alkylene group including a cyclohexylene group, an alkylene group including a phenylene group, a phenylene group, a naphthylene group, a polycyclic phenylene group, a group in which a phenylene group is connected to an alkylene group, and a group in which a cyclohexylene group is connected to an alkylene group are particularly desirable. Each of these groups may have a substituent group.

Next, $X^1$, $X^2$, $X^3$, $X^4$, $X^5$ and $X^6$ are described. $X^1$, $X^2$, $X^3$, $X^4$, $X^5$ and $X^6$ each independently represent an oxygen atom, nitrogen atom, phosphorus atom, or sulfur atom.

Next, $Y^1$ and $Y^2$ are described. $Y^1$ and $Y^2$ each independently represent a carbon atom, silicon atom or sulfur atom.

As a preferred combination of $X^1$, $Y^1$, $X^5$ and $X^3$, for example, those represented in Table 1 below can be mentioned.

TABLE 1

| Entry | $X^1$ | $Y^1$ | $X^5$ | $X^3$ |
|---|---|---|---|---|
| 1 | O | C | O | N |
| 2 | O | C | O | O |
| 3 | O | C | O | S |
| 4 | O | C | S | O |
| 5 | O | C | S | N |
| 6 | O | C | N | N |
| 7 | N | C | O | N |
| 8 | N | C | O | O |
| 9 | N | C | O | S |

TABLE 1-continued

| Entry | $X^1$ | $Y^1$ | $X^5$ | $X^3$ |
|---|---|---|---|---|
| 10 | N | C | S | O |
| 11 | N | C | S | N |
| 12 | N | C | N | N |

Among these, Entries 1, 2, 5, 6, 7, 8, 11 and 12 are preferable, and Entries 1, 2 and 6 are more preferable.

As a preferred combination of $X^2$, $Y^2$, $X^6$ and $X^4$, for example, those represented in Table 2 below can be mentioned.

TABLE 2

| Entry | $X^2$ | $Y^2$ | $X^6$ | $X^4$ |
|---|---|---|---|---|
| 13 | O | C | O | N |
| 14 | O | C | O | O |
| 15 | O | C | O | S |
| 16 | O | C | S | O |
| 17 | O | C | S | N |
| 18 | O | C | N | N |
| 19 | N | C | O | N |
| 20 | N | C | O | O |
| 21 | N | C | O | S |
| 22 | N | C | S | O |
| 23 | N | C | S | N |
| 24 | N | C | N | N |

Further, amino acids in which $R^1$, $R^2$, $R^3$ or $R^4$ is a hydroxycarbonyl group do not meet the optically active cyclic nitrogen-containing compound of the invention represented by the general formula (1).

As illustrative examples of the optically active cyclic nitrogen-containing compound represented by the general formula (1), the following compounds can be mentioned.

In the following compounds, Me represents a methyl group, Et represents an ethyl group, Pr represents a propyl group, iPr represents an isopropyl group, Bu represents a butyl group, tBu represents a tertiary butyl group, Cy represents a cyclohexyl group, Ph represents a phenyl group, Bn represents a benzyl group, TMS represents a trimethylsilyl group, polymer represents a polymer chain, and p represents an integer of two or more.

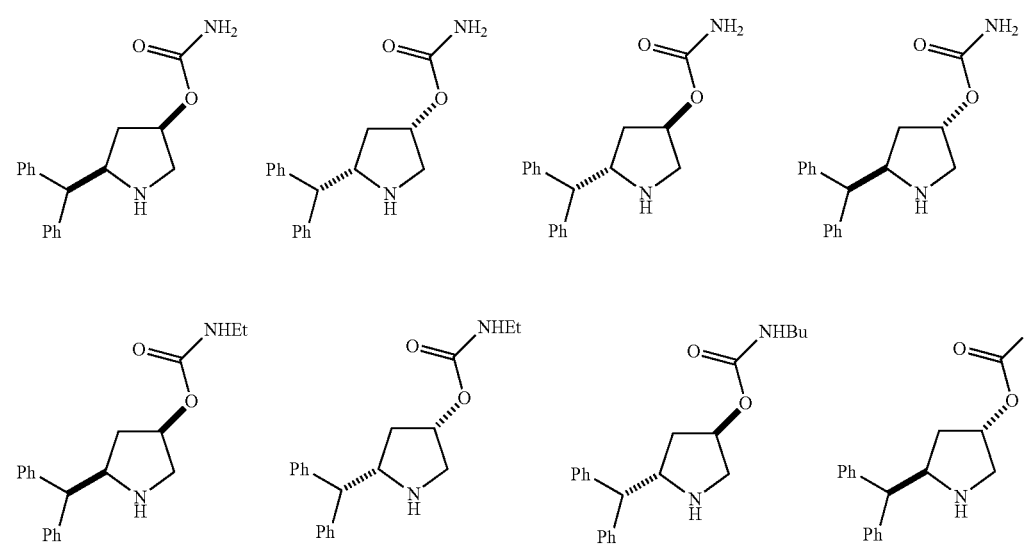

[Chem. 5]

-continued
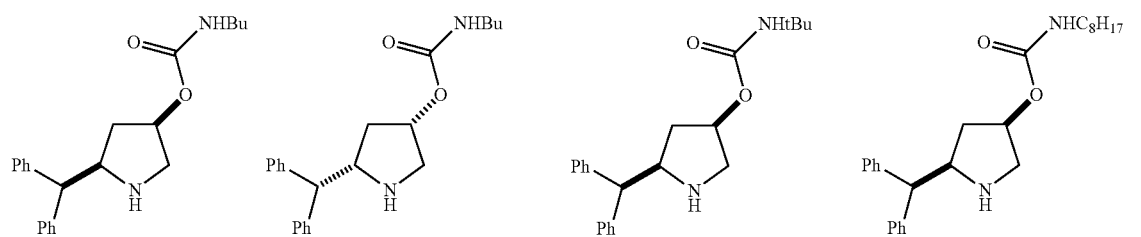
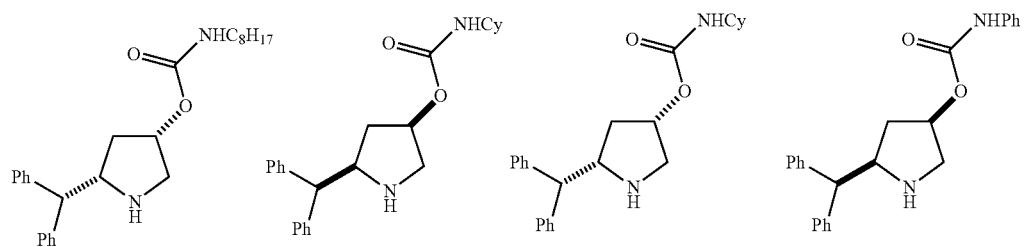
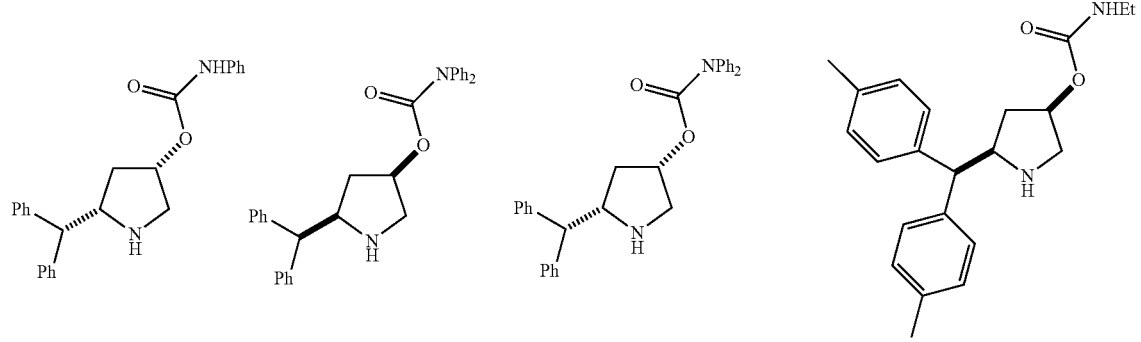
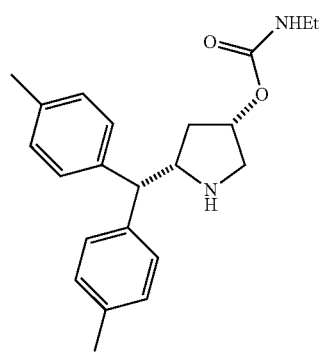
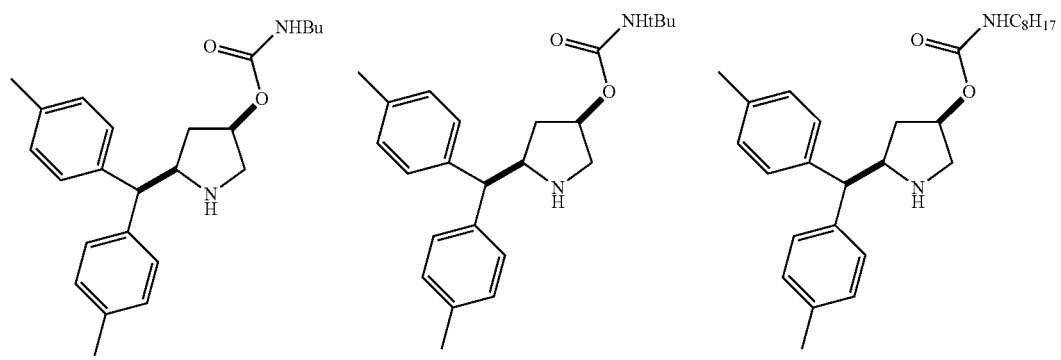

-continued
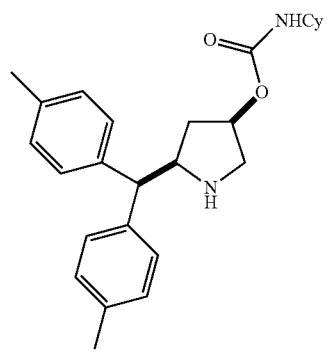 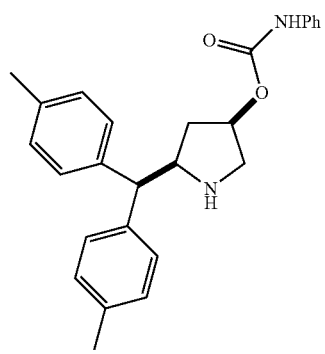 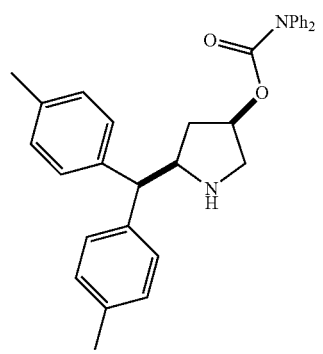
[Chem. 6]
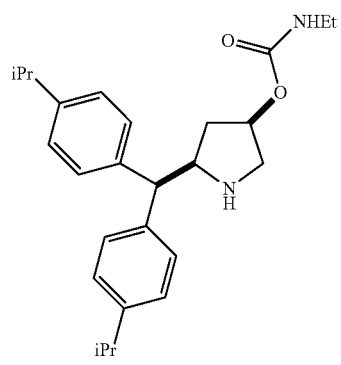 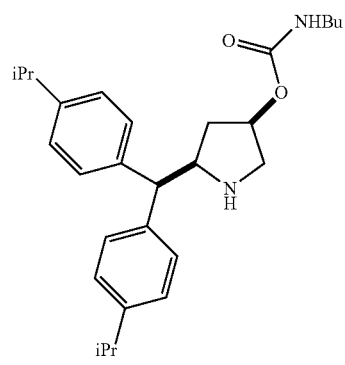 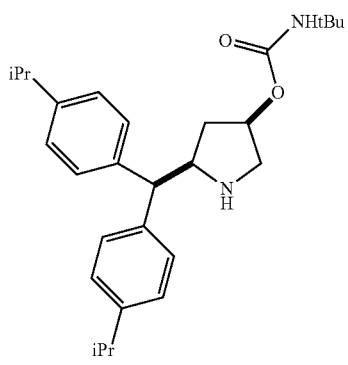
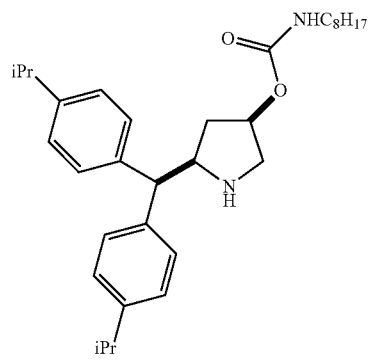 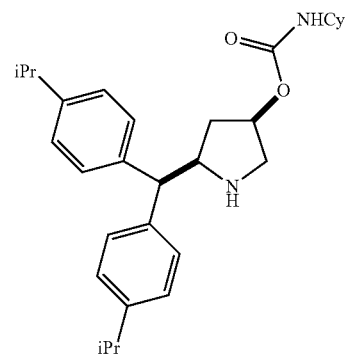 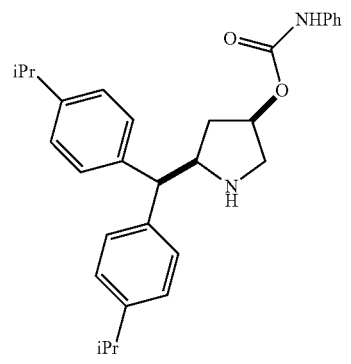
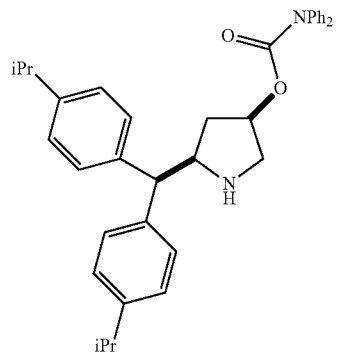 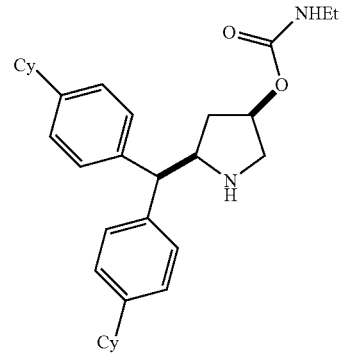 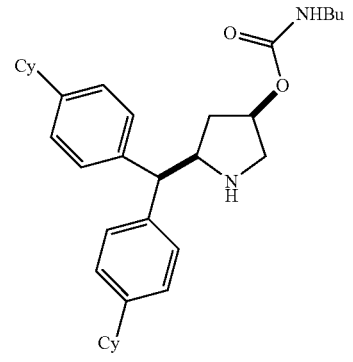

-continued
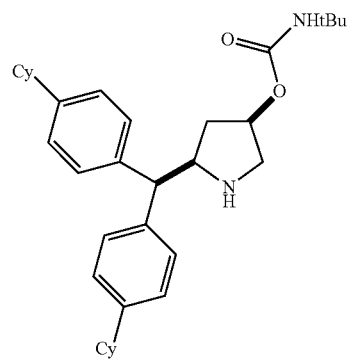 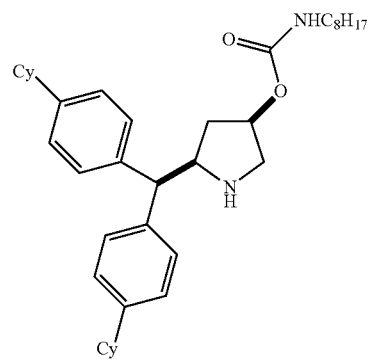 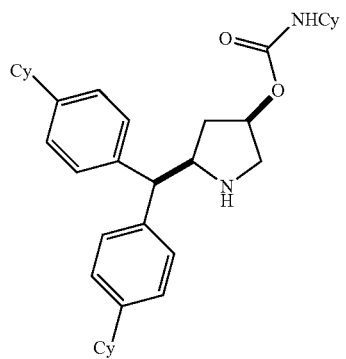
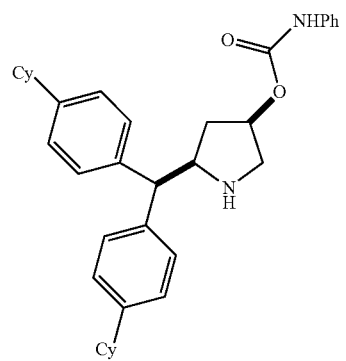 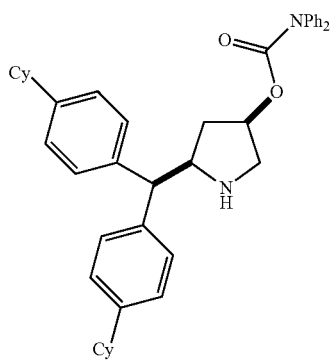
[Chem. 7]
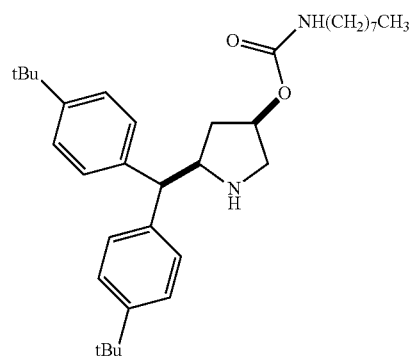 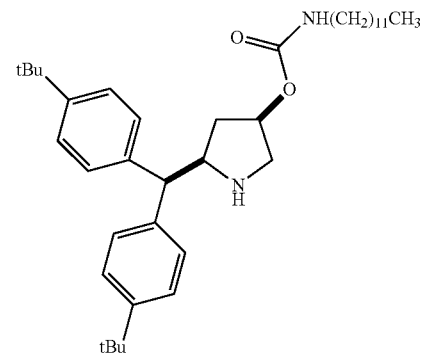
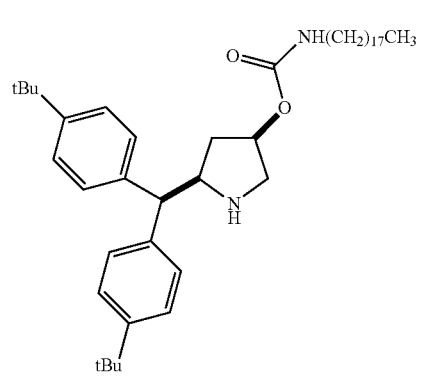 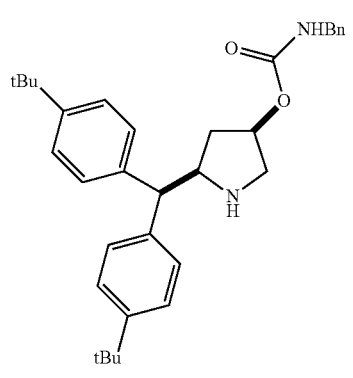 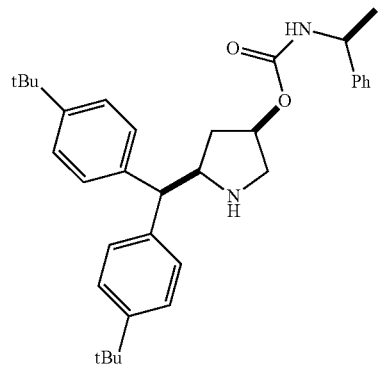

-continued
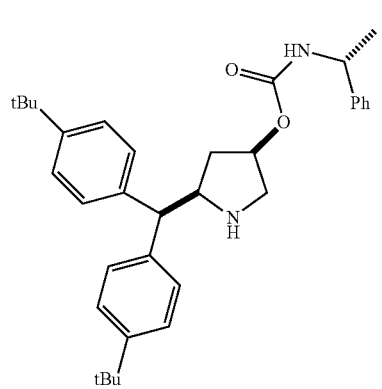
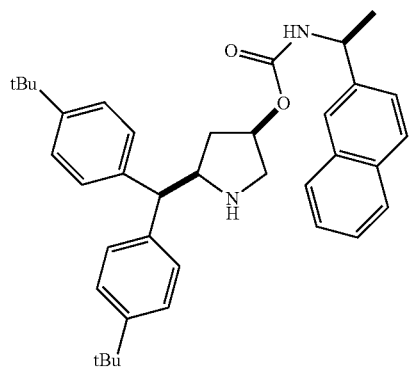
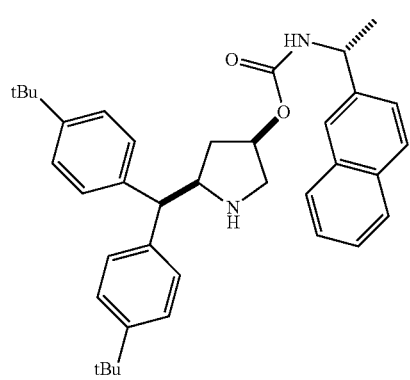
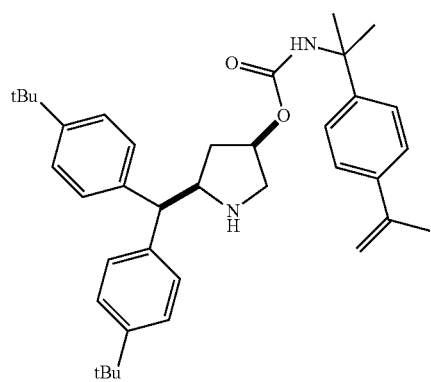
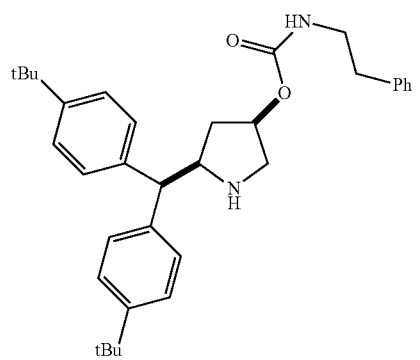
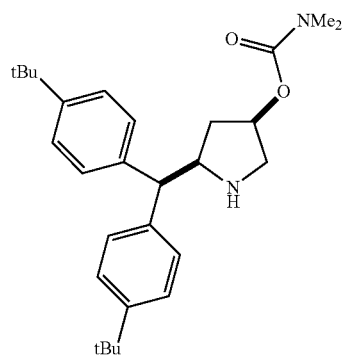
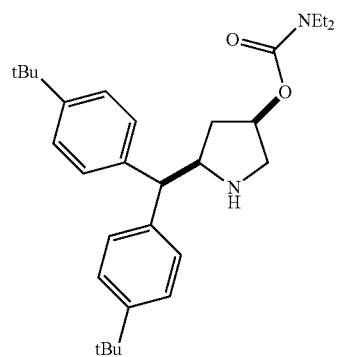

-continued
[Chem. 8]
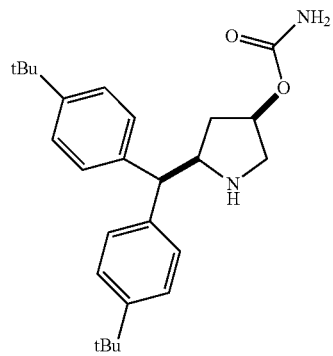 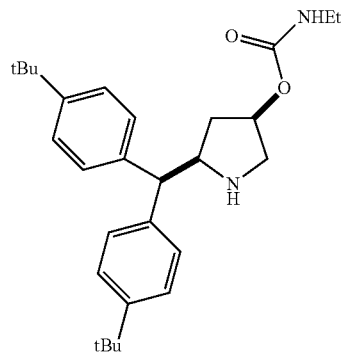 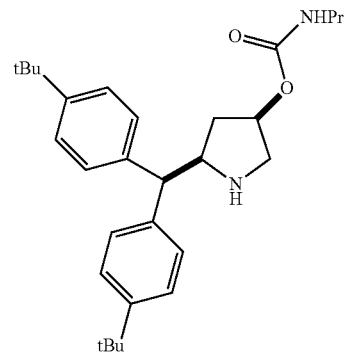
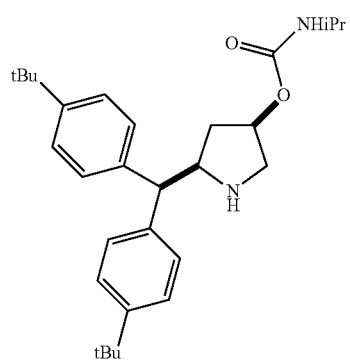 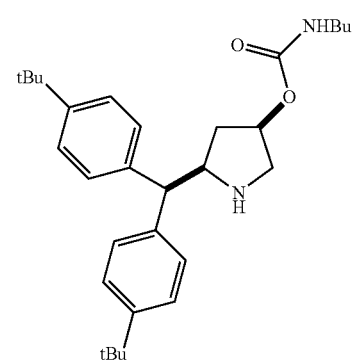 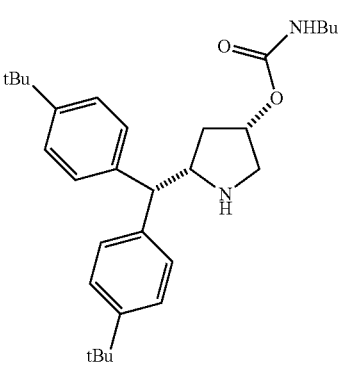
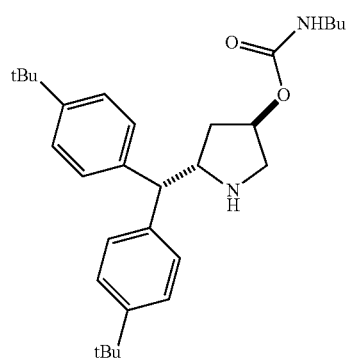 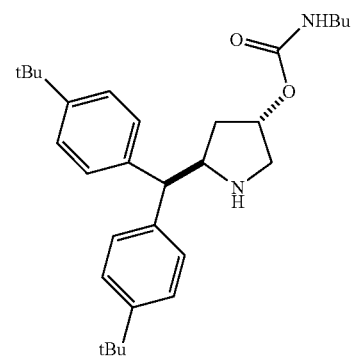 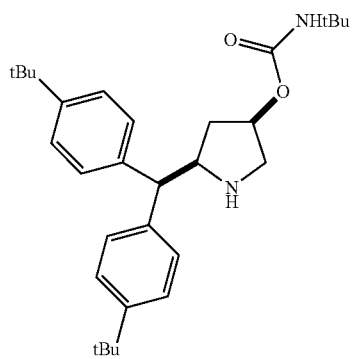
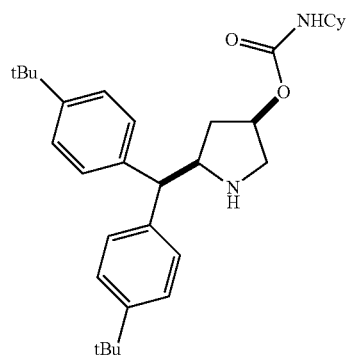

-continued
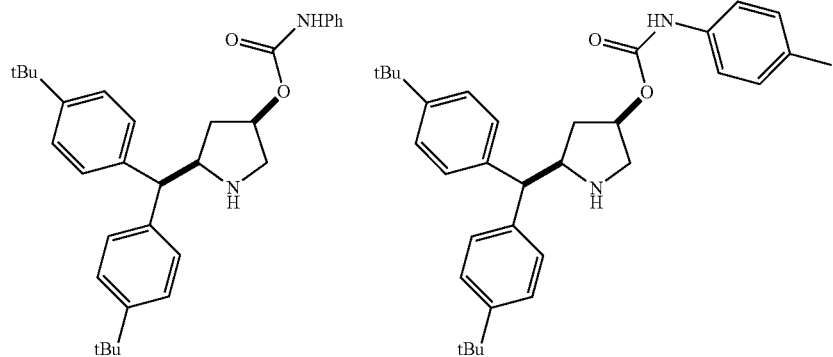
[Chem. 9]
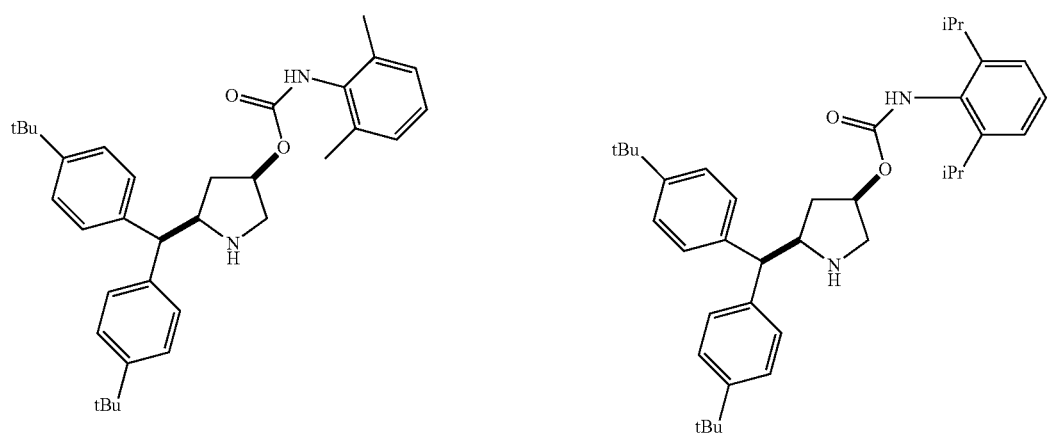
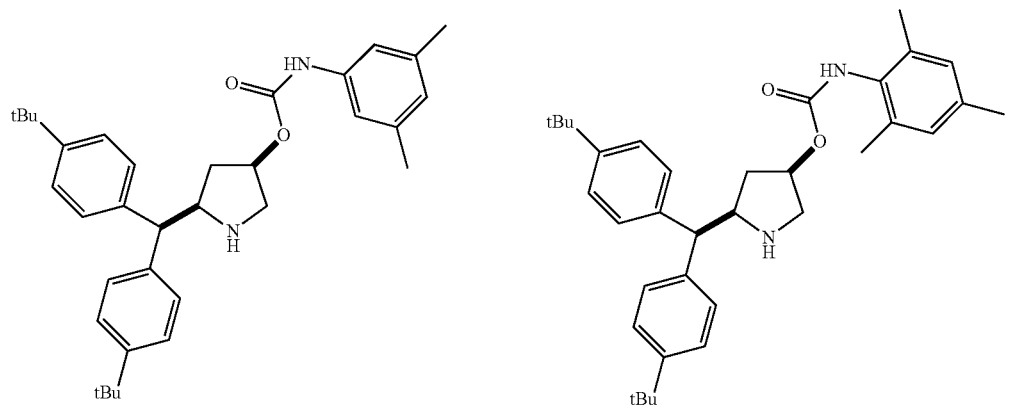
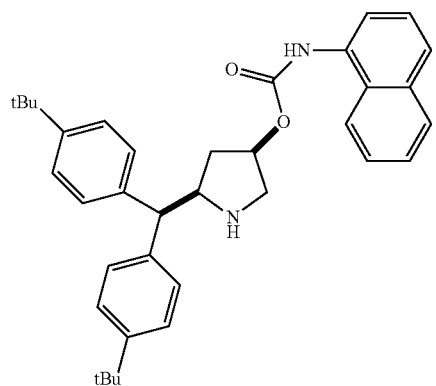

29
30
-continued
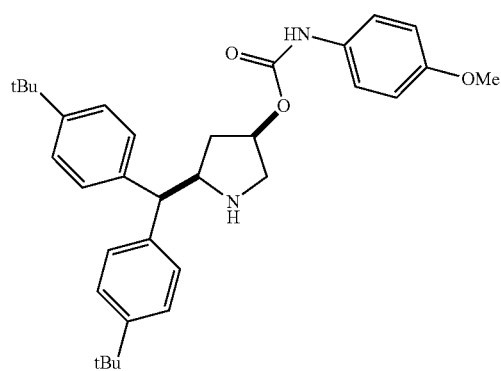
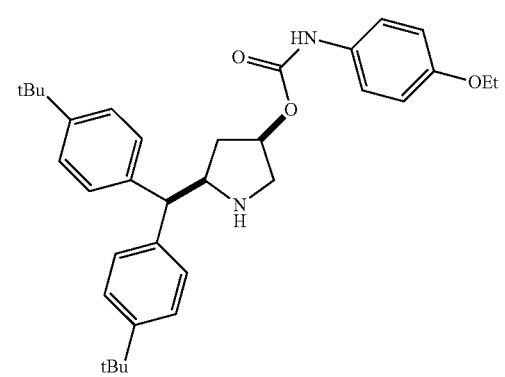
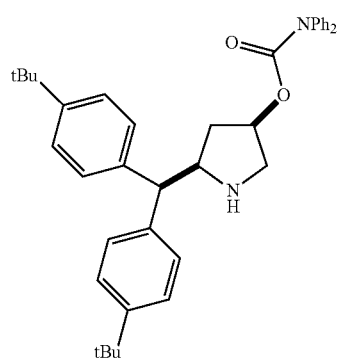
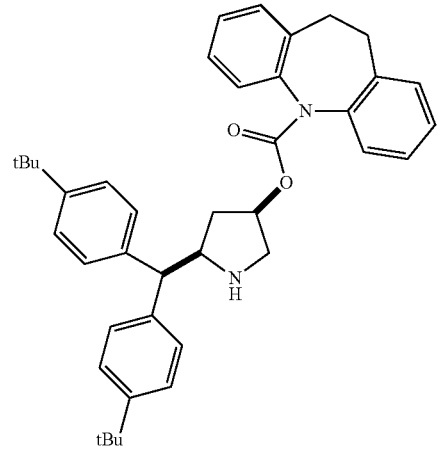
[Chem. 10]
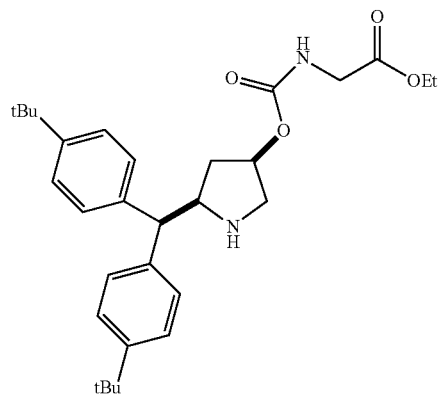
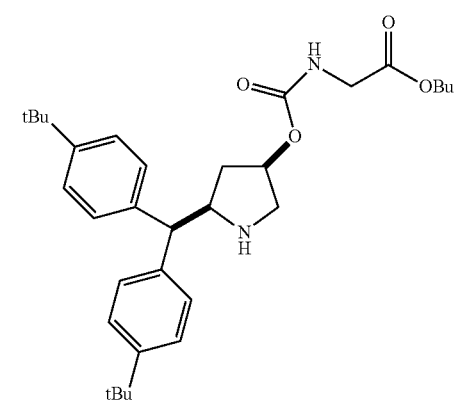
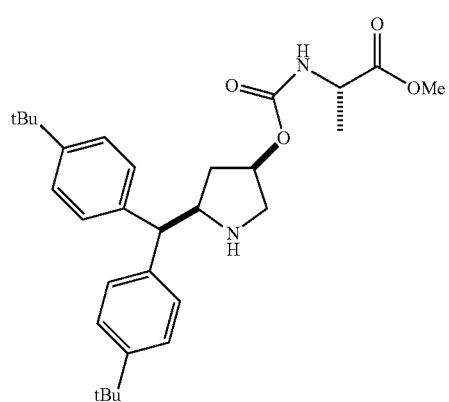
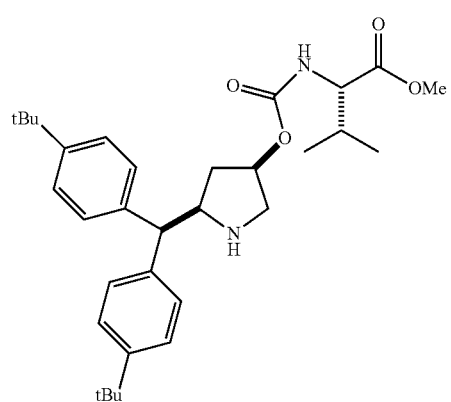

-continued
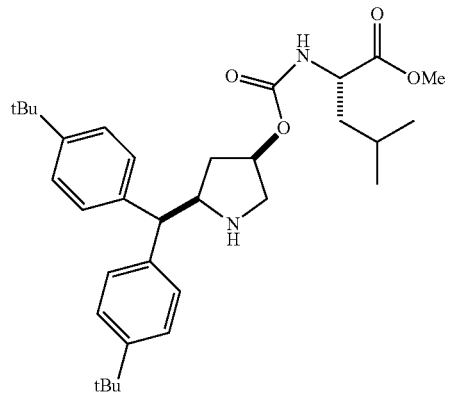
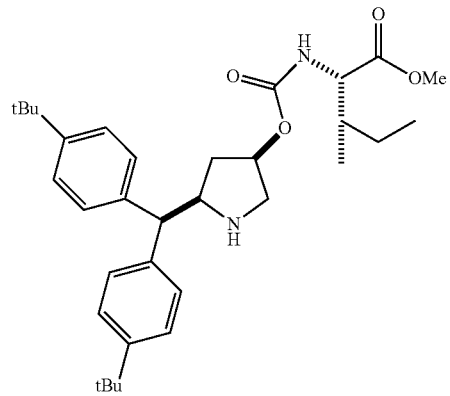
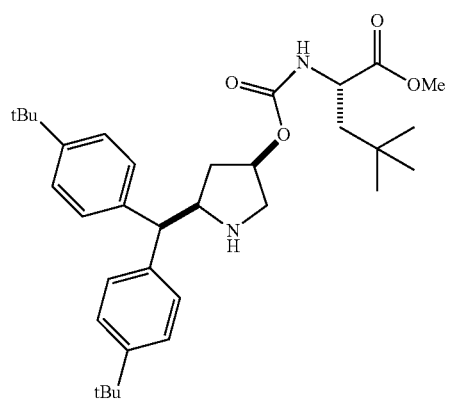
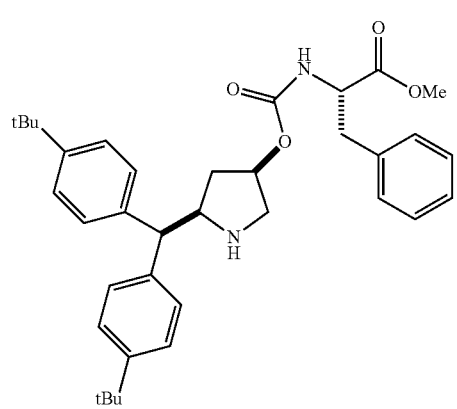
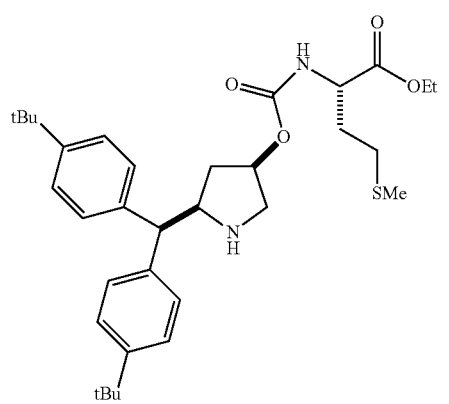
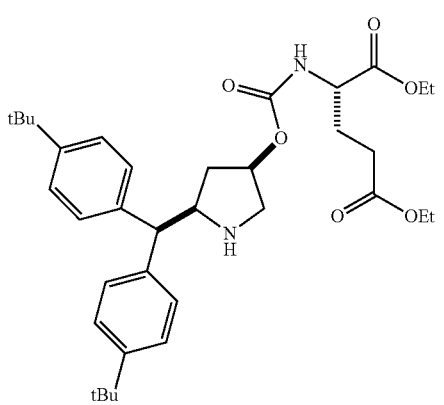
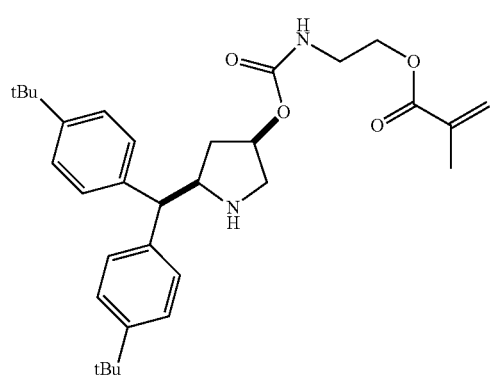
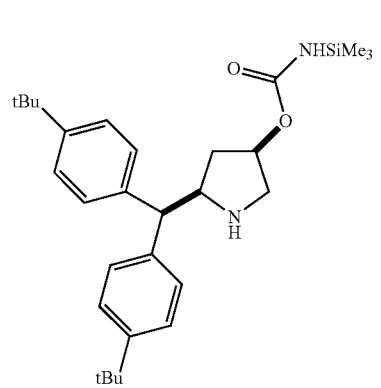

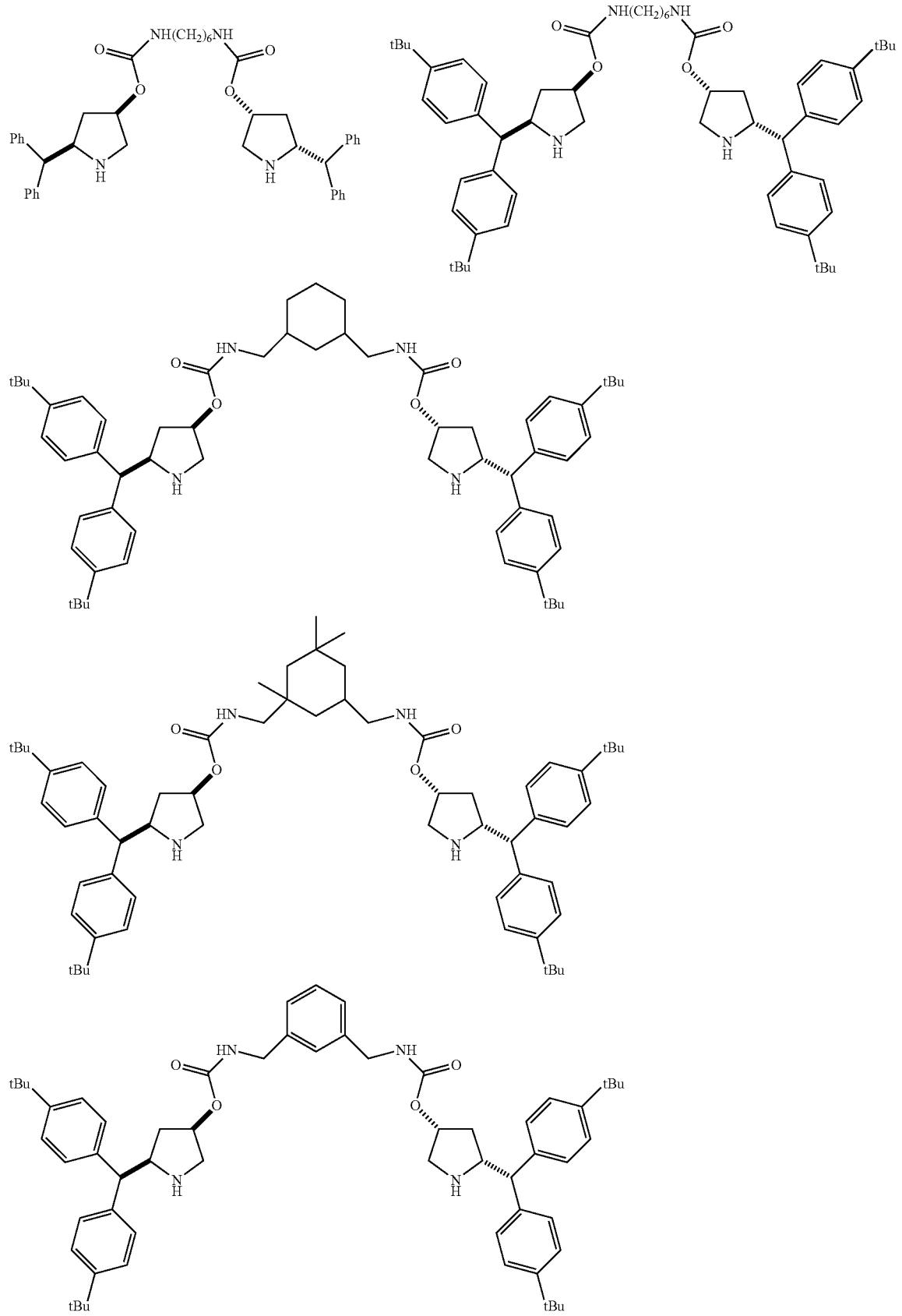

-continued
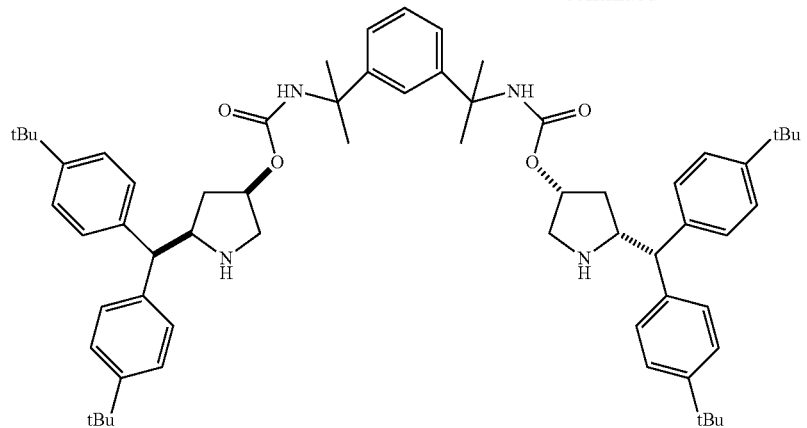
[Chem. 12]
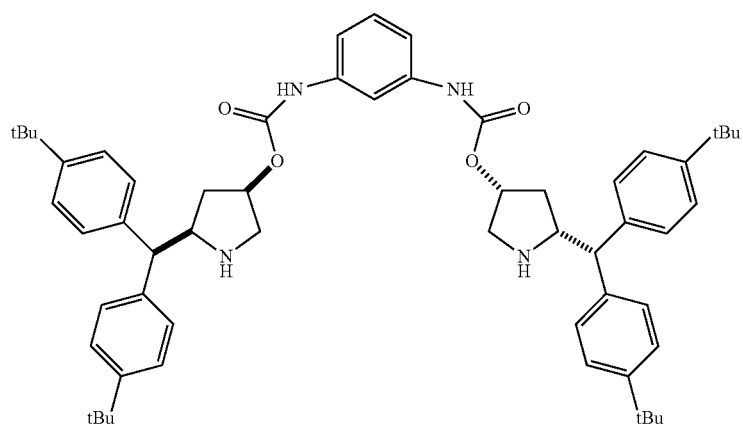
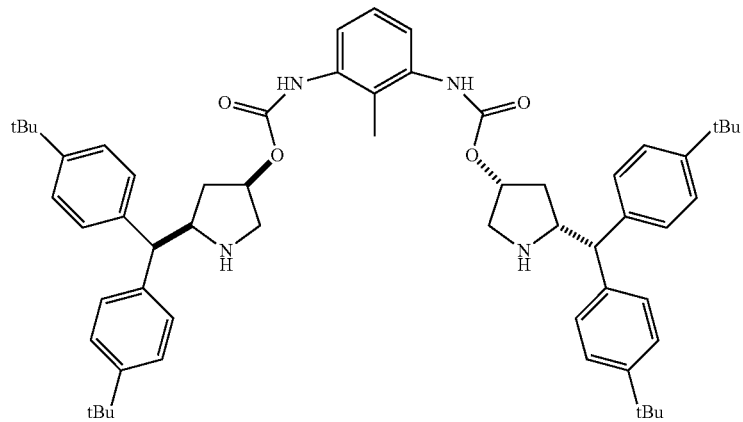
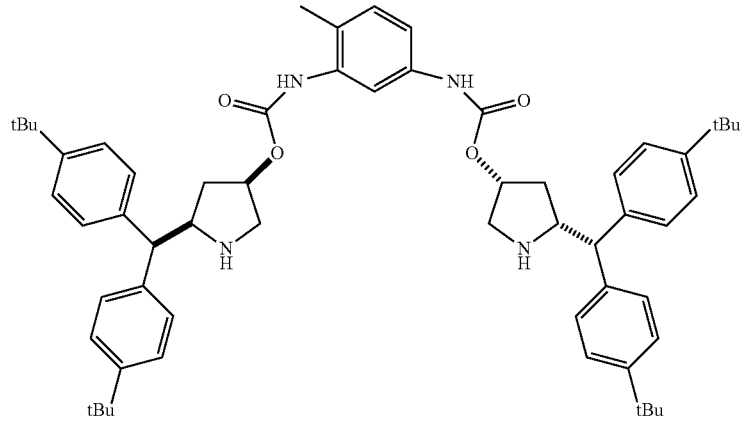

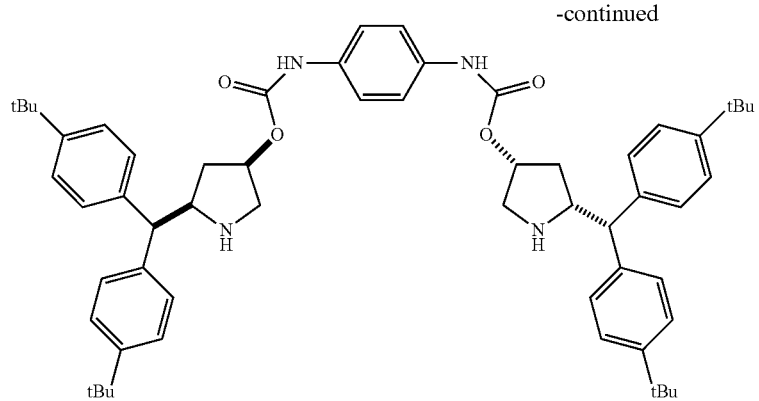
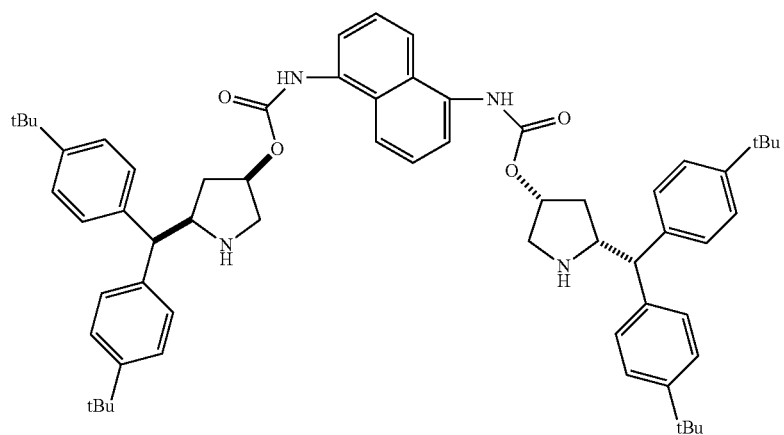
[Chem. 13]
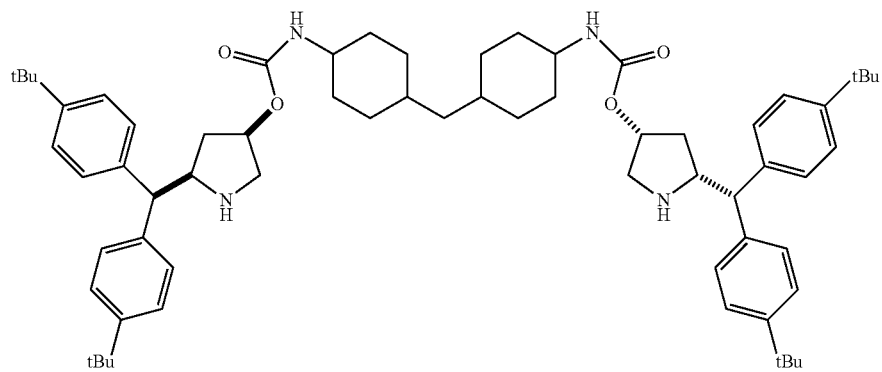
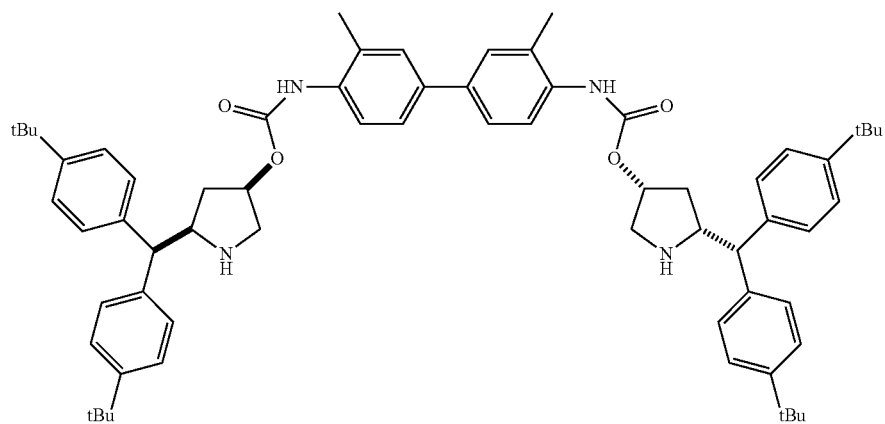

-continued
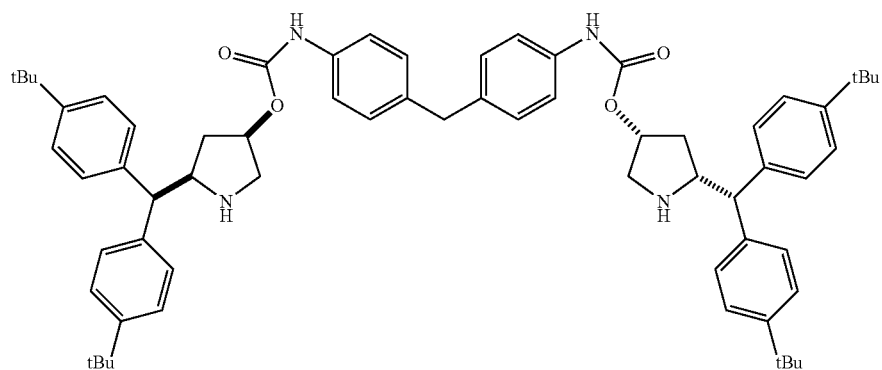
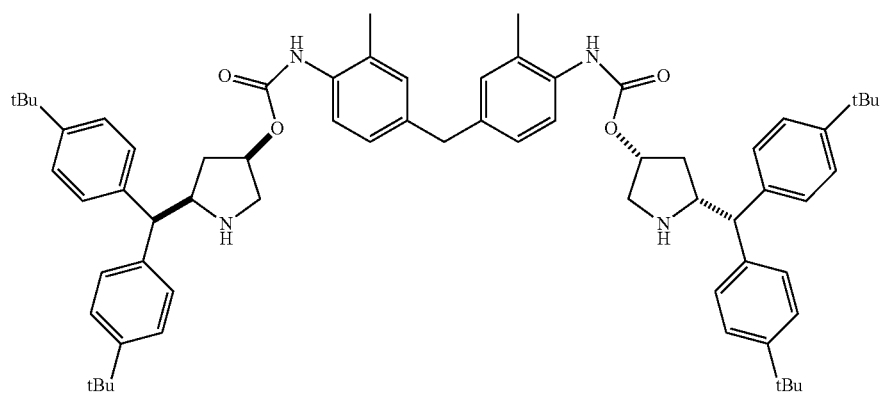
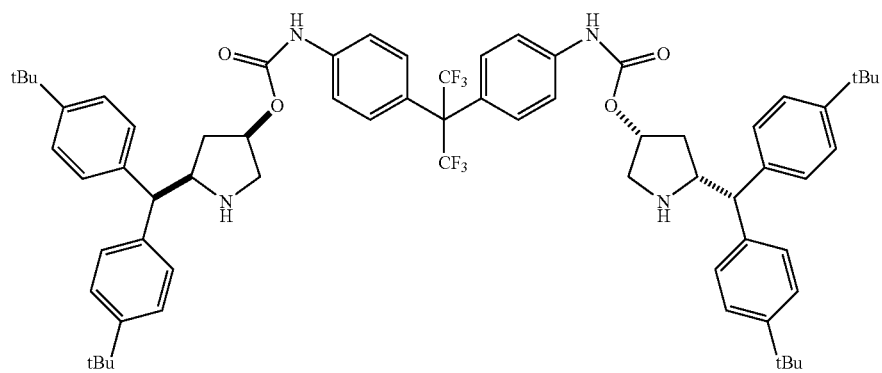
[Chem. 14]
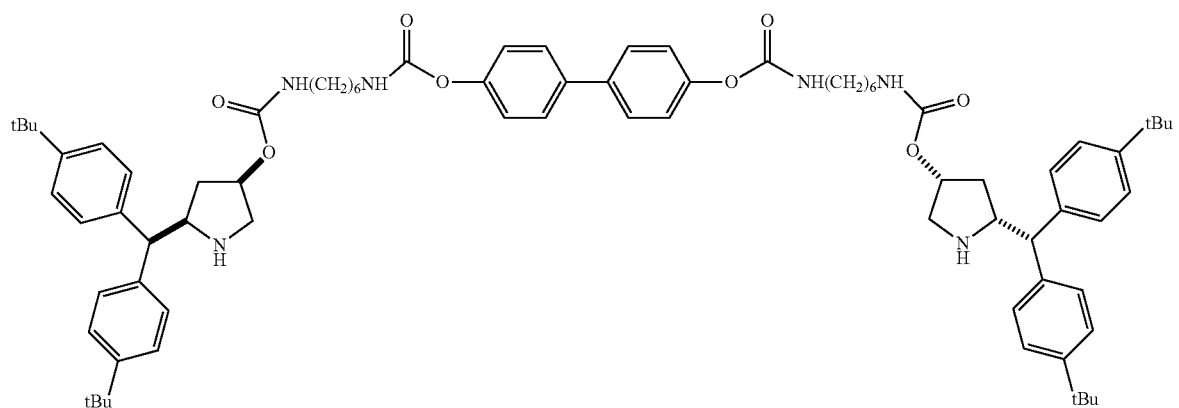

41 42
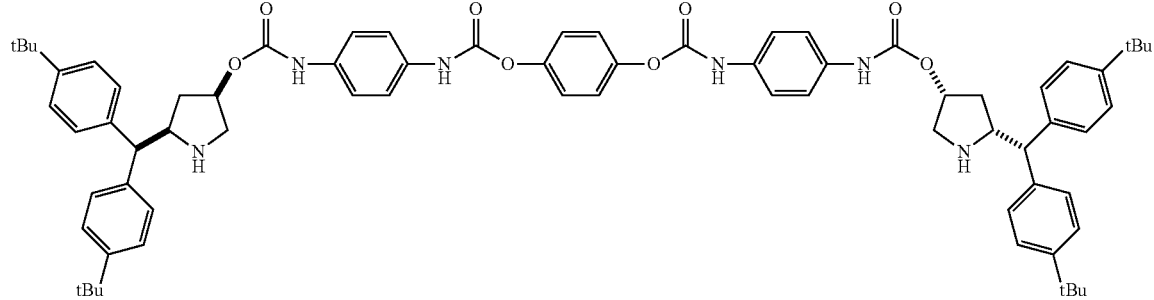
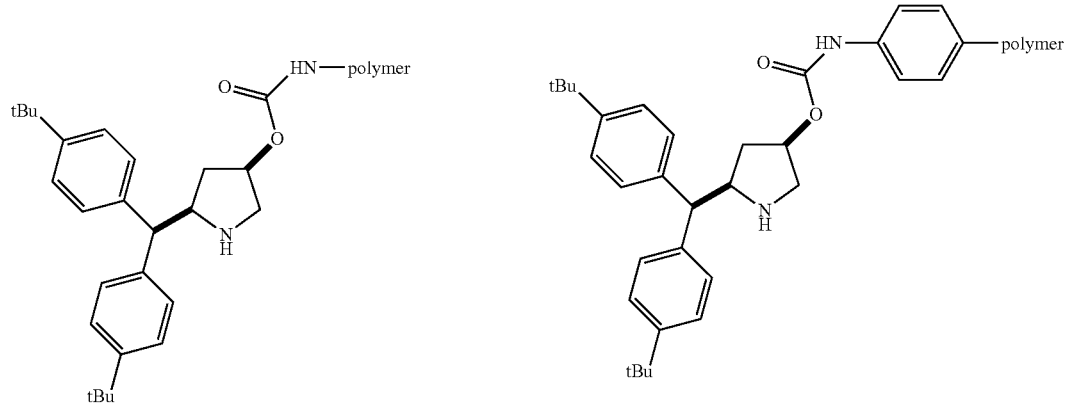
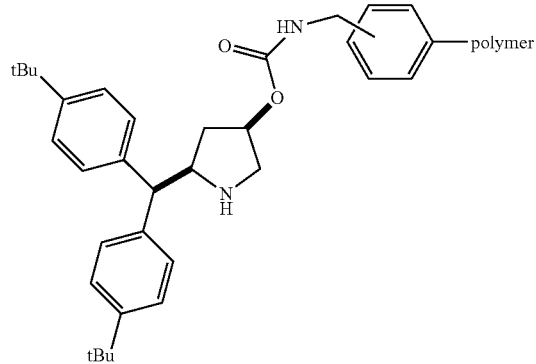
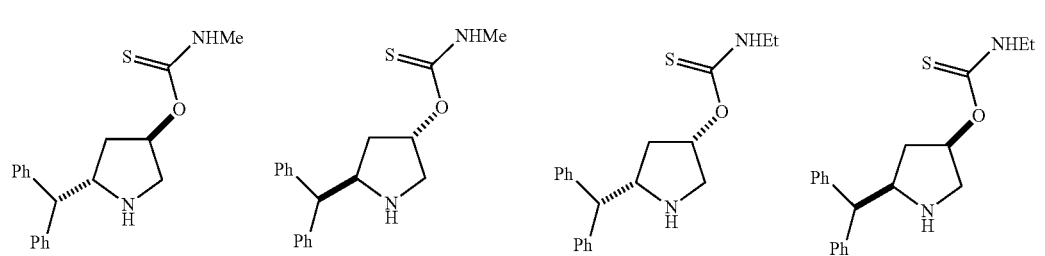
[Chem. 15]
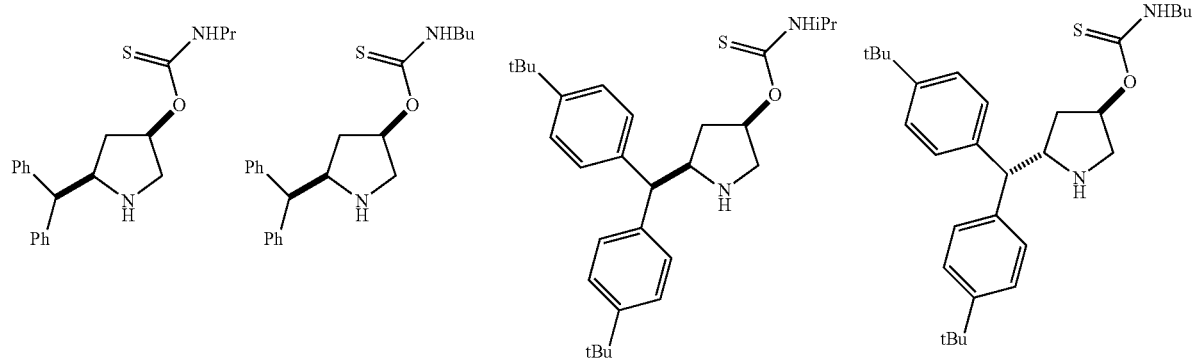

-continued
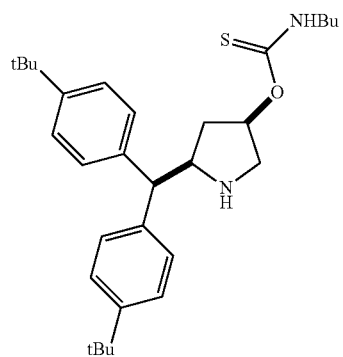
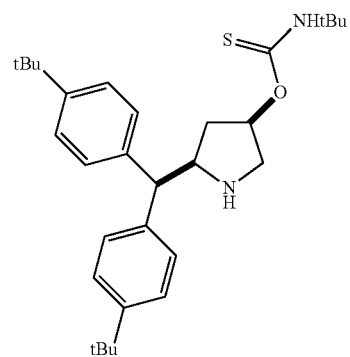
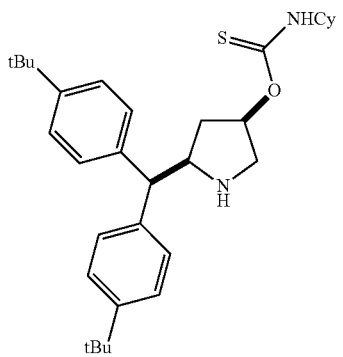
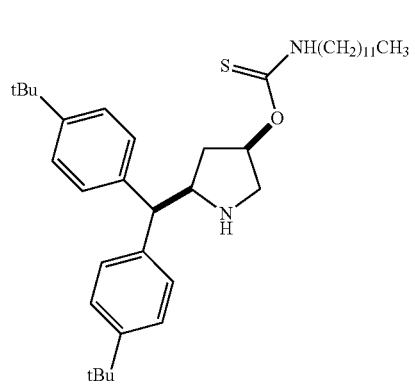
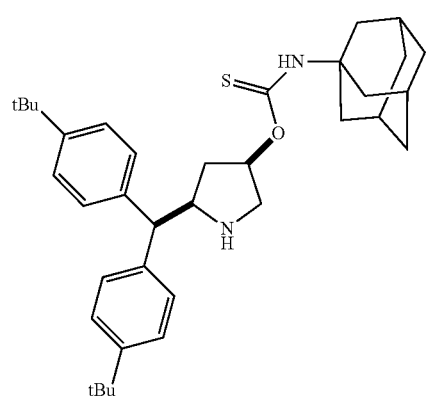
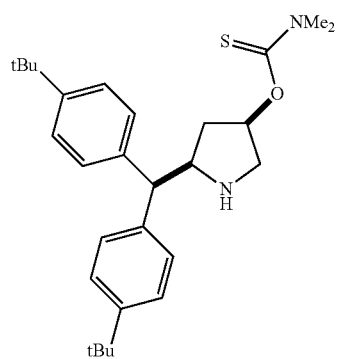
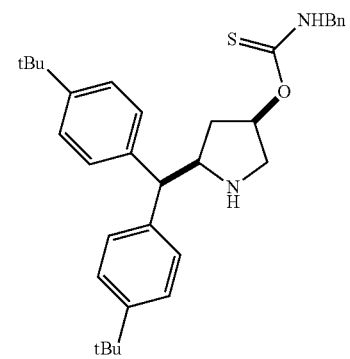
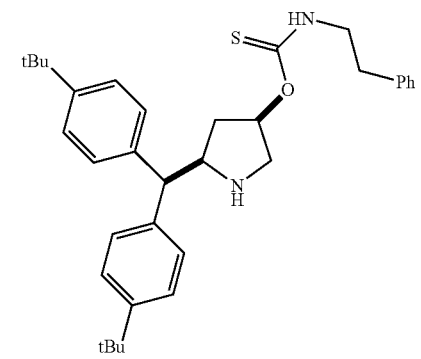
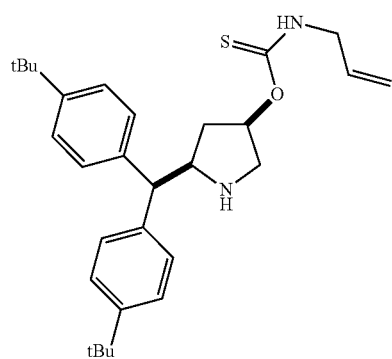
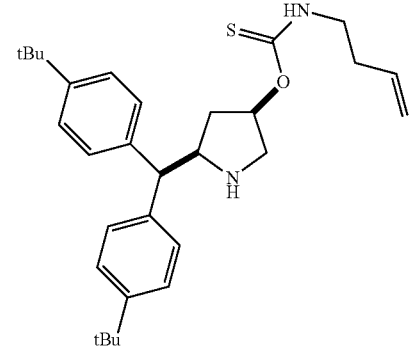

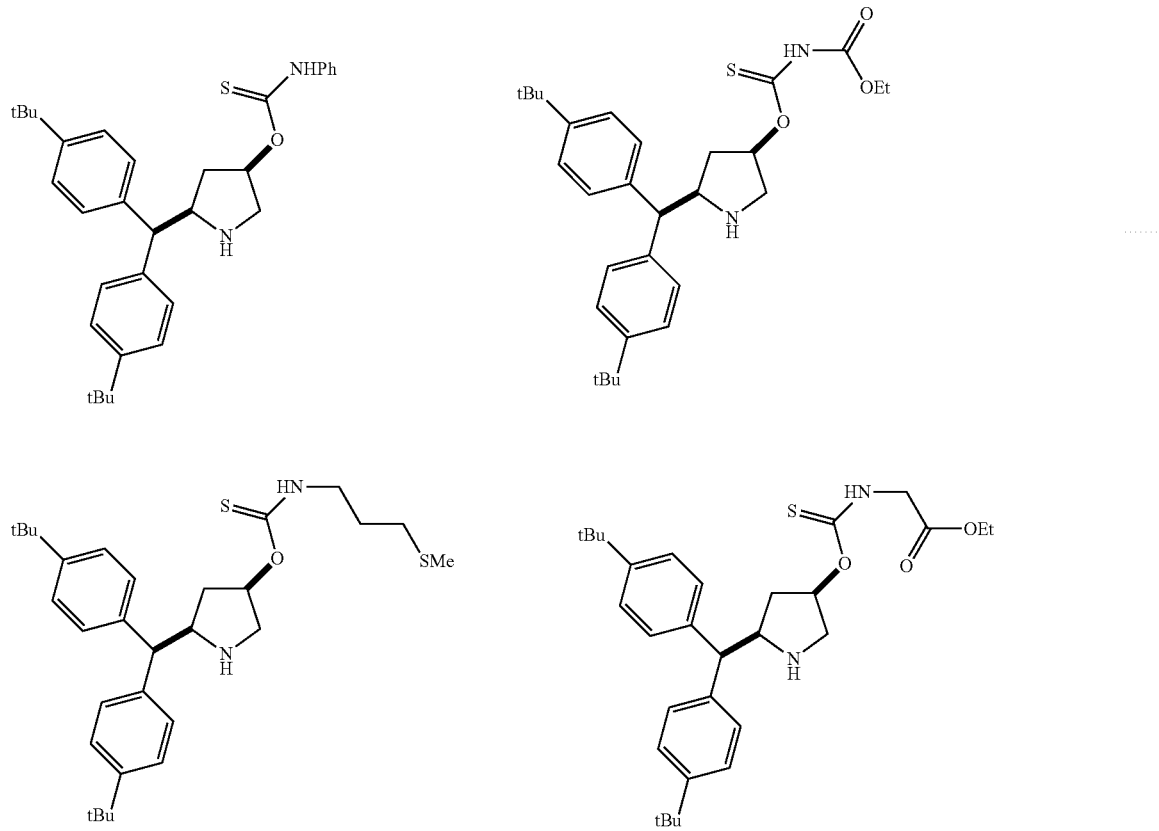
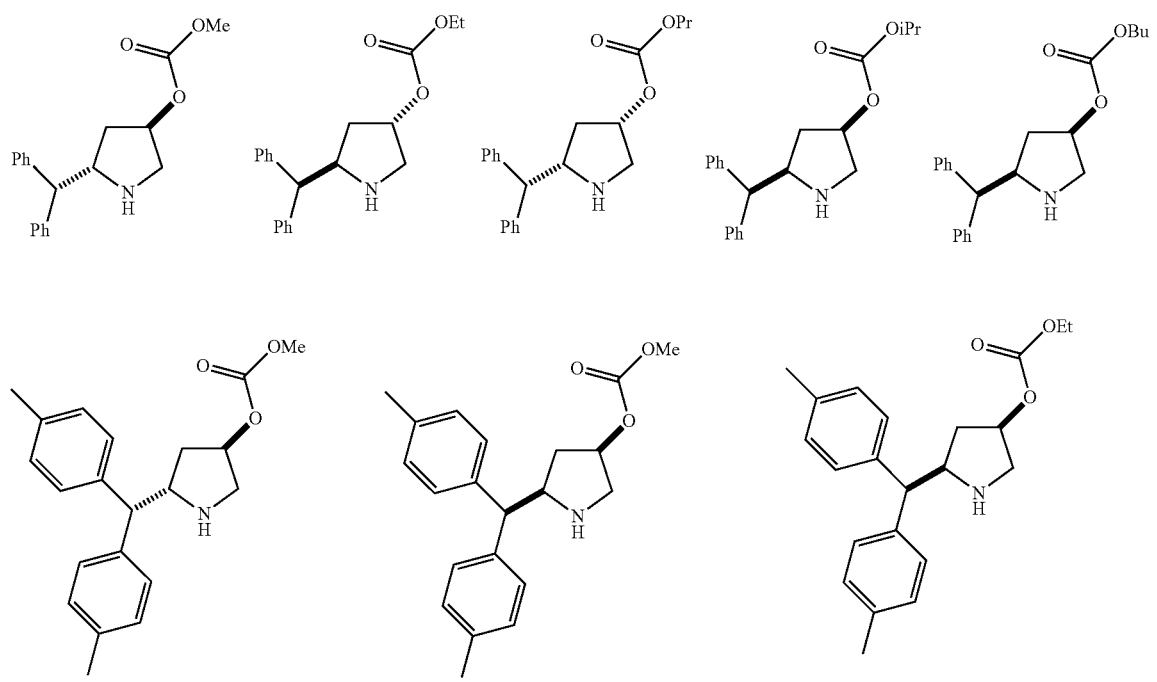

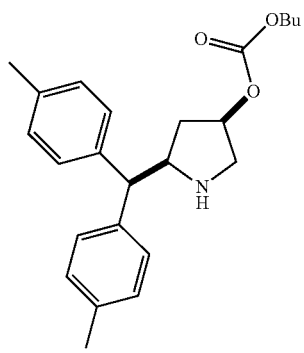
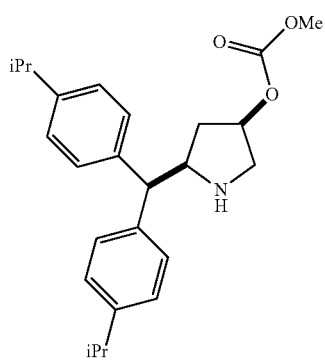
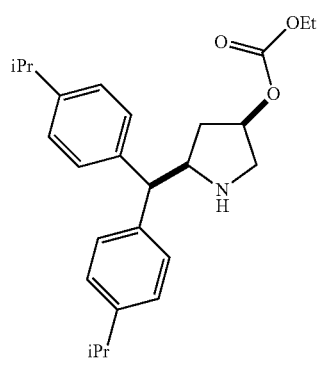
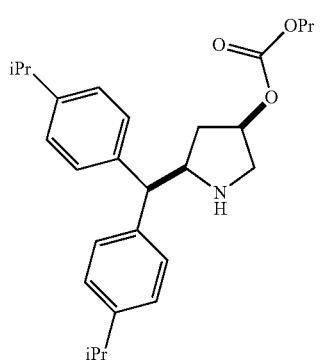
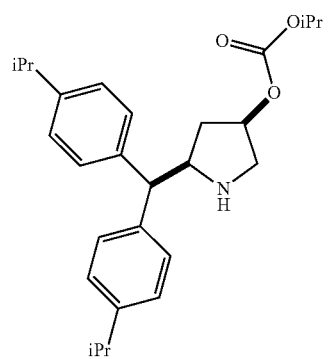
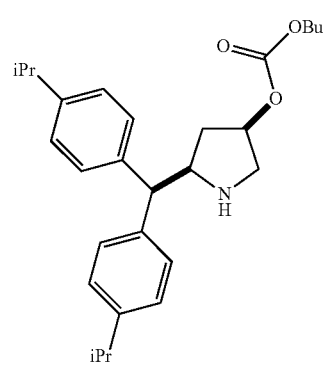
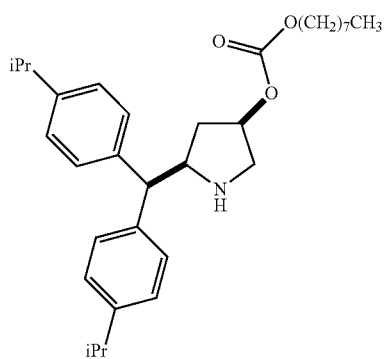
[Chem. 18]
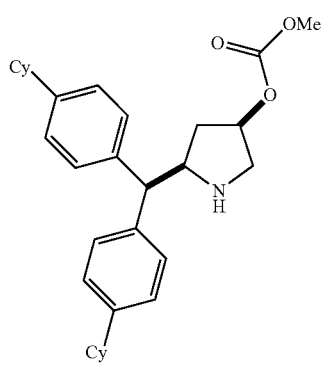
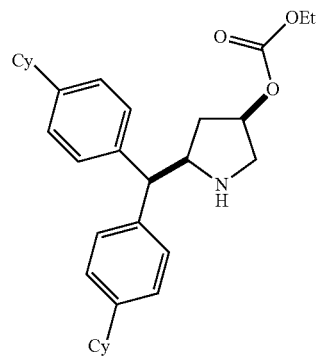
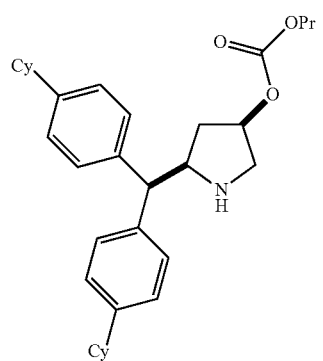

-continued
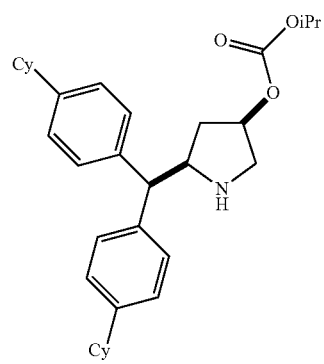
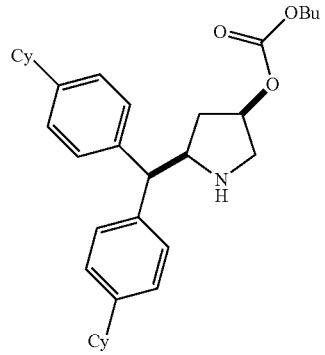
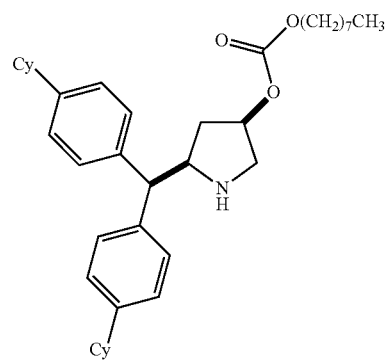
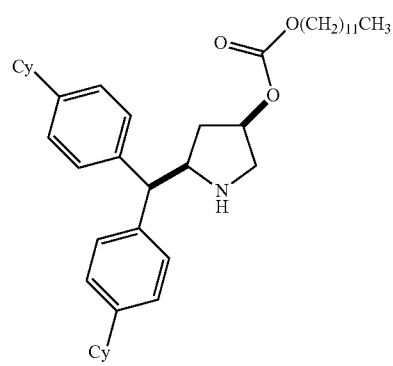
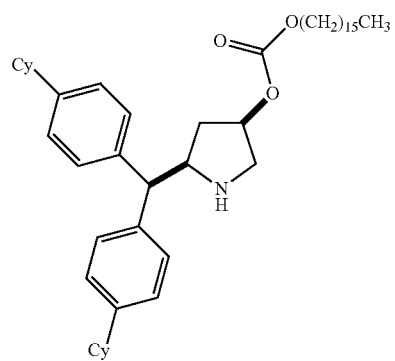
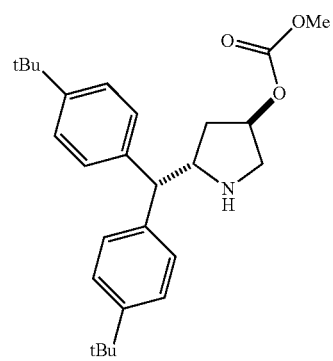
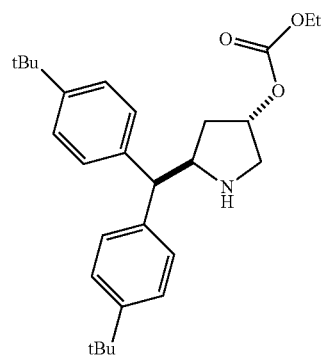
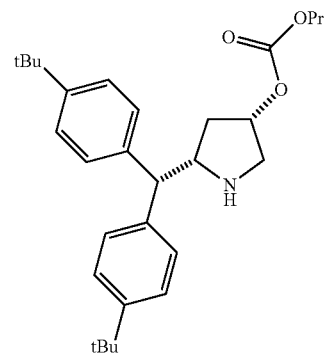
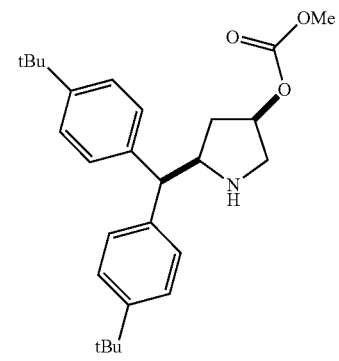
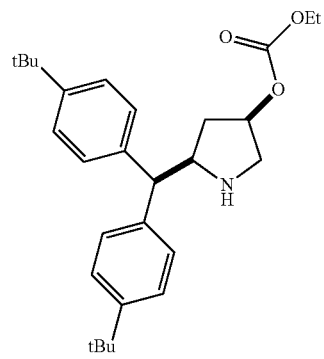
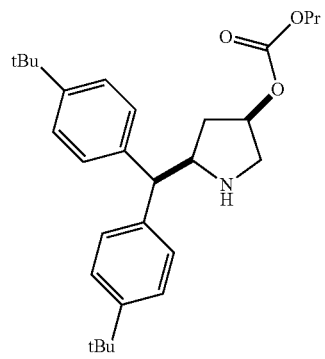
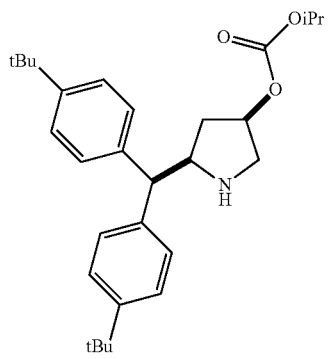

-continued
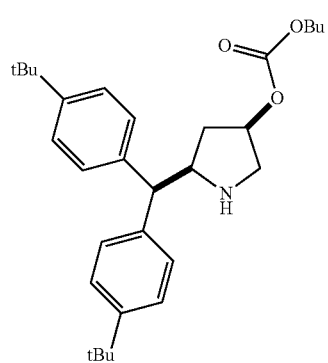 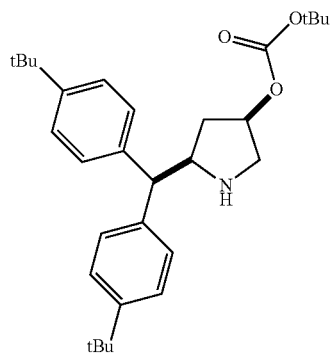
[Chem. 19]
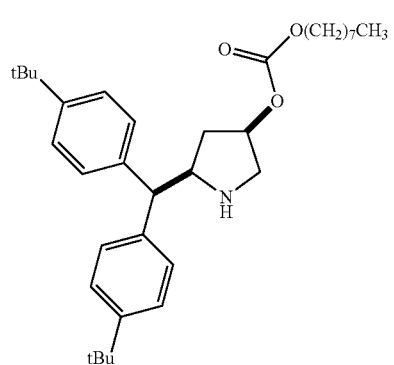 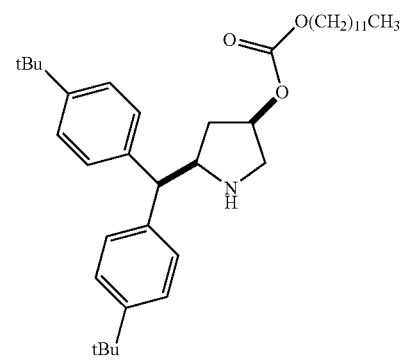 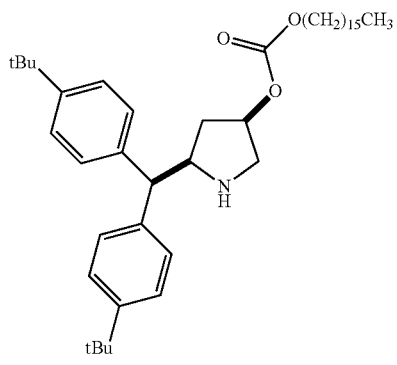
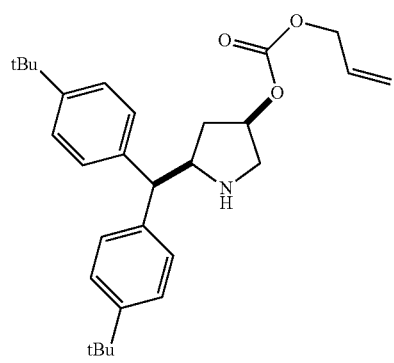 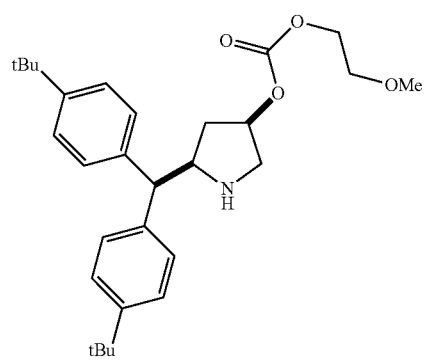
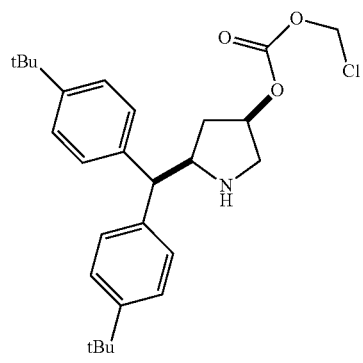 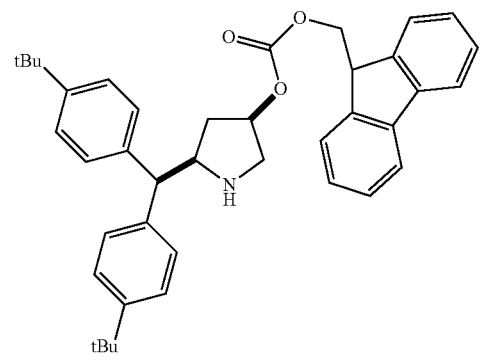

-continued
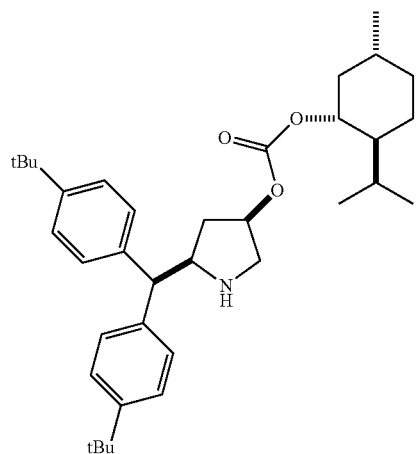
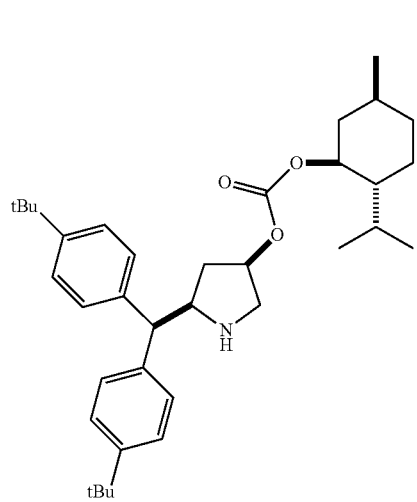
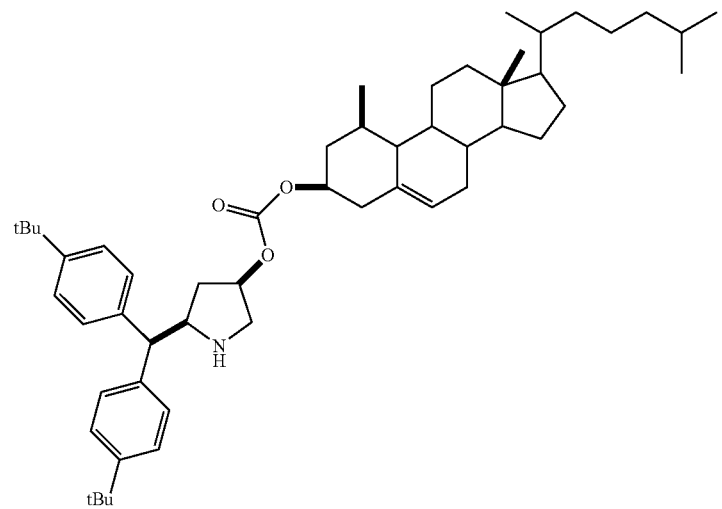
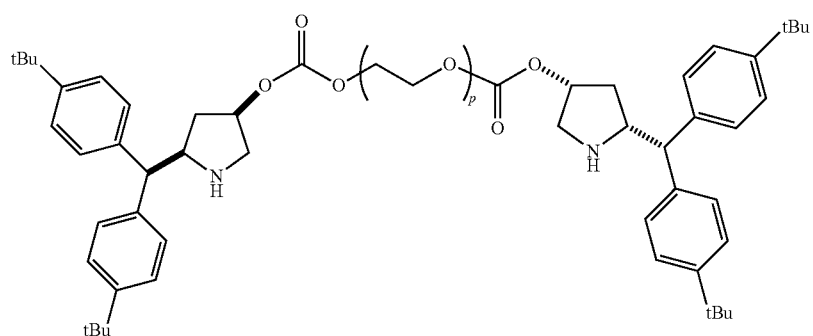
[Chem. 20]
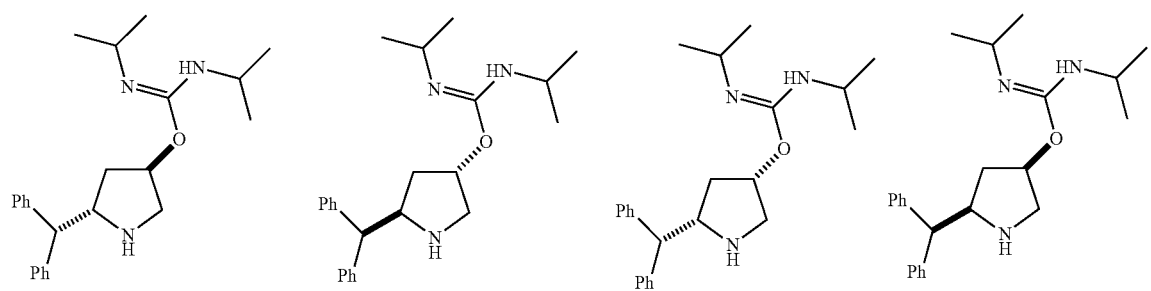

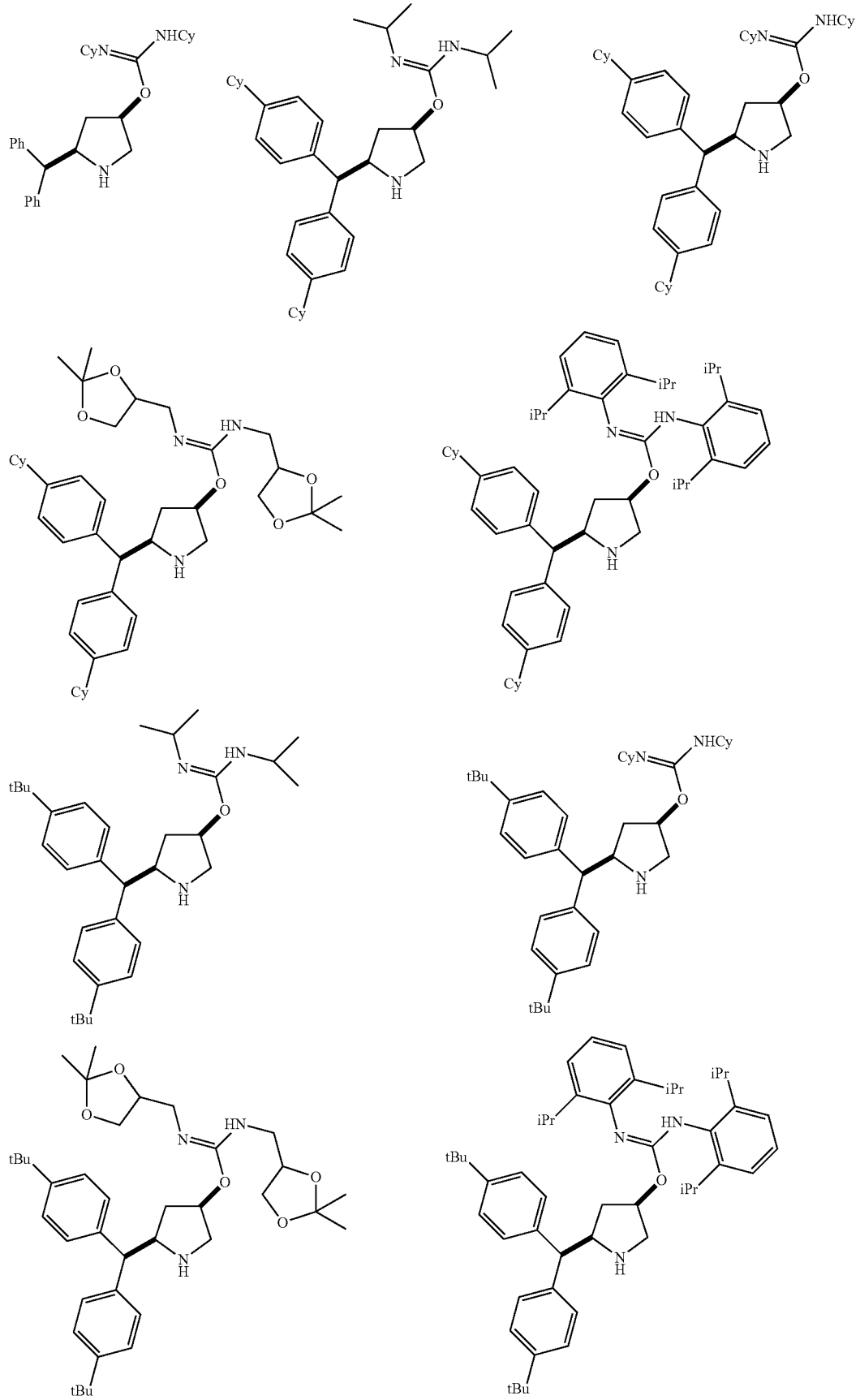

-continued
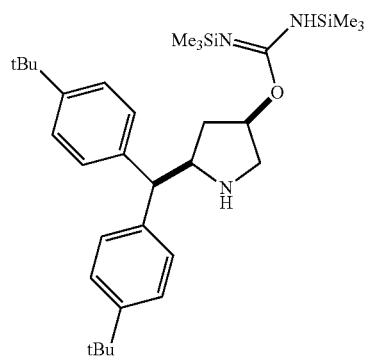
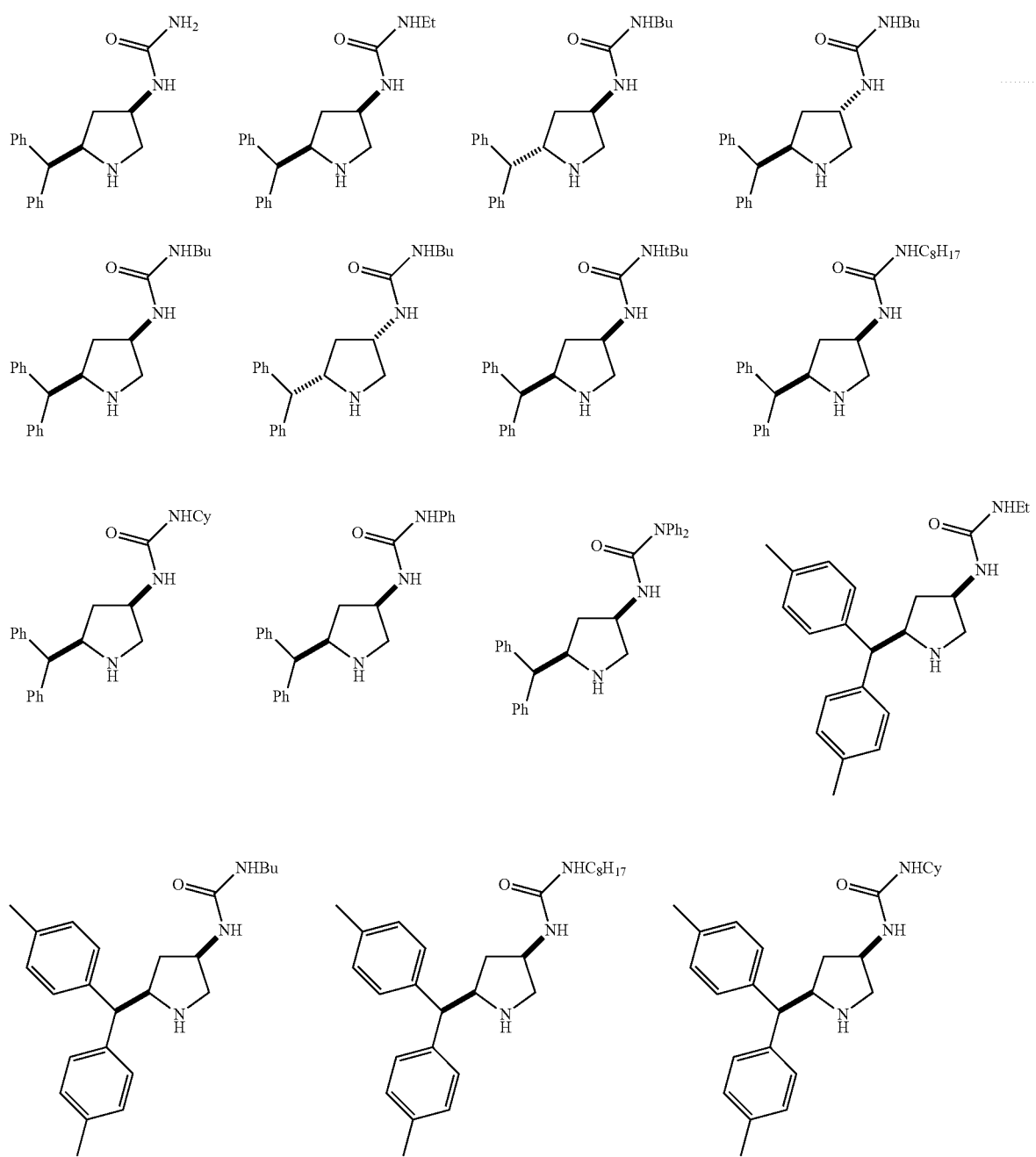

-continued
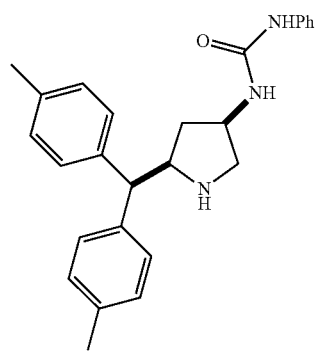 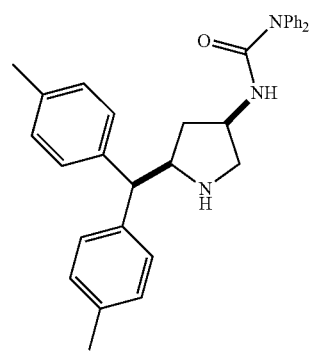 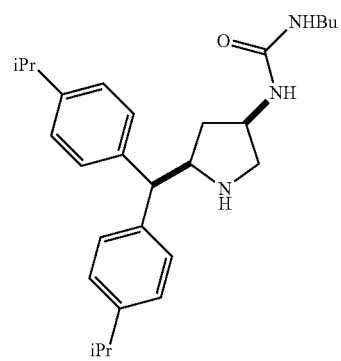
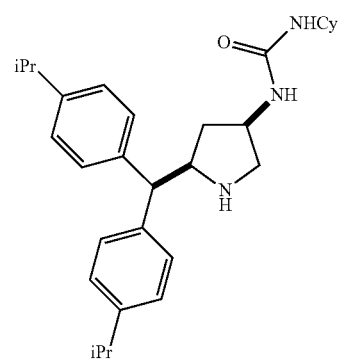 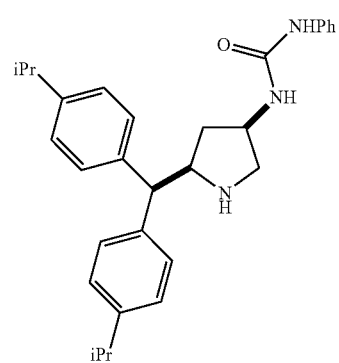 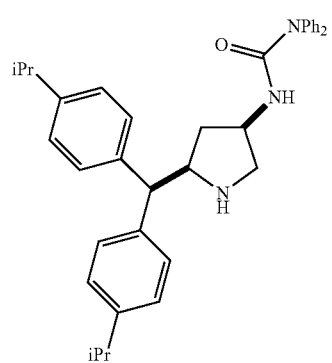
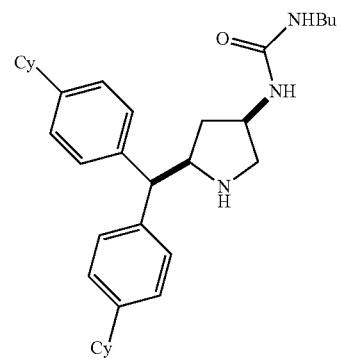 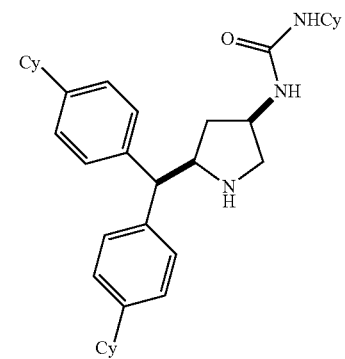 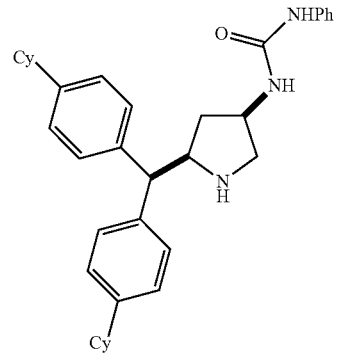
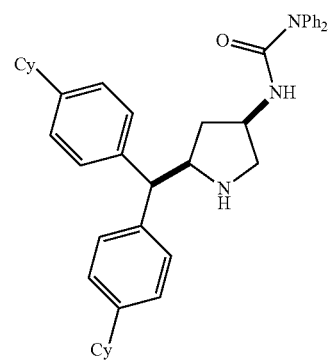

-continued
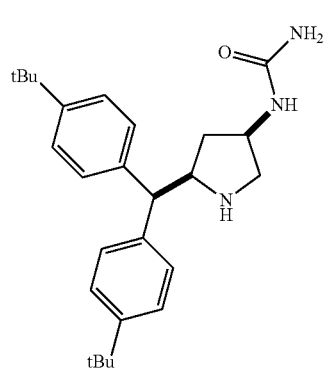 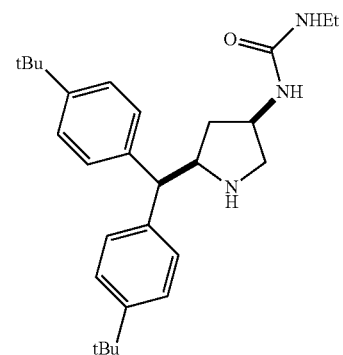 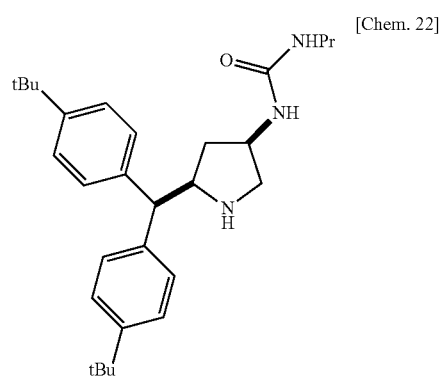
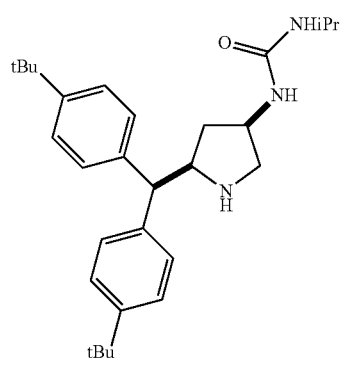 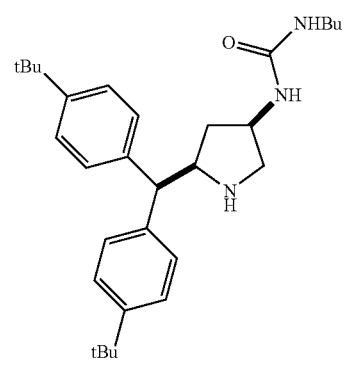 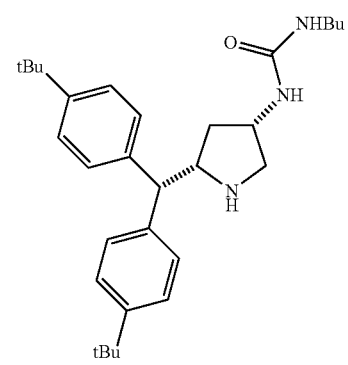
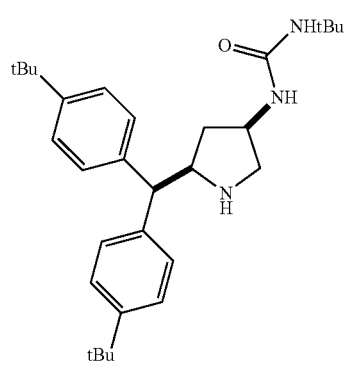 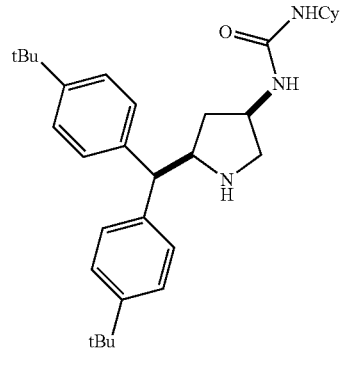 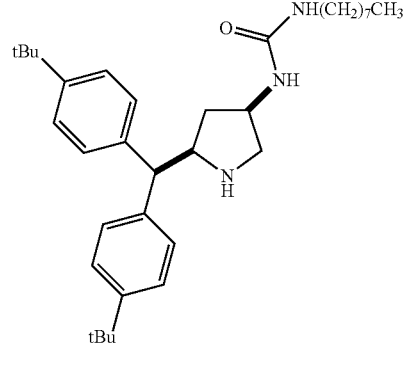
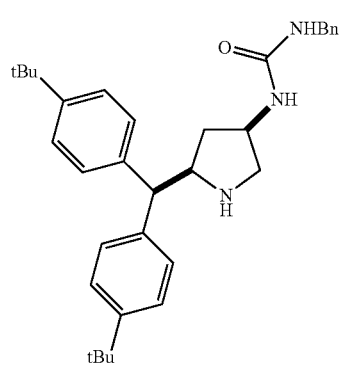 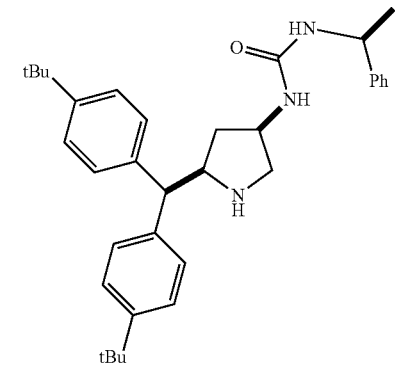 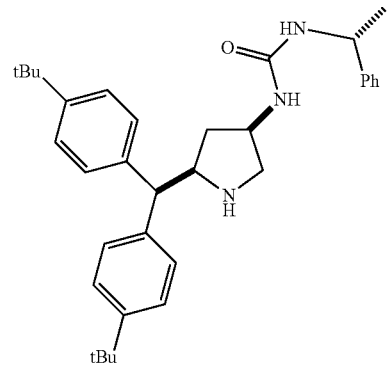

-continued
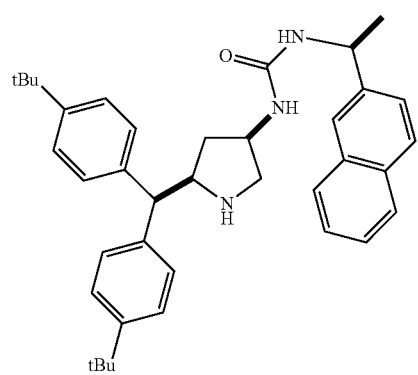
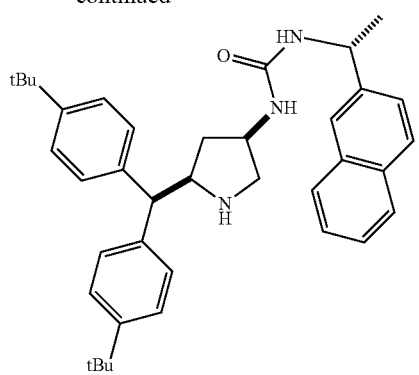
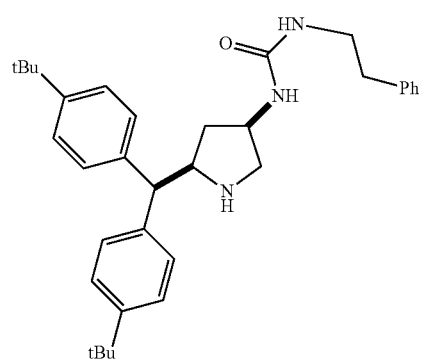
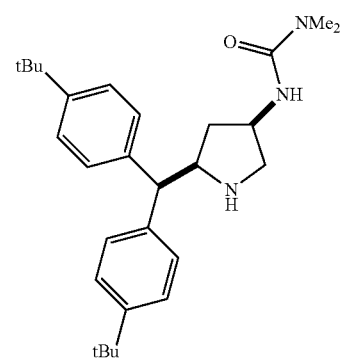
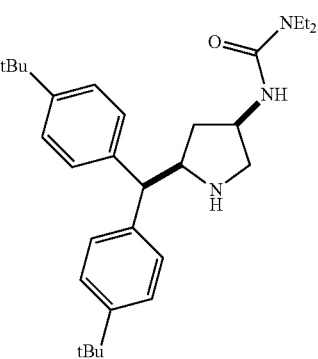
[Chem. 23]
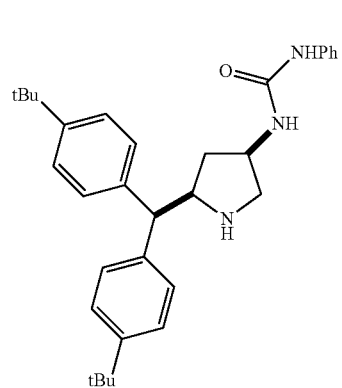
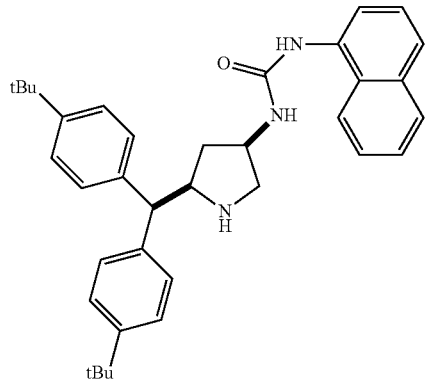
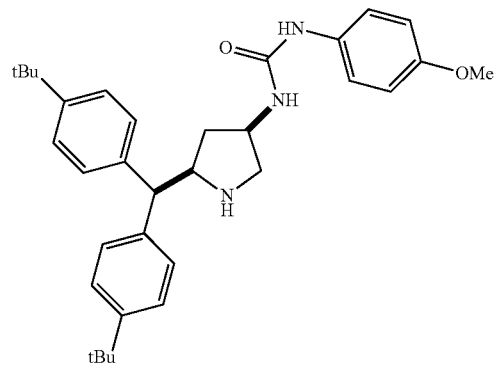
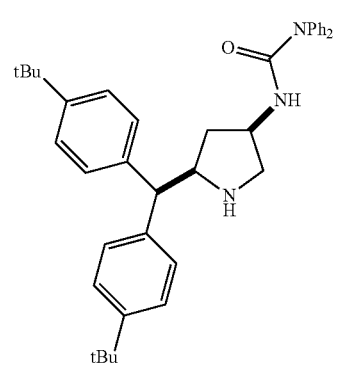

-continued
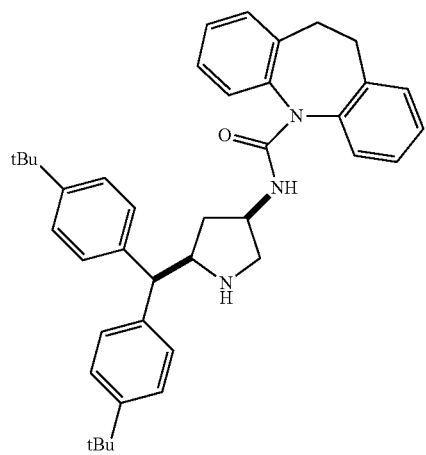
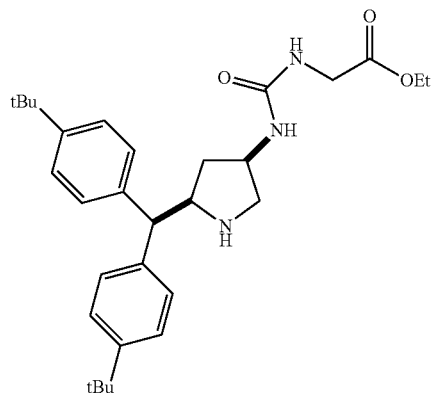
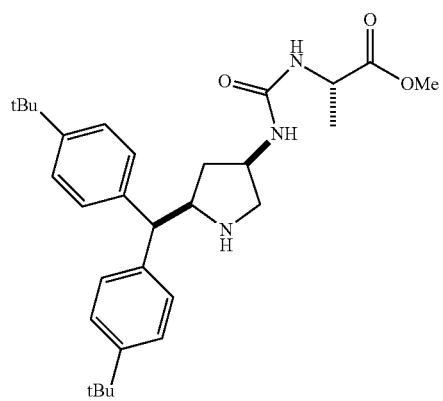
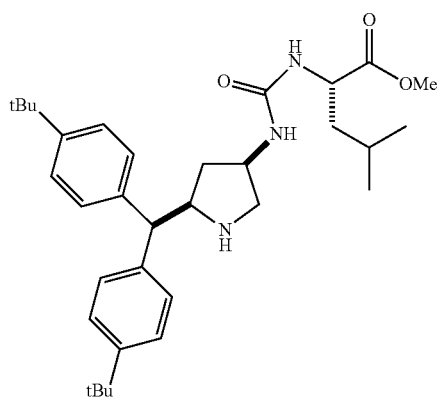
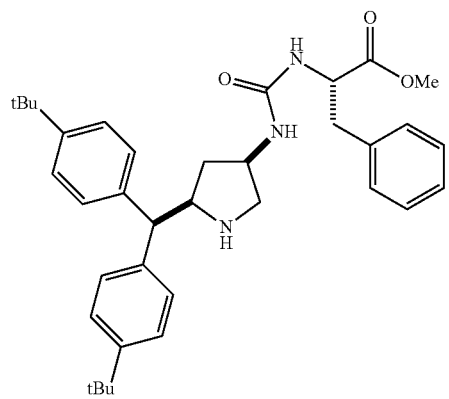
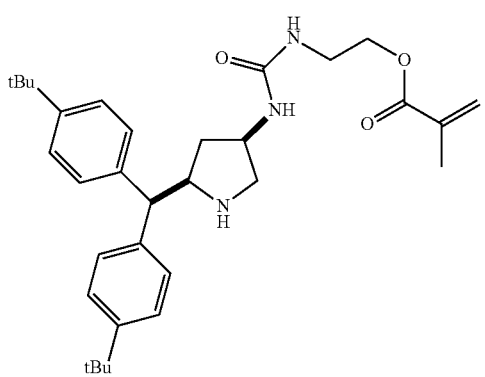
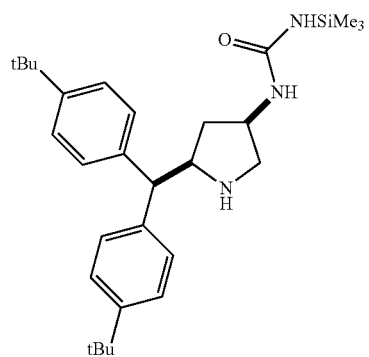

[Chem. 24]
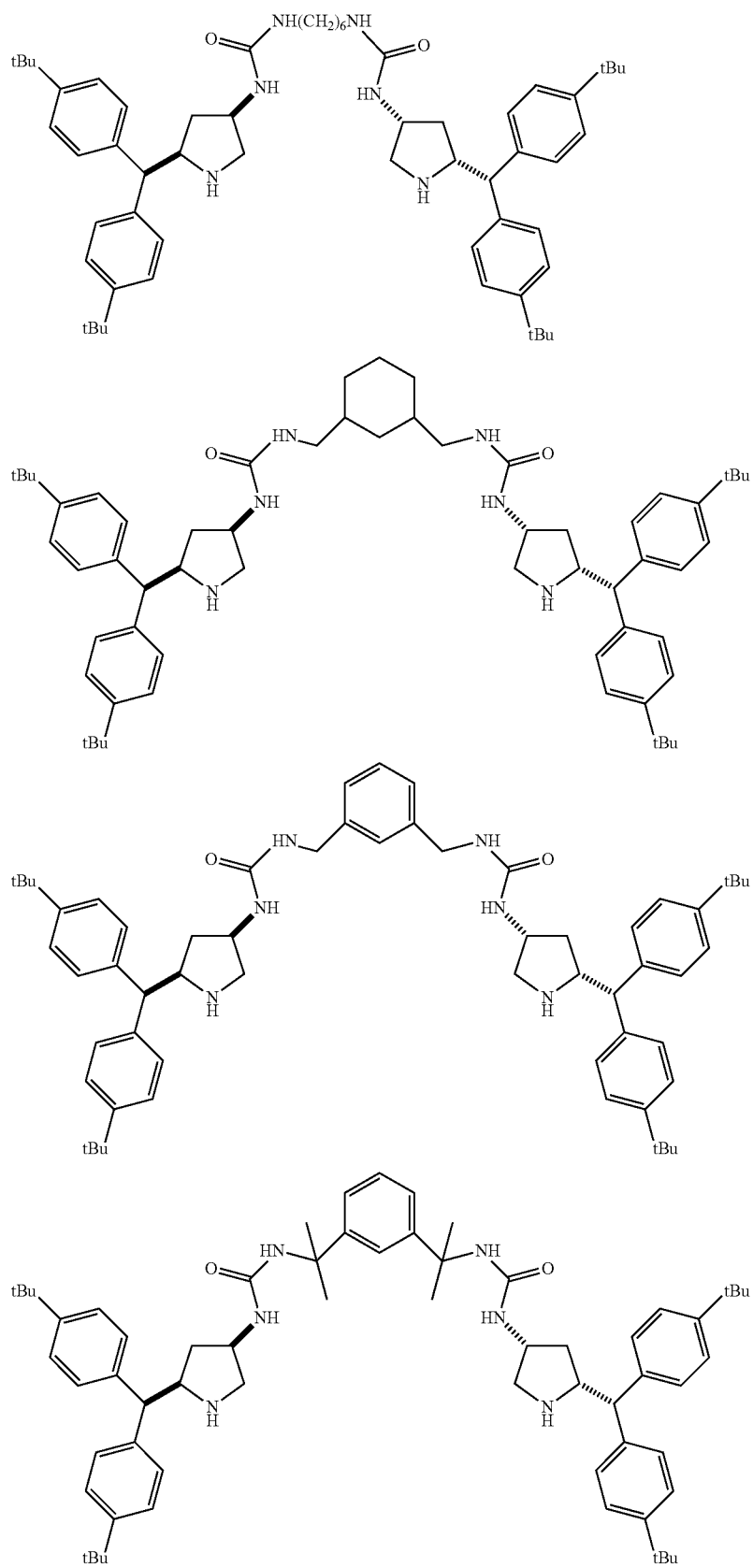

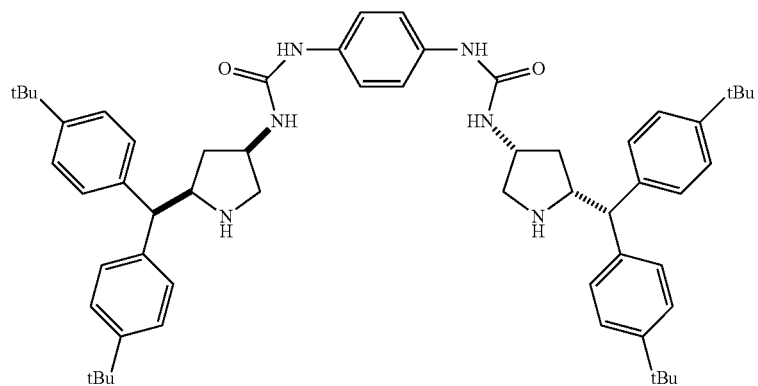
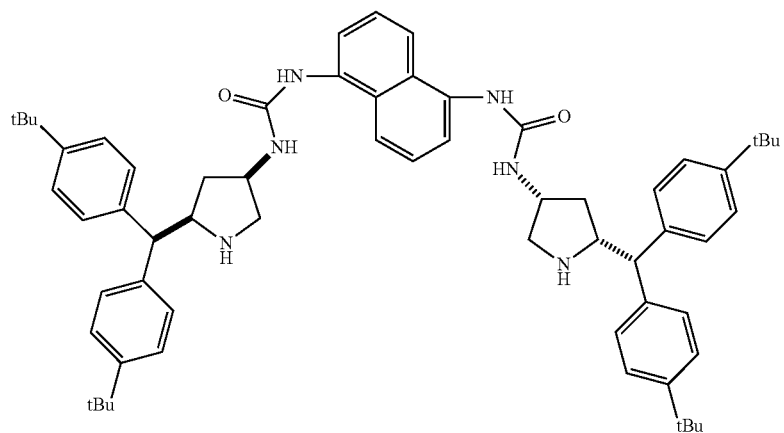
[Chem. 25]
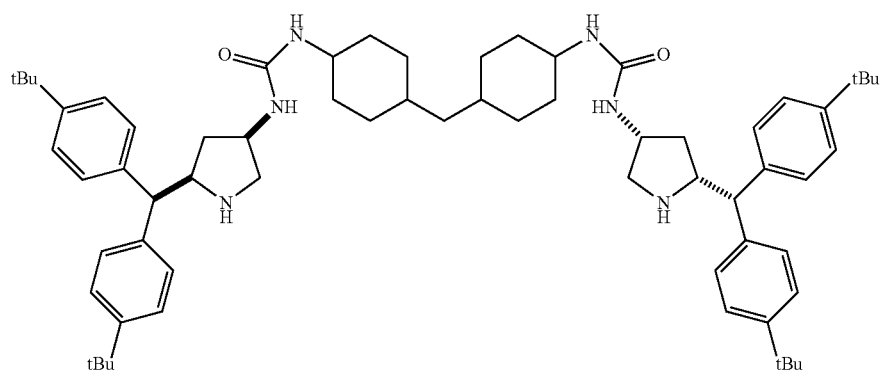
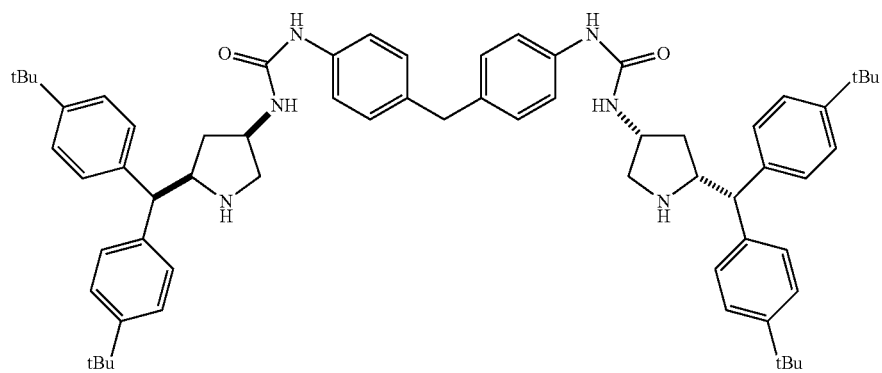

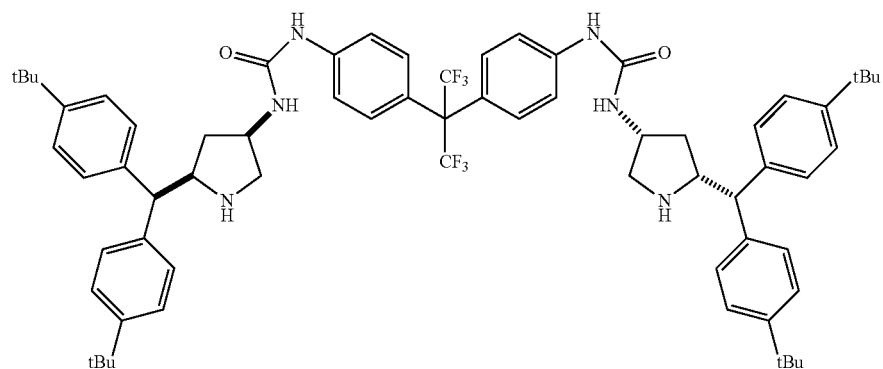
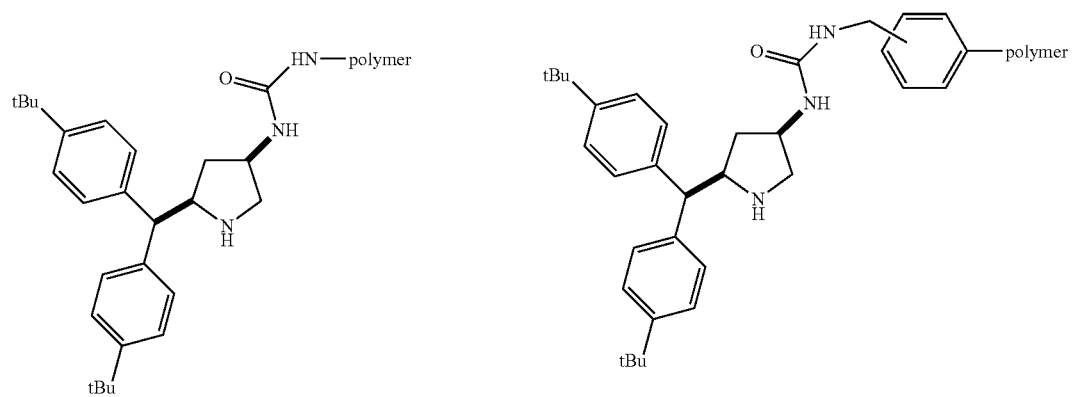
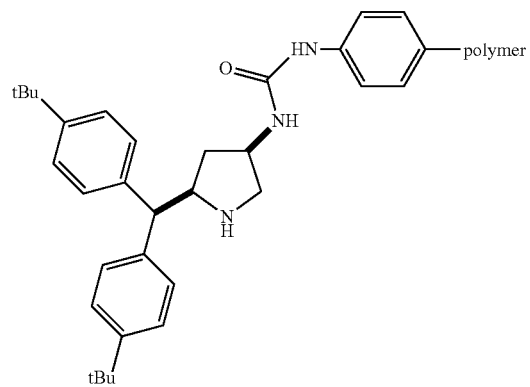
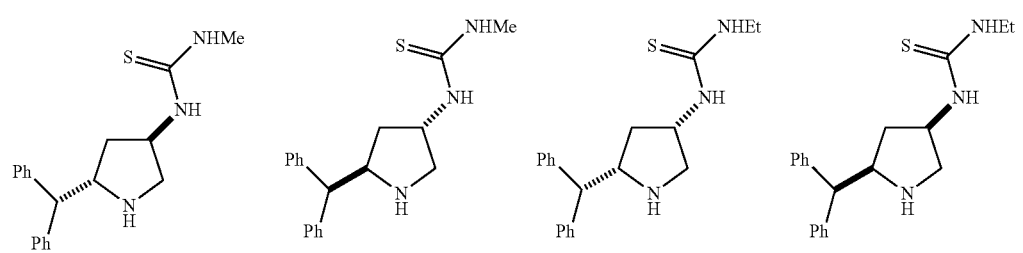
[Chem. 26]

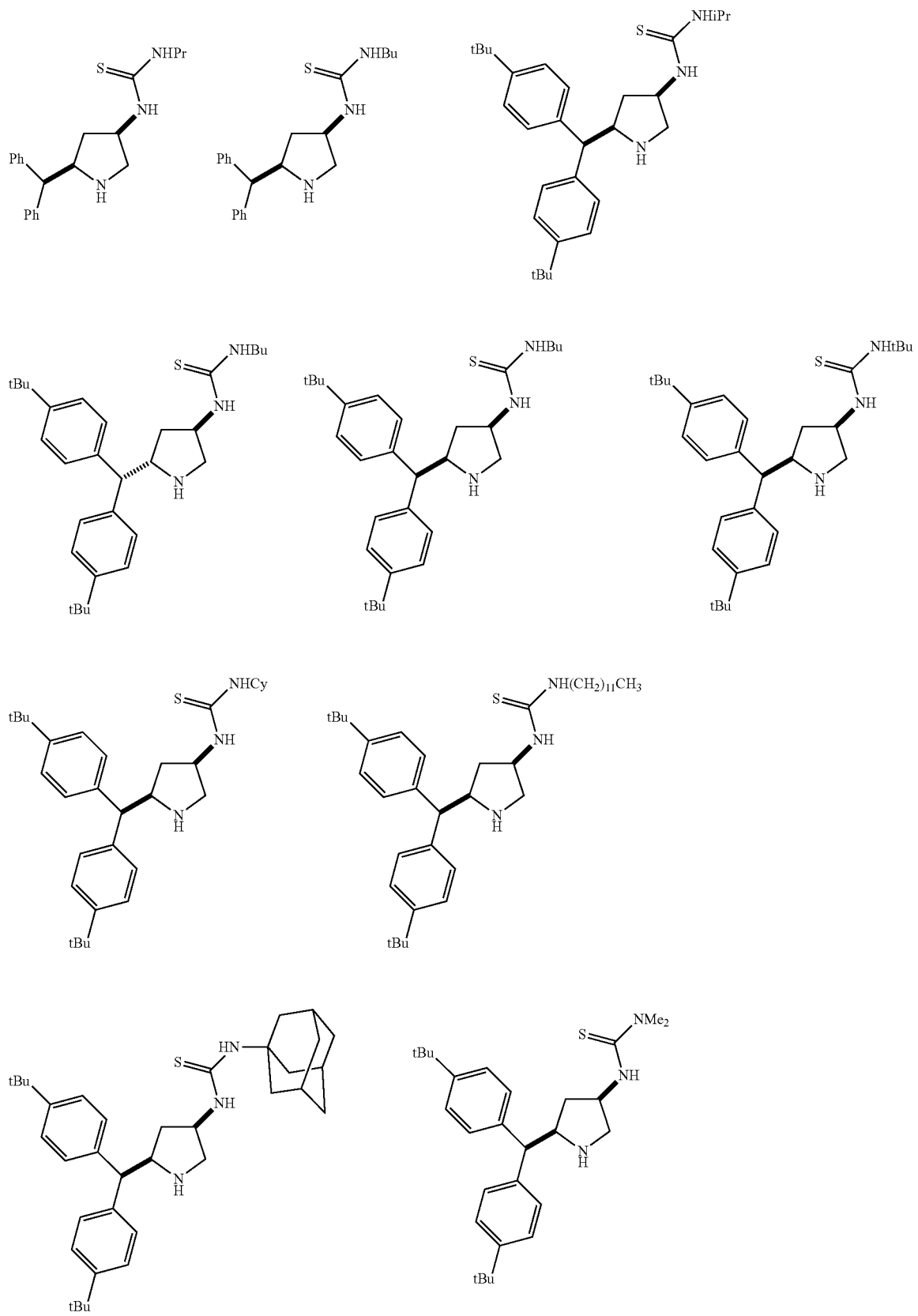

75 76
-continued
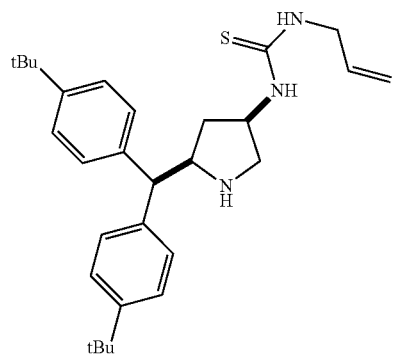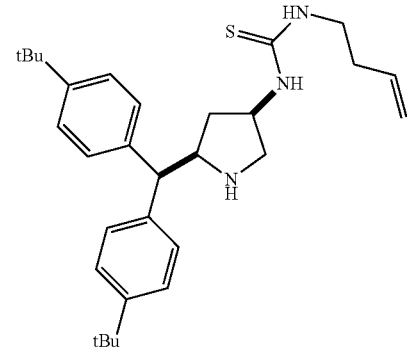
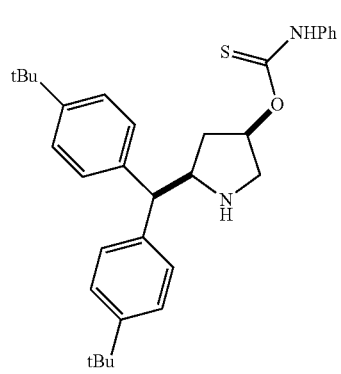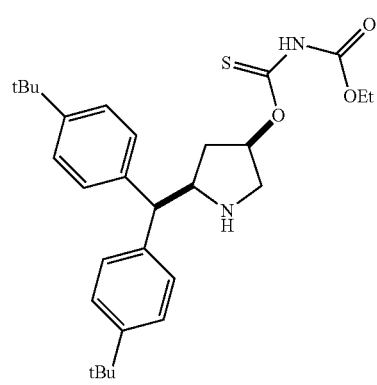
[Chem. 27]
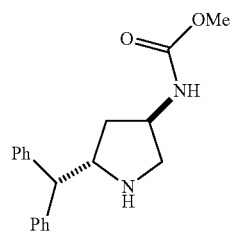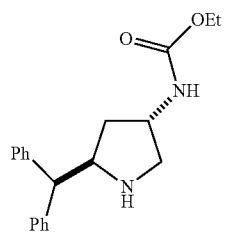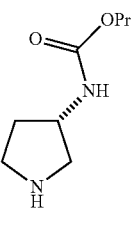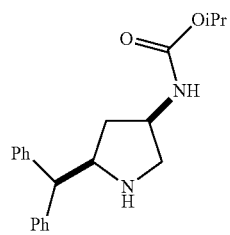
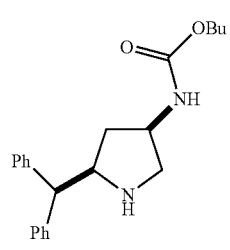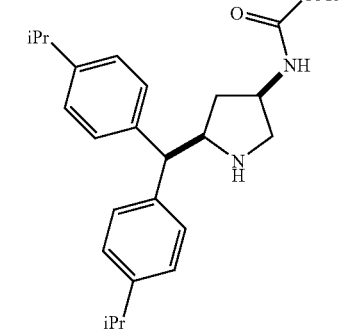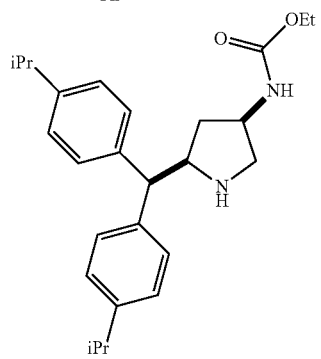
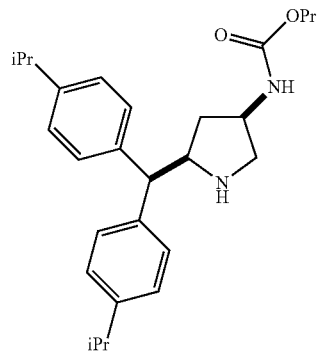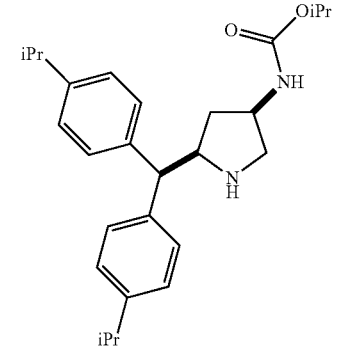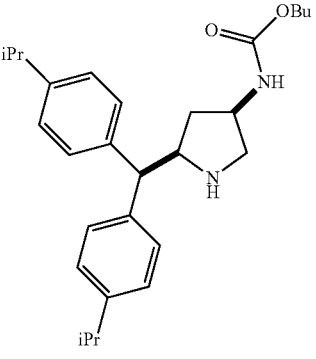

-continued
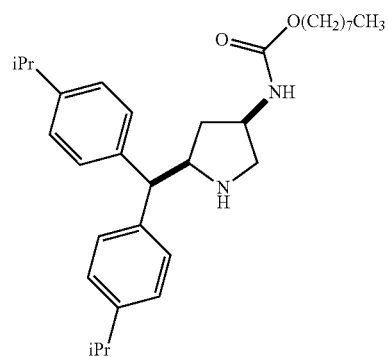
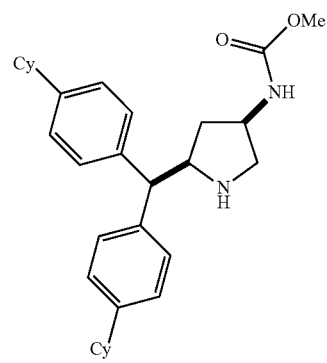
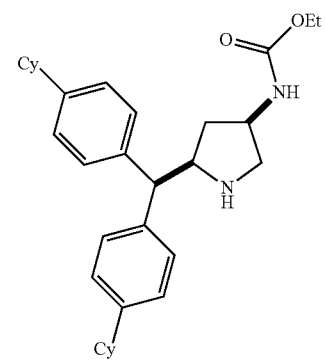
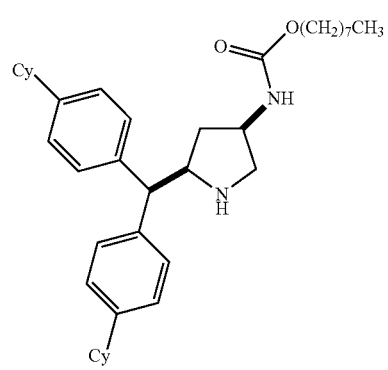
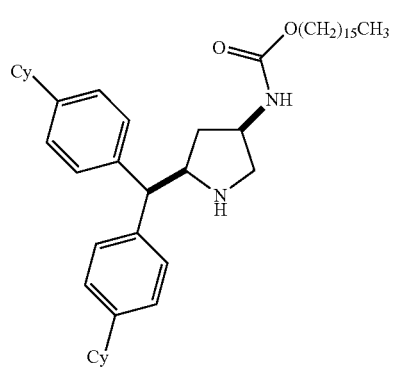
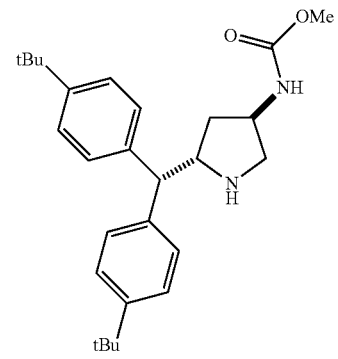
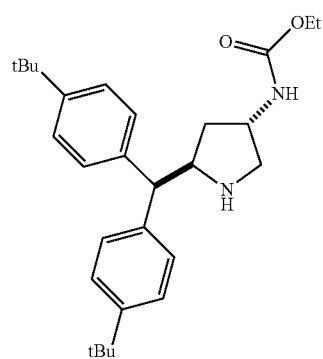
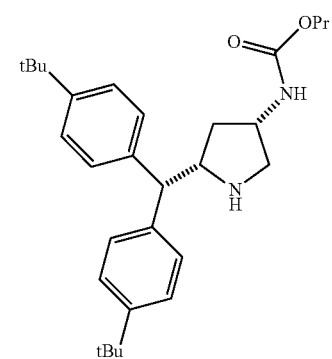
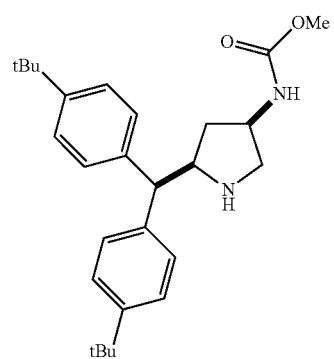
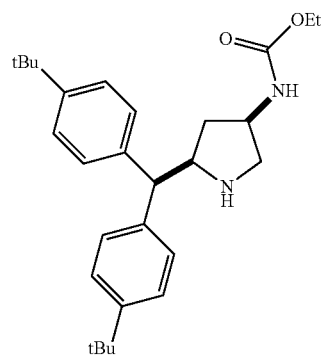
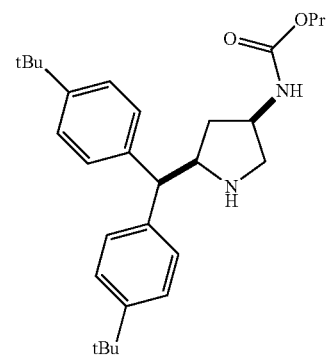

-continued
[Chem. 28]
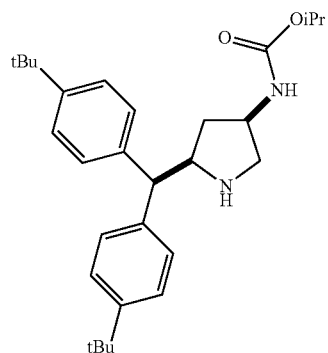 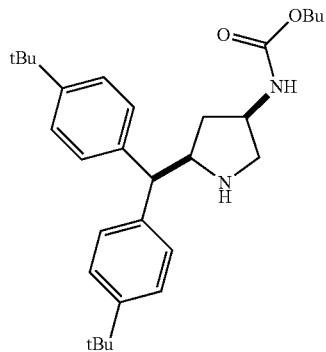 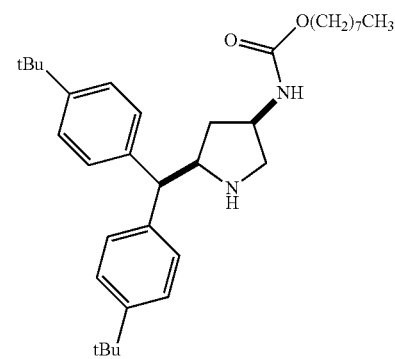
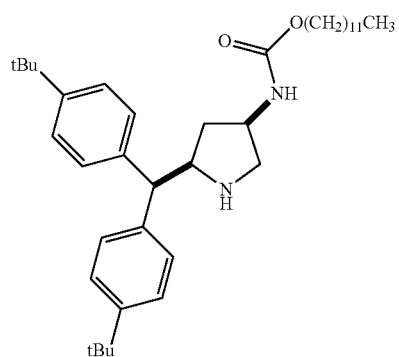 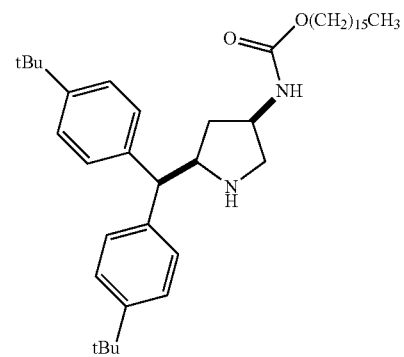
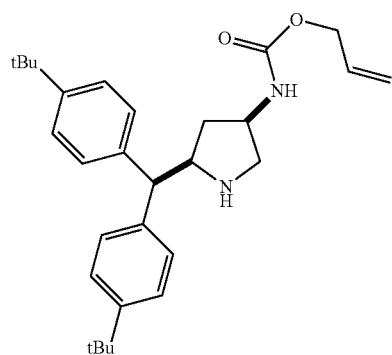 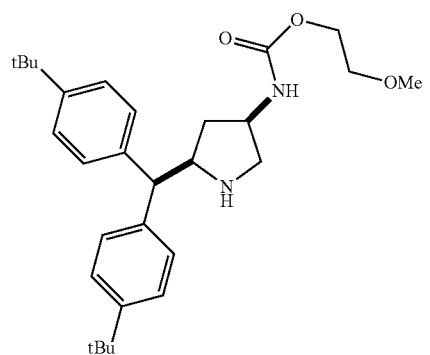
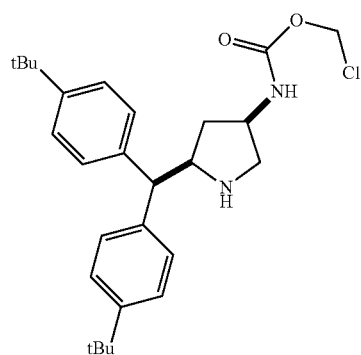 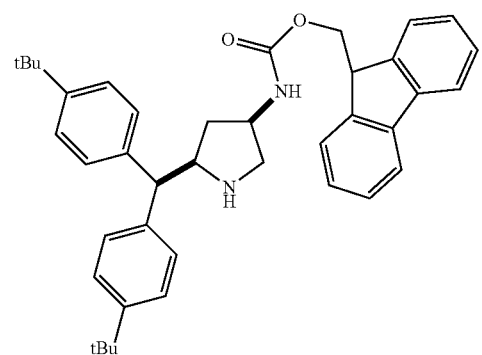

81
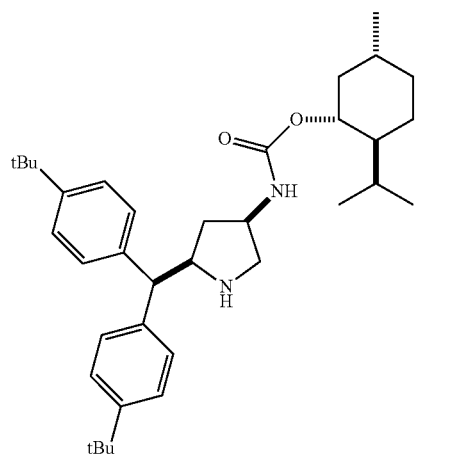
82
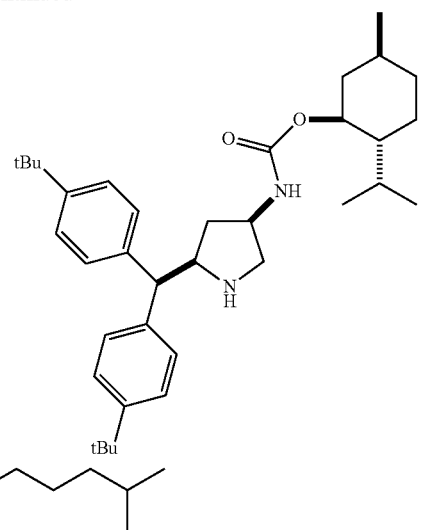
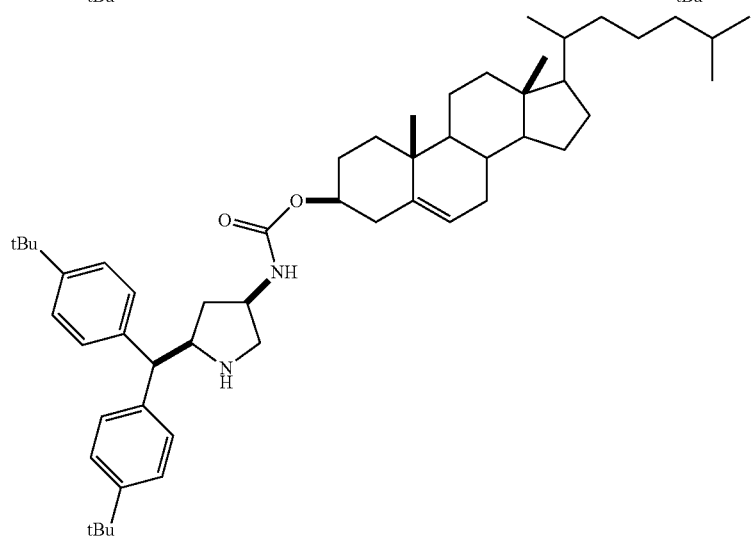
[Chem. 29]
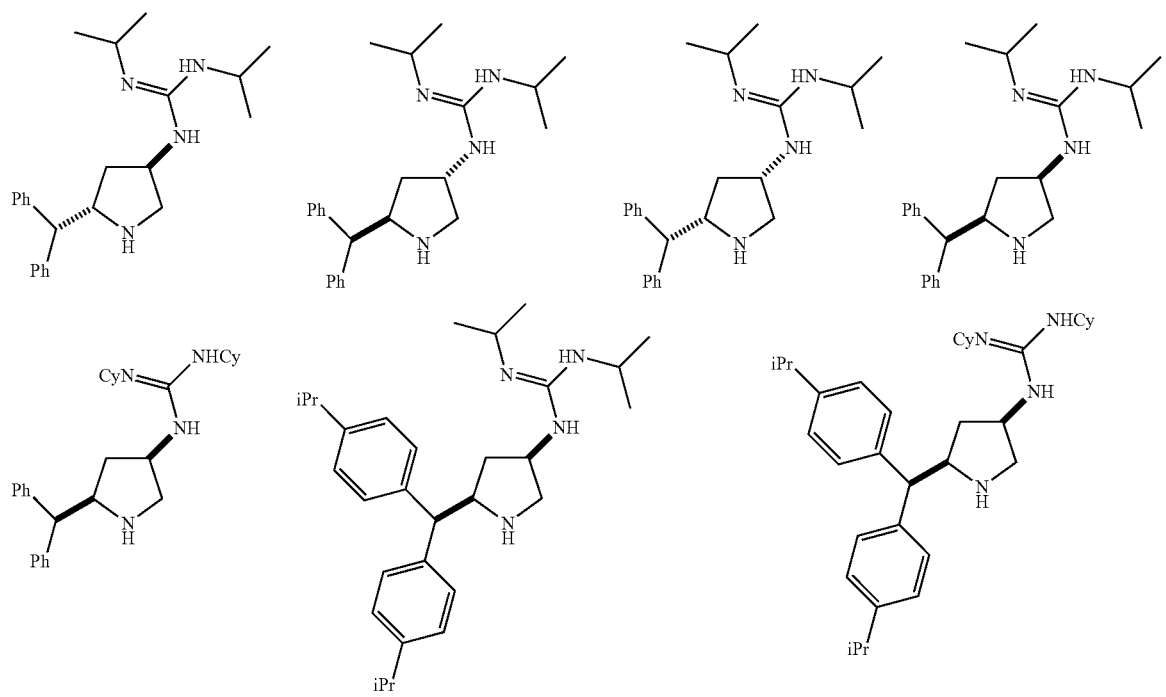

83
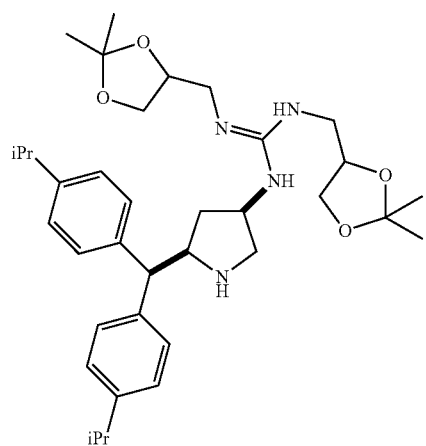
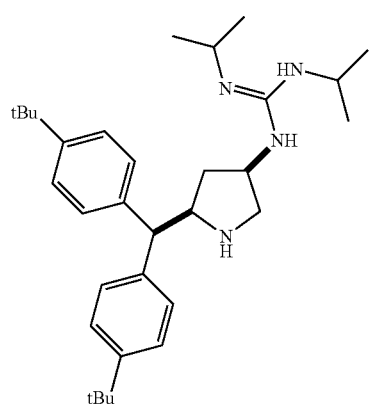
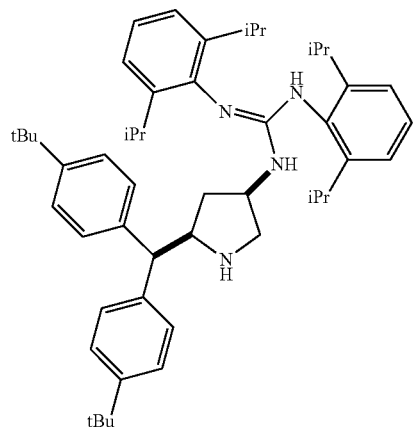
84
-continued
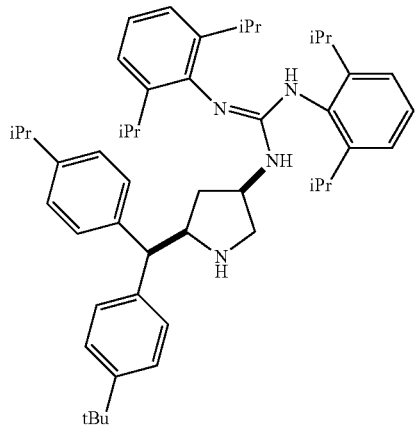
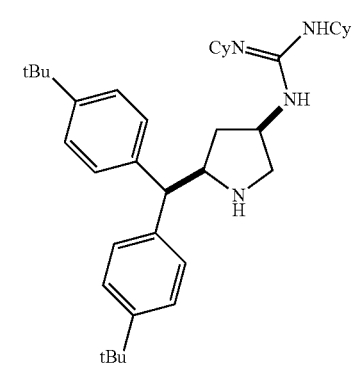
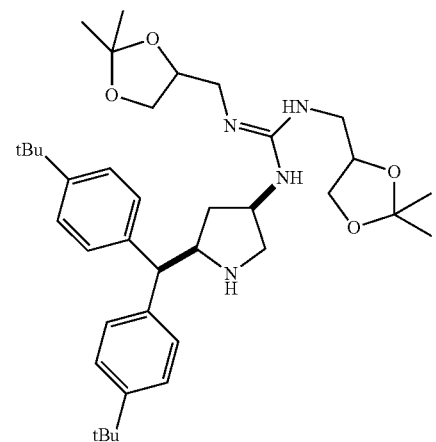
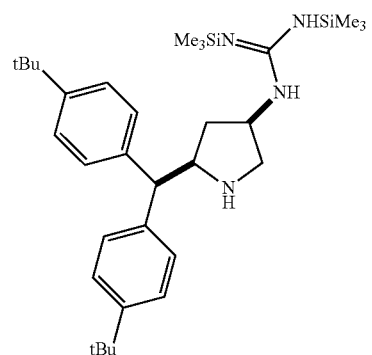
[Chem. 30]
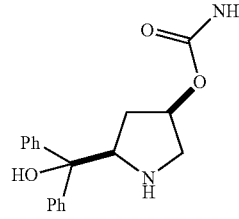
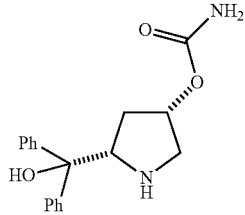
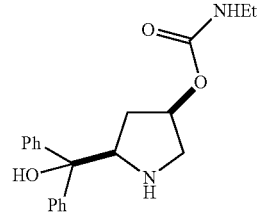
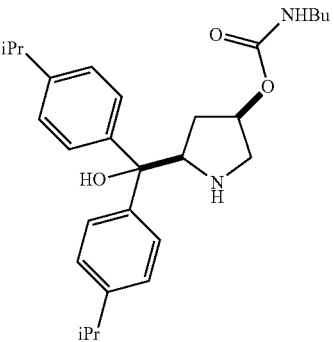

-continued
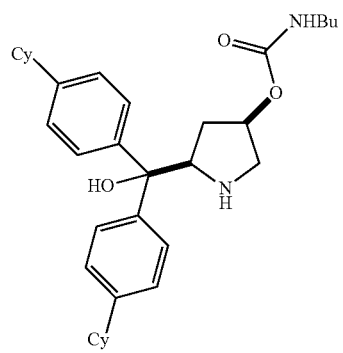 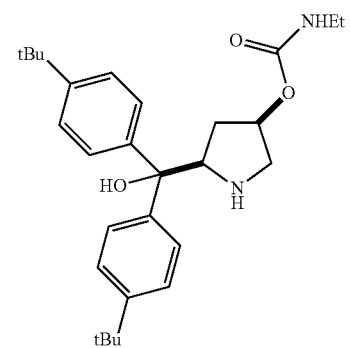 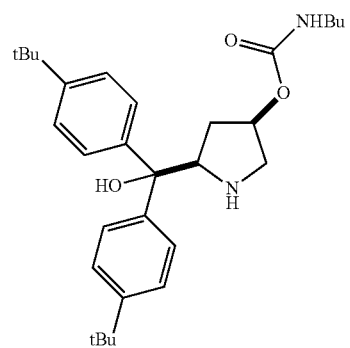
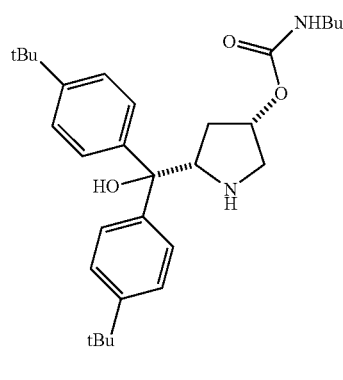 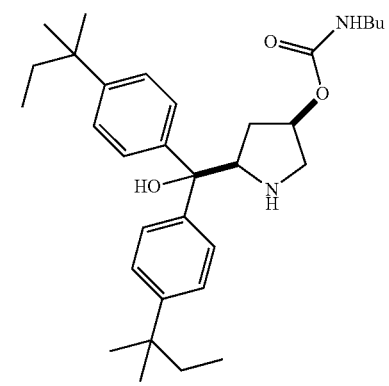 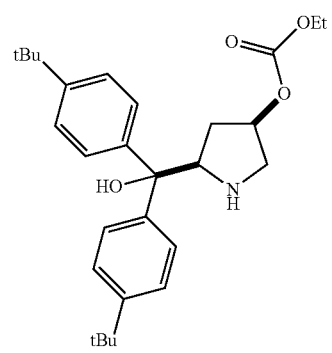
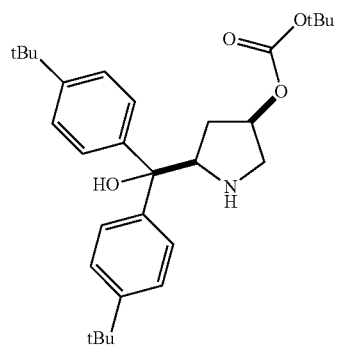 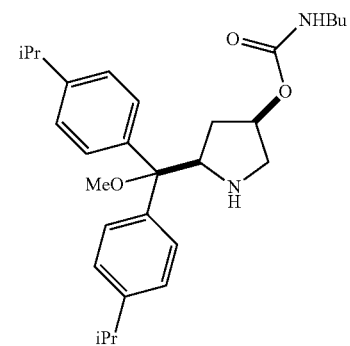 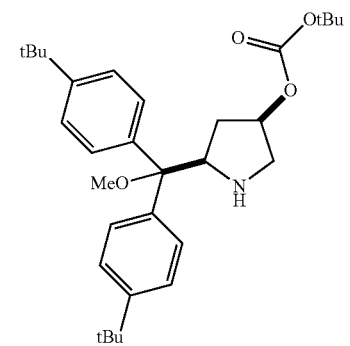
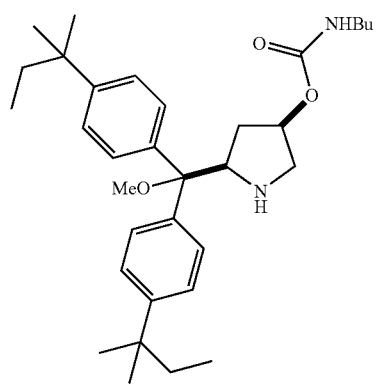 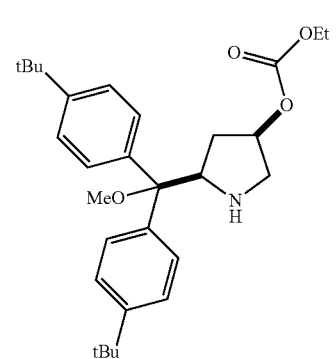 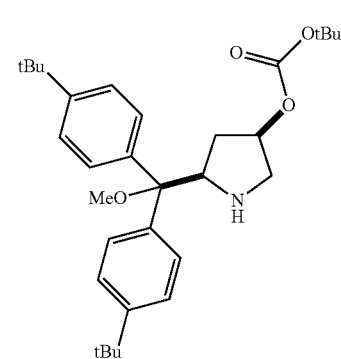

-continued
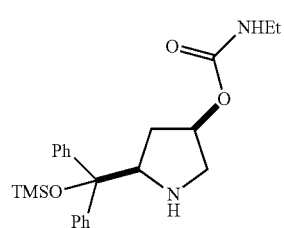 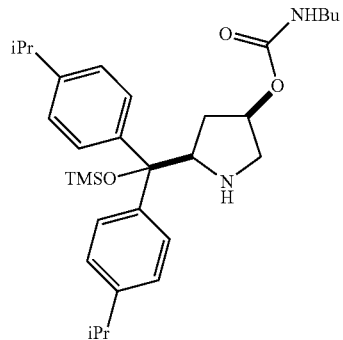 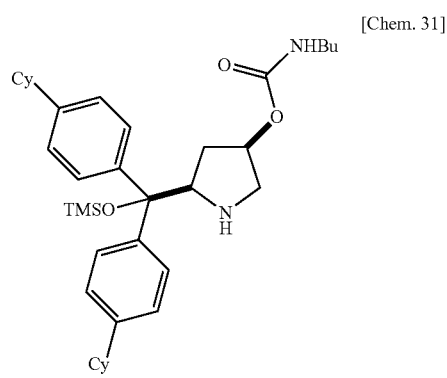
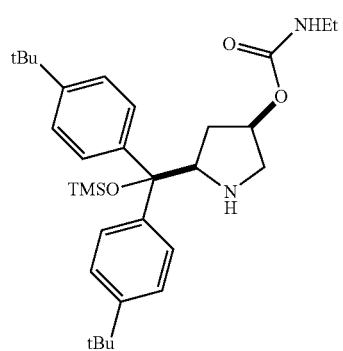 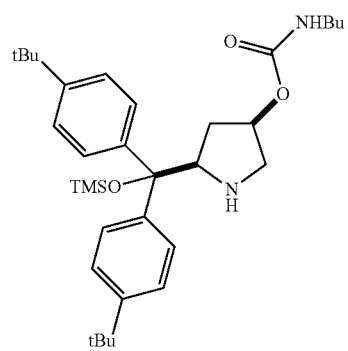 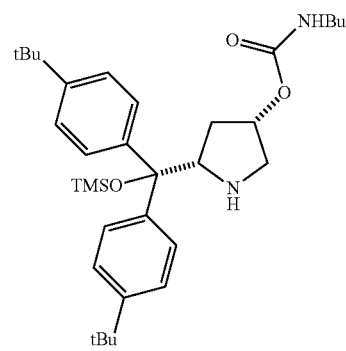
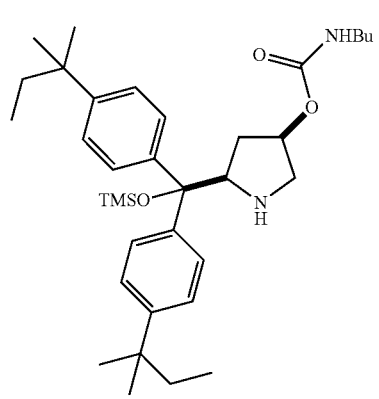 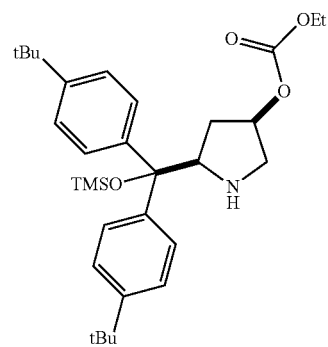 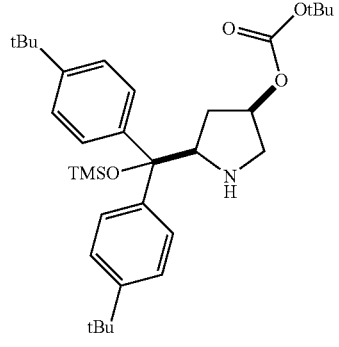
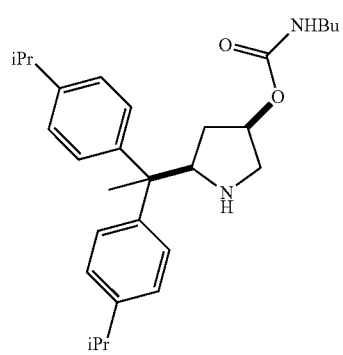 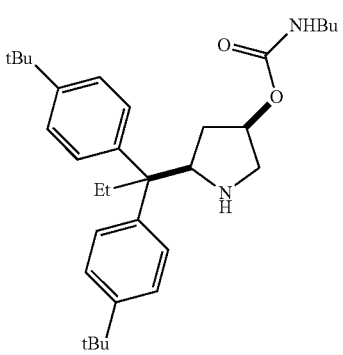 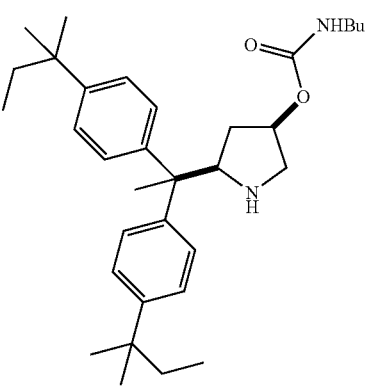

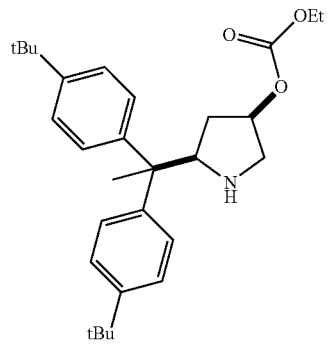
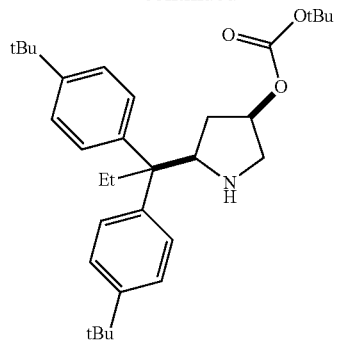
[Chem. 32]
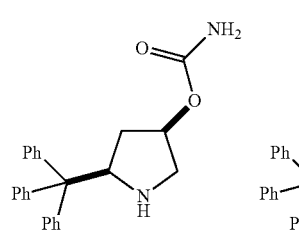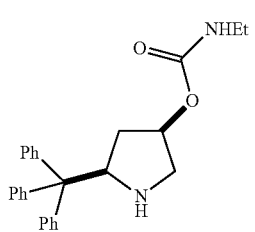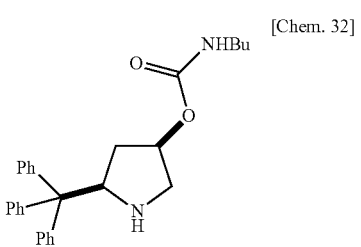
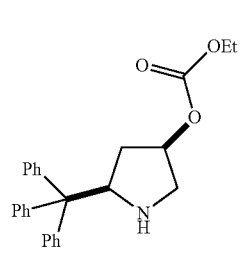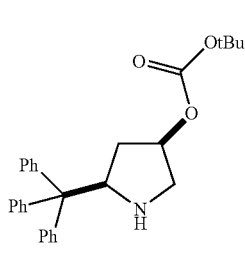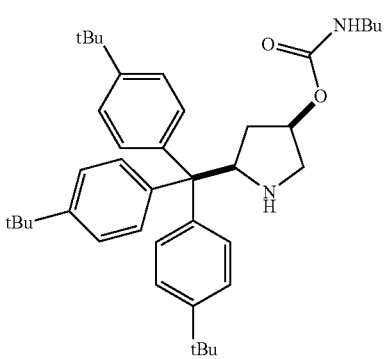
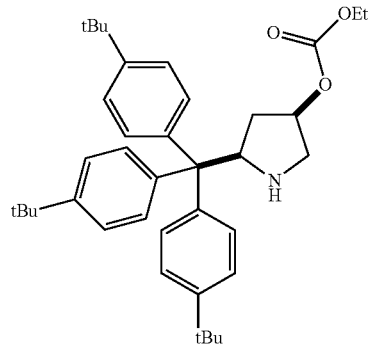
[Chem. 33]
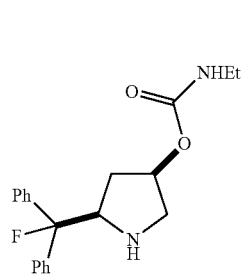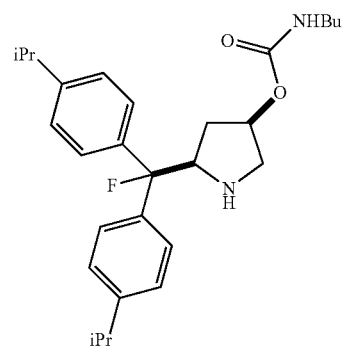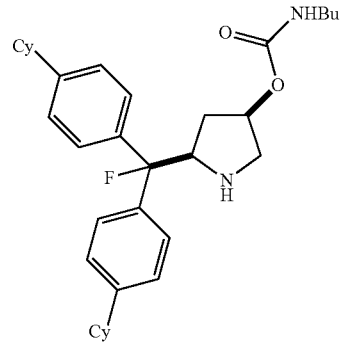

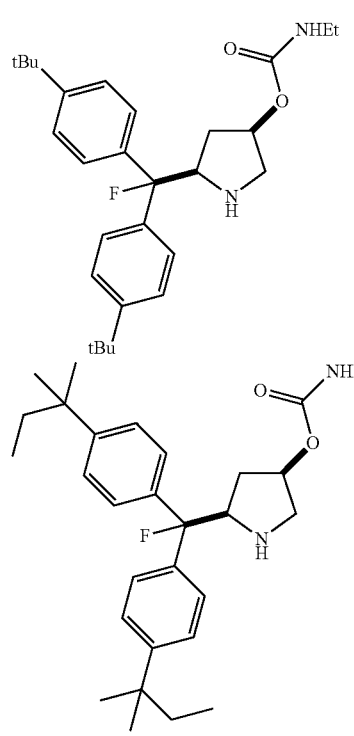
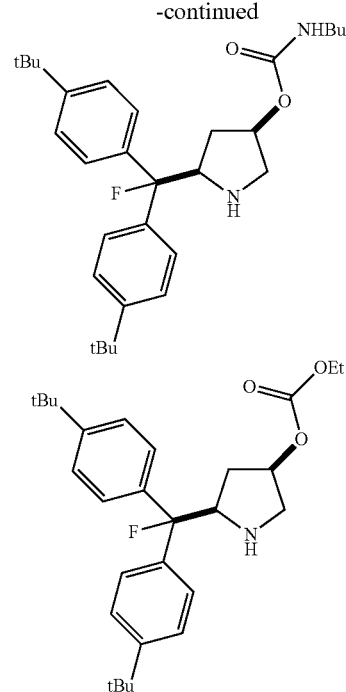
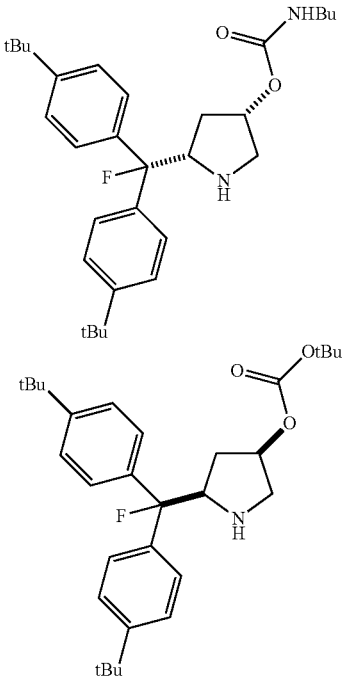

The optically active cyclic nitrogen-containing compounds which are used in the invention and represented by the general formula (1) are commercially available or can also be synthesized.

Among the optically active cyclic nitrogen-containing compounds represented by the general formula (1), a production method of optically active diarylmethylpyrrolidine compounds is described.

The optically active diarylmethylpyrrolidine compounds can be synthesized, for example, in accordance with the method described in Tetrahedron, 1993, 49, 5127-5132, and Tetrahedron: Asymmetry, 1997, 8, 149-153. The method can be shown by the following Scheme 1.

Scheme 1

[Chem. 34]

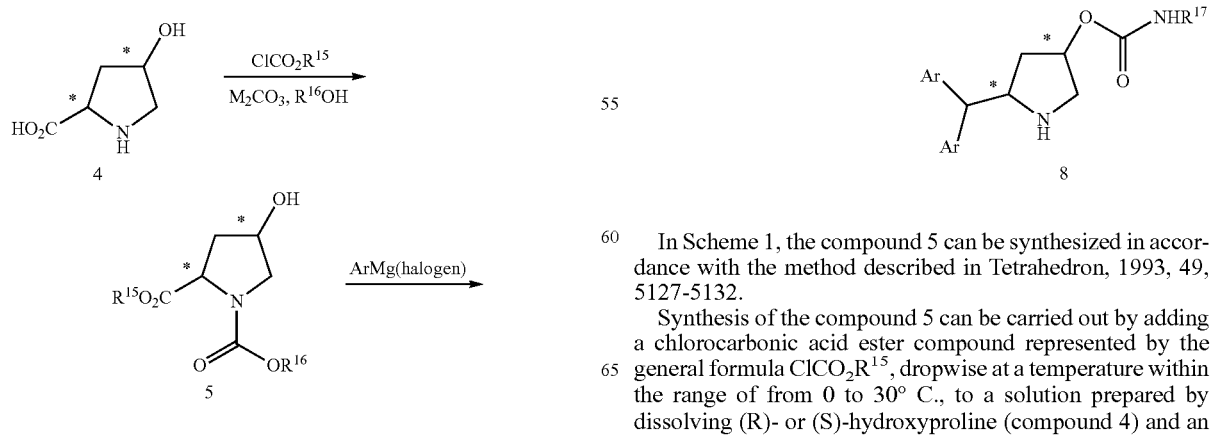

In Scheme 1, the compound 5 can be synthesized in accordance with the method described in Tetrahedron, 1993, 49, 5127-5132.

Synthesis of the compound 5 can be carried out by adding a chlorocarbonic acid ester compound represented by the general formula $ClCO_2R^{15}$, dropwise at a temperature within the range of from 0 to 30° C., to a solution prepared by dissolving (R)- or (S)-hydroxyproline (compound 4) and an alkali metal compound represented by the general formula $M_2CO_3$ in an alcohol compound represented by the general formula $R^{16}OH$. The amount of the solvent used is, for example, from 1 to 30 times volume (ml) [ml/g], preferably from 5 to 20 times volume (ml) [ml/g], based on the weight (g) of (R)- or (S)-hydroxyproline as the substrate.

The compound 5 obtained as described above can be isolated and purified by generally used operations such as extraction, recrystallization, various types of chromatography and the like.

As the group represented by $R^{15}$ in the chlorocarbonic acid ester compound represented by the general formula $ClCO_2R^{15}$, examples thereof include alkyl groups having from 1 to 8 carbon atoms such as methyl group, ethyl group, propyl group, isopropyl group, butyl group, pentyl group, hexyl group, heptyl group and octyl group; cyclic alkyl groups having from 1 to 8 carbon atoms such as cyclopropyl group, cyclobutyl group, cyclopentyl group, cycloheptyl group and cyclooctyl group; aralkyl groups having from 7 to 10 carbon atoms such as benzyl group and p-methylbenzyl group.

As the metal represented by M in the alkali metal compound represented by the general formula $M_2CO_3$, lithium, sodium, potassium, and cesium can be mentioned.

As the group represented by $R^{16}$ in the alcohol compound represented by the general formula $R^{16}OH$, the alkyl groups enumerated in the description of $R^1$ to $R^{10}$ of the optically active cyclic nitrogen-containing compound represented by the general formula (1) can be mentioned.

The compound 6 can be synthesized in accordance with the method described in Tetrahedron: Asymmetry, 1997, 8, 149-153.

Synthesis of the compound 6 is carried out by adding an ether solution, such as a tetrahydrofuran (THF), of a Grignard compound represented by the general formula ArMg(halogen) dropwise to an ether solution, such as a THF, of the compound 5, under an atmosphere of an inert gas at a temperature of from −5 to 20° C., and rising the reaction temperature finally to about 70° C. and keeping it for a period of from 3 to 6 hours. The amount of the solvent used is, for example, from 1 to 40 times volume (ml) [ml/g], preferably from 5 to 25 times volume (ml) [ml/g], based on the weight (g) of the compound 5 as the substrate.

The compound 6 obtained as described above can be isolated and purified by generally used operations such as extraction, recrystallization, various types of chromatography and the like.

As the aryl group represented by Ar in the Grignard compound represented by the general formula ArMg(halogen), an aryl group having, for example, from 6 to 20 carbon atoms, which may have a substituent group, can be mentioned.

As illustrative examples of the aryl group, the aryl groups enumerated in the description of $R^1$ to $R^{10}$ of the optically active cyclic nitrogen-containing compound represented by the general formula (1) can be mentioned.

As illustrative examples of the substituent group substituting the aryl group, the groups described in the description on the substituent group of alkyl group enumerated in the description of $R^1$ to $R^{10}$ of the optically active cyclic nitrogen-containing compound represented by the general formula (1) can be mentioned.

As the aryl group, examples thereof include phenyl group, tolyl group, isopropylphenyl group, xylyl group, t-butylphenyl group, cyclohexyl group, 1-methylcyclohexyl group, adamantylphenyl group, trifluoromethylphenyl group, naphthyl group, anthryl group, phenanthryl group, biphenyl group, and 4-(2'-p-tolylpropyl)phenyl group.

As the halogen atom represented by halogen in the Grignard compound represented by the general formula ArMg (halogen), for example, chlorine, bromine and iodine can be mentioned.

The compound 7 can be easily synthesized by a general method, e.g., a method for adding the compound 6 to isocyanates represented by $R^{17}NCO$.

Synthesis of the compound 7 is carried out by adding an isocyanate compound represented by the general formula $R^{17}NCO$ dropwise to a polar aprotic solution such as N,N-dimethylformamide (DMF) of the compound 6 in the presence of a lewis acid catalyst such as copper(I) chloride under an atmosphere of an inert gas at about a room temperature, and mixing it for a period of from 1 to 24 hours. The amount of the solvent used is, for example, from 1 to 20 times volume (ml) [ml/g], preferably from 3 to 10 times volume (ml) [ml/g], based on the weight (g) of the compound 6 as the substrate.

The compound 7 obtained as described above can be isolated and purified by generally used operations such as extraction, recrystallization, various types of chromatography and the like.

As the substituent group represented by $R^{17}$ in the isocyanate compound represented by the general formula $R^{17}NCO$, for example, the substituent groups enumerated in the description of $R^1$ to $R^{10}$ of the optically active cyclic nitrogen-containing compound represented by the general formula (1) or polymer chain can be mentioned.

As the substituent group, examples thereof include an alkyl group, a cycloalkyl group, an alkenyl group, an aryl group, an aralkyl group, a carboxyl group, an alkoxycarbonyl group, an amido group, an aromatic heterocyclic group, and an aliphatic heterocyclic group. Each of these groups may have a substituent group.

The optically active diarylmethylpyrrolidine compound represented by the compound 8 can be synthesized in accordance with the method described in Tetrahedron: Asymmetry, 1997, 8, 149-153.

Synthesis of the compound 8 is carried out by debenzylating the compound 7 at a temperature of from 20 to 80° C. for a period of from 1 day to 10 days in a hydrogen atmosphere of approximately from 0.1 MPa to 1 MPa, in the alcohol solvent represented by $R^{16}OH$, THF or a mixed solvent thereof in the presence of a palladium catalyst in an amount of from 0.1 to 40% by weight based on the compound 7. The amount of the solvent used is, for example, from 1 to 50 times volume (ml) [ml/g], preferably from 5 to 40 times volume (ml) [ml/g], based on the weight (g) of the compound 7 as the substrate.

The optically active diarylmethylpyrrolidine compound of the compound 8 obtained as described above can be isolated and purified by generally used operations such as extraction, recrystallization, various types of chromatography and the like.

The palladium catalyst represented by the general formula Pd cat. is selected from debenzylation catalysts such as Pd/C.

Further, * in Scheme 1 represents asymmetric carbon atom.
(Acid)

In addition, according to the invention, an acid is included as another catalyst component.

As the acid, an organic acid or an inorganic acid can be used.

As the organic acid, illustrative examples thereof include acetic acid, chloroacetic acid, difluoroacetic acid, trifluoroacetic acid, trichloroacetic acid, tribromoacetic acid, benzoic acid, 2,4-dinitrobenzoic acid, paratoluenesulfonic acid, methanesulfonic acid, L-lactic acid, DL-tropic acid, DL-malic acid, L-malic acid, D-malic acid, DL-tartaric acid, D-tartaric acid, L-tartaric acid, L-dibenzoyltartaric acid, D-dibenzoyltartaric acid, DL-mandelic acid, L-mandelic acid, D-mandelic acid, citric acid, salicylic acid, trifluoromethanesulfonic acid, and the like.

As the inorganic acid, illustrative examples thereof include hydrofluoric acid, hydrochloric acid, hydrobromic acid, hydroiodic acid, sulfuric acid, perchloric acid, phosphoric acid, nitric acid and the like.

These acids may be used alone or in combination of two or more.

Among these acids, the trifluoroacetic acid, DL-tartaric acid, D-tartaric acid, L-tartaric acid, DL-mandelic acid, L-mandelic acid, D-mandelic acid, citric acid, salicylic acid, and hydrochloric acid are desirable.

<Substrate>

According to the invention, an α,β-unsaturated carbonyl compound is used as the substrate, and an optically active aldehyde or an optically active ketone, which is an optically active carbonyl compound, is produced by subjecting this to asymmetric hydrogenation using the catalyst of the invention.

As the α,β-unsaturated carbonyl compound to be used as the substrate, a compound represented by the following general formula (2) can, for example, be mentioned, although not particularly limited thereto. In this connection, in the case of the presence of Z-configuration and E-configuration regarding the double bond at the α-position and β-position of the α,β-unsaturated carbonyl compound, all of them are included therein.

General formula (2)

[Chem. 35]

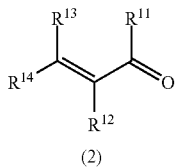

(2)

In the formula (2), $R^{11}$, $R^{12}$, $R^{13}$ and $R^{14}$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, an alkoxycarbonyl group which may have a substituent group, or an aralkyloxy group which may have a substituent group. In addition, $R^{11}$ and $R^{12}$, $R^{11}$ and $R^{13}$, $R^{11}$ and $R^{14}$, $R^{12}$ and $R^{14}$, or $R^{13}$ and $R^{14}$ may form a ring. However, when a ring is not formed by $R^{11}$ and $R^{12}$ or $R^{11}$ and $R^{13}$, and $R^{12}$ does not represent a hydrogen atom, $R^{13}$ and $R^{14}$ may be the same or different from each other; and when a ring is not formed by $R^{11}$ and $R^{12}$ or $R^{11}$ and $R^{13}$, and $R^{12}$ represents a hydrogen atom, $R^{13}$ and $R^{14}$ do not represent a hydrogen atom and different from each other.

An optically active aldehyde or an optically active ketone, which is an optically active carbonyl compound represented by the following formula (3), is produced by subjecting a compound represented by the aforementioned formula (2), namely an α,β-unsaturated aldehyde or an α,β-unsaturated ketone, to asymmetric hydrogenation using the catalyst of the invention.

[Chem. 36]

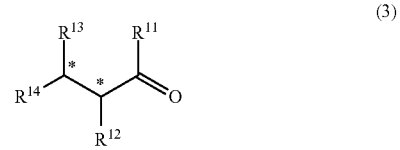

In the formula (3), $R^{11}$, $R^{12}$, $R^{13}$ and $R^{14}$ are the same as the definition of the formula (2). Two * mean that at least one * represents an asymmetric carbon atom.

Regarding the α,β-unsaturated carbonyl compound represented by the general formula (2) and the optically active carbonyl compound represented by the general formula (3), the groups represented by $R^{11}$, $R^{12}$, $R^{13}$ and $R^{14}$, namely the alkyl group, cycloalkyl group, alkenyl group, aryl group, aralkyl group, aromatic heterocyclic group, aliphatic heterocyclic group, acyl group, alkoxycarbonyl group and aralkyloxy group, are described. Each of these groups may have a substituent group.

As the alkyl group, a chain or branched alkyl group having from 1 to 30 carbon atoms, preferably from 1 to 10 carbon atoms, can be mentioned, and illustrative examples thereof include methyl group, ethyl group, n-propyl group, isopropyl group, n-butyl group, 2-butyl group, isobutyl group, tert-butyl group, n-pentyl group, 2-pentyl group, 3-pentyl group, tert-pentyl group, 2-methylbutyl group, 3-methylbutyl group, 2,2-dimethylpropyl group, 1,2-dimethylpropyl group, n-hexyl group, 2-hexyl group, 3-hexyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, heneicosyl group, and docosyl group.

In addition, these alkyl groups may have a substituent group, and as the substituent group of alkyl groups, including an alkenyl group, an alkynyl group, an aryl group, an aliphatic heterocyclic group, an aromatic heterocyclic group, an alkoxy group, an alkylenedioxy group, an aryloxy group, an aralkyloxy group, a heteroaryloxy group, an amino group, a substituted amino group, a nitro group, a cyano group, an alkoxycarbonyl group, a halogen atom, and an alkyl halide group.

The alkenyl group as the substituent group of the alkyl group includes a straight chain or branched alkenyl group having from 2 to 20 carbon atoms, preferably from 2 to 10 carbon atoms, more preferably from 2 to 6 carbon atoms, and illustrative examples thereof include vinyl group, propenyl group, 1-butenyl group, pentenyl group, and hexenyl group.

The alkynyl group as the substituent group of the alkyl group includes a straight chain or branched alkynyl group having from 2 to 15 carbon atoms, preferably from 2 to 10 carbon atoms, more preferably from 2 to 6 carbon atoms, and illustrative examples thereof include ethynyl group, 1-propynyl group, 2-propynyl group, 1-butynyl group, 3-butynyl group, pentinyl group, and hexynyl group.

As the aryl group as the substituent group of the alkyl group, an aryl group having from 6 to 14 carbon atoms can be mentioned, and illustrative examples thereof include phenyl group, naphthyl group, anthryl group, phenanthryl group, biphenyl group, tolyl group, xylyl group, mesityl group, methoxyphenyl group, dimethoxyphenyl group, and fluorophenyl group.

The aliphatic heterocyclic group as the substituent group of the alkyl group includes a group which has from 2 to 14 carbon atoms and contains, as heterogeneous atoms, at least one, preferably from 1 to 3 hetero atoms such as nitrogen atom, oxygen atom and sulfur atom. Preferable examples thereof include a 5- or 6-membered monocyclic aliphatic heterocyclic group and a polycyclic or condensed ring aliphatic heterocyclic group. As the aliphatic heterocyclic group, illustrative examples thereof include 2-oxo-1-pyrrolidinyl group, piperidino group, piperazinyl group, morpholino group, tetrahydrofuryl group, tetrahydropyranyl group, and tetrahydrothienyl group.

The aromatic heterocyclic group as the substituent group of the alkyl group includes a group which has from 2 to 15 carbon atoms and contains, heterogeneous atoms, at least one, preferably from 1 to 3 hetero atoms such as nitrogen atom, oxygen atom and sulfur atom. Preferable examples thereof include a 5- or 6-membered monocyclic aromatic heterocyclic group and a polycyclic or condensed ring aromatic heterocyclic group. As the aromatic heterocyclic group, illustrative examples thereof include furyl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, benzothiazolyl group and the like.

As the alkoxy group as the substituent group of the alkyl group, a straight chain or branched alkoxy group having from 1 to 6 carbon atoms can be mentioned, and illustrative examples thereof include methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group and the like.

As the alkylenedioxy group as the substituent group of the alkyl group, an alkylenedioxy group having from 1 to 3 carbon atoms can be mentioned, illustrative examples thereof include methylenedioxy group, ethylenedioxy group, propylenedioxy group, isopropylidenedioxy group and the like.

As the aryloxy group as the substituent group of the alkyl group, an aryloxy group having from 6 to 14 carbon atoms can be mentioned, and illustrative examples thereof include phenoxy group, naphthyloxy group, anthryloxy group and the like.

As the aralkyloxy group as the substituent group of the alkyl group an aralkyloxy group having from 7 to 12 carbon atoms can be mentioned, and illustrative examples thereof include benzyloxy group, 2-phenylethoxy group, 1-phenylpropoxy group, 2-phenylpropoxy group, 3-phenylpropoxy group, 1-phenylbutoxy group, 2-phenylbutoxy group, 3-phenylbutoxy group, 4-phenylbutoxy group, 1-phenylpentyloxy group, 2-phenylpentyloxy group, 3-phenylpentyloxy group, 4-phenylpentyloxy group, 5-phenylpentyloxy group, 1-phenylhexyloxy group, 2-phenylhexyloxy group, 3-phenylhexyloxy group, 4-phenylhexyloxy group, 5-phenylhexyloxy group, 6-phenylhexyloxy group and the like.

The heteroaryloxy group as the substituent group of the alkyl group includes a heteroaryloxy group which has from 2 to 14 carbon atoms and contains, as heterogeneous atoms, at least one, preferably from 1 to 3 hetero atoms such as nitrogen atom, oxygen atom and sulfur atom, and illustrative examples thereof include 2-pyridyloxy group, 2-pyrazyloxy group, 2-pyrimidyloxy group, 2-quinolyloxy group and the like.

As the substituted amino group as the substituent group of the alkyl group, examples thereof include mono- or di-alkylamino groups such as N-methylamino group, N,N-dimethylamino group, N,N-diethylamino group, N,N-diisopropylamino group and N-cyclohexylamino group; mono- or di-arylamino group such as N-phenylamino group, N,N-diphenylamino group, N-naphthylamino group and N-naphthyl-N-phenylamino group; mono- or di-aralkylamino group such as N-benzylamino group and N,N-dibenzylamino group.

The alkoxycarbonyl group as the substituent group of the alkyl group includes an alkoxycarbonyl group having from 1 to 30 carbon atoms, and illustrative examples thereof include methoxycarbonyl group, ethoxycarbonyl group, n-propoxycarbonyl group, isopropoxycarbonyl group, n-butoxycarbonyl group, 2-butoxycarbonyl group, isobutoxycarbonyl group, tert-butoxycarbonyl group, n-pentyloxycarbonyl group, 2-methylbutoxycarbonyl group, 3-methylbutoxycarbonyl group, 2,2-dimethylpropoxycarbonyl group, n-hexyloxycarbonyl group, 2-methylpentyloxycarbonyl group, 3-methylpentyloxycarbonyl group, 4-methylpentyloxycarbonyl group, 5-methylpentyloxycarbonyl group, cyclopentyloxycarbonyl group, cyclohexyloxycarbonyl group, dicyclopentylmethoxycarbonyl group, dicyclohexylmethoxycarbonyl group, tricyclopentylmethoxycarbonyl group, tricyclohexylmethoxycarbonyl group, phenylmethoxycarbonyl group, diphenylmethoxycarbonyl group, triphenylmethoxycarbonyl group and the like.

As the halogen atom as the substituent group of the alkyl group fluorine atom, chlorine atom, bromine atom, and iodine atom.

As the alkyl halide group as the substituent group of the alkyl group, a perhalogenoalkyl group is desirable, and examples thereof include trifluoromethyl group, pentafluoroethyl group, heptafluoropropyl group, undecafluoropentyl group, heptadecafluorooctyl group, undecafluorocyclohexyl group, and dichloromethyl group.

As the cycloalkyl group cyclopropyl group, cyclobutyl group, cyclopentyl group, and cyclohexyl group can be mentioned.

These cycloalkyl groups may have a substituent group, and as the substituent group, the substituent groups described in the aforementioned description on the substituent group of the alkyl group can be mentioned.

As the alkenyl group, a chain or branched or cyclic alkenyl group having from 2 to 20 carbon atoms, preferably from 2 to 10 carbon atoms, can be mentioned. As illustrative alkenyl groups, examples thereof include vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-cyclopentenyl group, 3-cyclopentenyl group, 1-hexenyl group, 2-hexenyl group, 3-hexenyl group, 4-hexenyl group, 5-hexenyl group, 4-methyl-3-pentenyl group, 4,8-dimethyl-3,7-nonadienyl group, 1-cyclohexenyl group, 3-cyclohexenyl group and the like.

These alkenyl groups may have a substituent group, and as the substituent group, the groups described in the aforementioned description on the substituent group of the alkyl group can be mentioned.

As the aryl group, an aryl group having from 6 to 14 carbon atoms can be mentioned, and illustrative examples thereof include phenyl group, naphthyl group, anthryl group, phenanthryl group, biphenyl group and the like.

These aryl groups may have a substituent group, and as the substituent group, the groups described in the description on the substituent group of the alkyl group can be mentioned.

The aralkyl group includes an aralkyl group having from 7 to 12 carbon atoms, and illustrative examples thereof include benzyl group, 2-phenylethyl group, 1-phenylpropyl group, 3-naphthylpropyl group and the like.

These aralkyl groups may have a substituent group, and as the substituent group, the groups described in the description on the substituent group of the alkyl group can be mentioned.

As the aromatic heterocyclic group, examples thereof include a group which has 2 to 15 carbon atoms and contains, as heterogeneous atoms, at least one, preferably 1 to 3 hetero atoms such as nitrogen atom, oxygen atom and sulfur atom. Preferable examples thereof include a 5- or 6-membered monocyclic aromatic heterocyclic group and a polycyclic or condensed ring aromatic heterocyclic group. As the aromatic heterocyclic group, illustrative examples thereof include furyl group, methylfuryl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, benzothiazolyl group and the like.

These aromatic heterocyclic groups may have a substituent group, and as the substituent group, the groups described in the description on the substituent group of the alkyl group can be mentioned.

The aliphatic heterocyclic group includes a group which has 2 to 14 carbon atoms and contains, as heterogeneous atoms, at least one, preferably 1 to 3 hetero atoms such as nitrogen atom, oxygen atom and sulfur atom. Preferable examples thereof include a 5- or 6-membered monocyclic aliphatic heterocyclic group and a polycyclic or condensed ring aliphatic heterocyclic group. As the aliphatic heterocyclic group, illustrative examples thereof include 2-oxo-1-pyrrolidinyl group, piperidino group, piperazinyl group, morpholino group, tetrahydrofuryl group, tetrahydropyranyl group, tetrahydrothienyl group and the like.

These aliphatic heterocyclic groups may have a substituent group, and as the substituent group, the groups described in the description on the substituent group of the alkyl group can be mentioned.

As the acyl group, for example, acetyl group, propanoyl group, butanoyl group, octanoyl group, benzoyl group, toluoyl group, xyloyl group, naphthoyl group, phenanthroyl group, and anthroyl group can be mentioned.

These acyl groups may have a substituent group, and as the substituent group, the groups described in the description on the substituent group of the alkyl group can be mentioned.

The alkoxycarbonyl group includes an alkoxycarbonyl group having from 1 to 30 carbon atoms, and illustrative examples thereof include methoxycarbonyl group, ethoxycarbonyl group, n-propoxycarbonyl group, isopropoxycarbonyl group, n-butoxycarbonyl group, 2-butoxycarbonyl group, isobutoxycarbonyl group, tert-butoxycarbonyl group, n-pentyloxycarbonyl group, 2-methylbutoxycarbonyl group, 3-methylbutoxycarbonyl group, 2,2-dimethylpropoxycarbonyl group, n-hexyloxycarbonyl group, 2-methylpentyloxycarbonyl group, 3-methylpentyloxycarbonyl group, 4-methylpentyloxycarbonyl group, 5-methylpentyloxycarbonyl group, cyclopentyloxycarbonyl group, cyclohexyloxycarbonyl group, dicyclopentylmethoxycarbonyl group, dicyclohexylmethoxycarbonyl group, tricyclopentylmethoxycarbonyl group, tricyclohexylmethoxycarbonyl group, phenylmethoxycarbonyl group, diphenylmethoxycarbonyl group, triphenylmethoxycarbonyl group and the like.

These alkoxycarbonyl groups may have a substituent group, and as the substituent group, the groups described in the description on the substituent group of the alkyl group can be mentioned.

As the aralkyloxy group, an aralkyloxy group having from 7 to 12 carbon atoms can be mentioned, and illustrative examples thereof include benzyloxy group, 2-phenylethoxy group, 1-phenylpropoxy group, 2-phenylpropoxy group, 3-phenylpropoxy group, 1-phenylbutoxy group, 2-phenylbutoxy group, 3-phenylbutoxy group, 4-phenylbutoxy group, 1-phenylpentyloxy group, 2-phenylpentyloxy group, 3-phenylpentyloxy group, 4-phenylpentyloxy group, 5-phenylpentyloxy group, 1-phenylhexyloxy group, 2-phenylhexyloxy group, 3-phenylhexyloxy group, 4-phenylhexyloxy group, 5-phenylhexyloxy group, 6-phenylhexyloxy group and the like.

These aralkyloxy groups may have a substituent group, and as the substituent group, the groups described in the description on the substituent group of the alkyl group can be mentioned.

As the ring formed by $R^{11}$ and $R^{12}$, $R^{11}$ and $R^{13}$, $R^{11}$ and $R^{14}$, $R^{12}$ and $R^{14}$, or $R^{13}$ and $R^{14}$ in the α,β-unsaturated carbonyl compound represented by the general formula (2) and the optically active carbonyl compound represented by the general formula (3), examples thereof include cyclopentane ring, cyclohexane ring, indane ring, tetralin ring, cyclopentene ring, cyclohexene ring, cycloheptene ring, indene ring, dihydronaphthalene ring, octahydronaphthalene ring, decahydronaphthalene ring and the like. These rings may be substituted with the aforementioned alkyl group, and the acyl group described in the following.

As the acyl group as the substituent group of the ring formed by $R^{11}$ and $R^{12}$, $R^{11}$ and $R^{13}$, $R^{11}$ and $R^{14}$, $R^{12}$ and $R^{14}$, or $R^{13}$ and $R^{14}$, acetyl group, propanoyl group, butanoyl group, octanoyl group, benzoyl group, toluoyl group, xyloyl group, naphthoyl group, phenanthroyl group, anthroyl group and the like can be mentioned.

As illustrative examples of the α,β-unsaturated aldehyde to be used as the substrate in the invention, the following compounds can be mentioned. In this connection, in the case of the presence of Z-configuration and E-configuration regarding the double bond at the α-position and β-position of the α,β-unsaturated aldehyde, all of them are included therein. The wavy line in the following compounds represents Z-configuration, E-configuration or a mixture thereof.

In the following compounds, Me represents methyl group, and Bn represents benzyl group.

[Chem. 37]

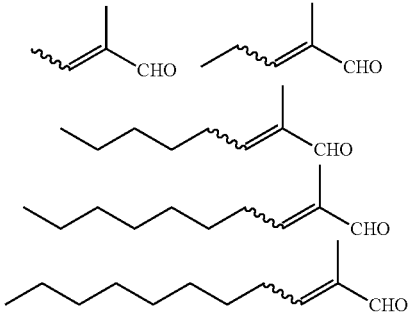

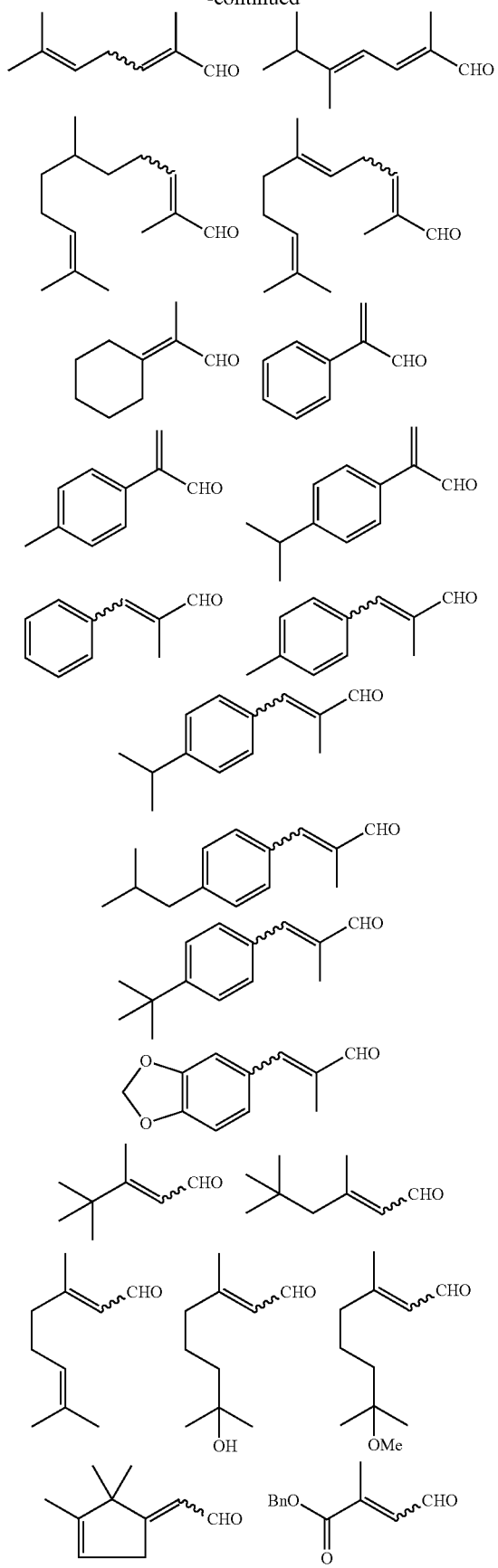

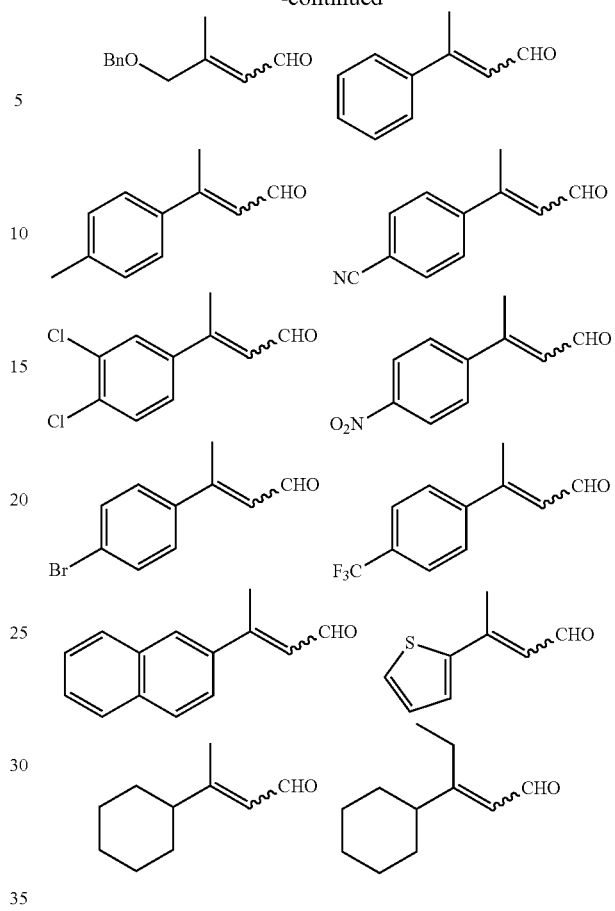

Among the aforementioned α,β-unsaturated aldehydes, geranial (the following A), neral (the following B) and citral can be mentioned as particularly desirable compounds.

[Chem. 38]

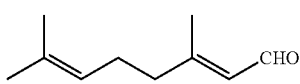 (A)

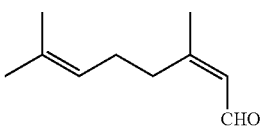 (B)

As the α,β-unsaturated ketone to be used as the substrate in the invention, ketones having from 5 to 18 carbon atoms are desirable.

As illustrative examples of the α,β-unsaturated ketone, the following compounds can be mentioned. In this connection, in the case of the presence of Z-configuration and E-configuration regarding the double bond at the α-position and β-position of the α,β-unsaturated ketone, all of them are included therein. The wavy line in the following compounds represents Z-configuration, E-configuration or a mixture thereof.

In the following compounds, Me represents a methyl group, Ph represents a phenyl group, Et represents an ethyl group, Bu represents a butyl group, Pr represents a propyl group and Bn represents a benzyl group.

[Chem. 39]
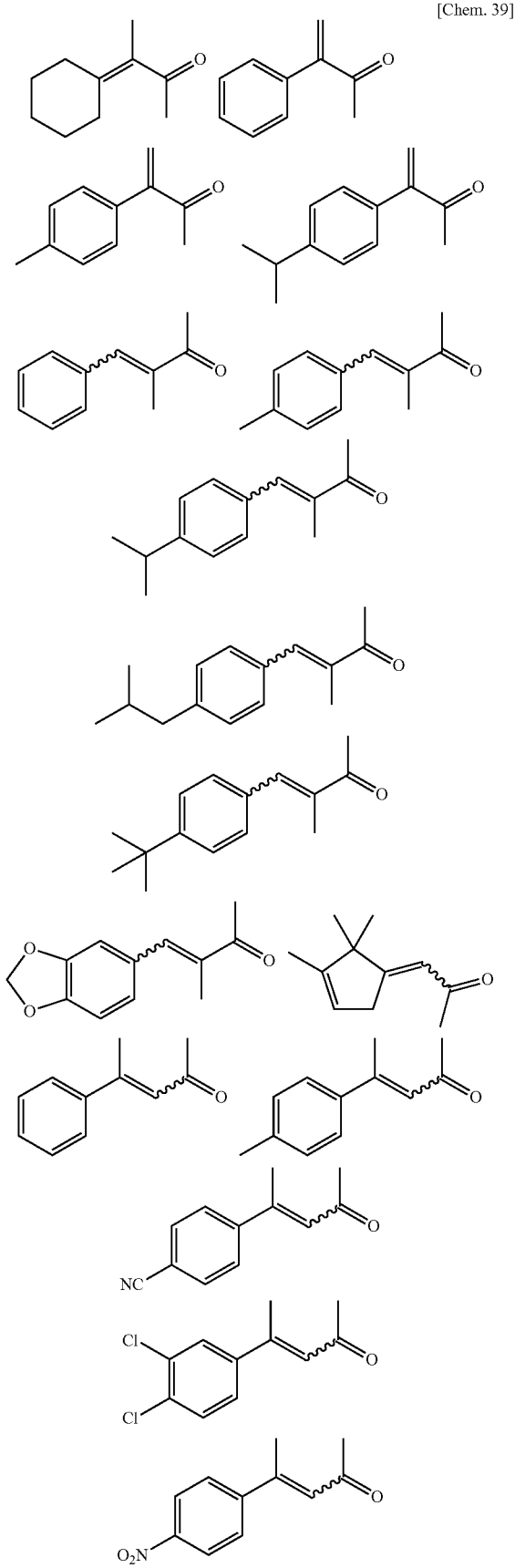
[Chem. 40]
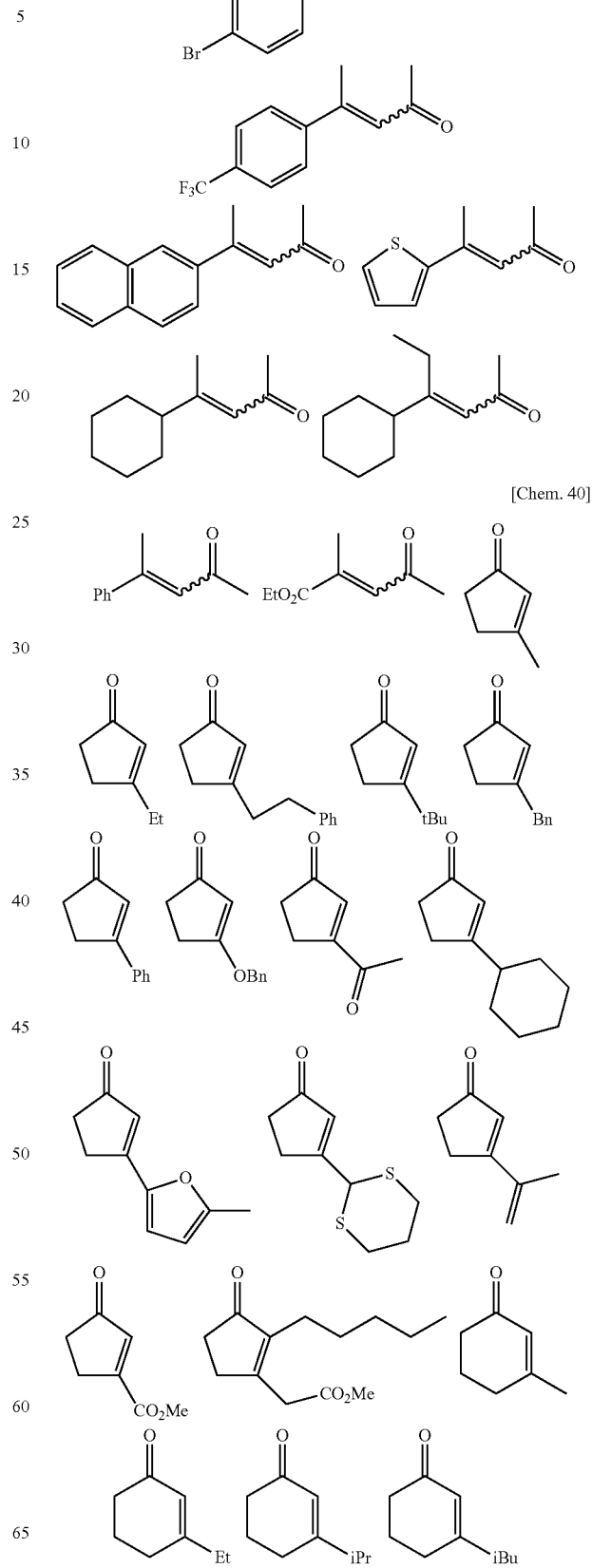

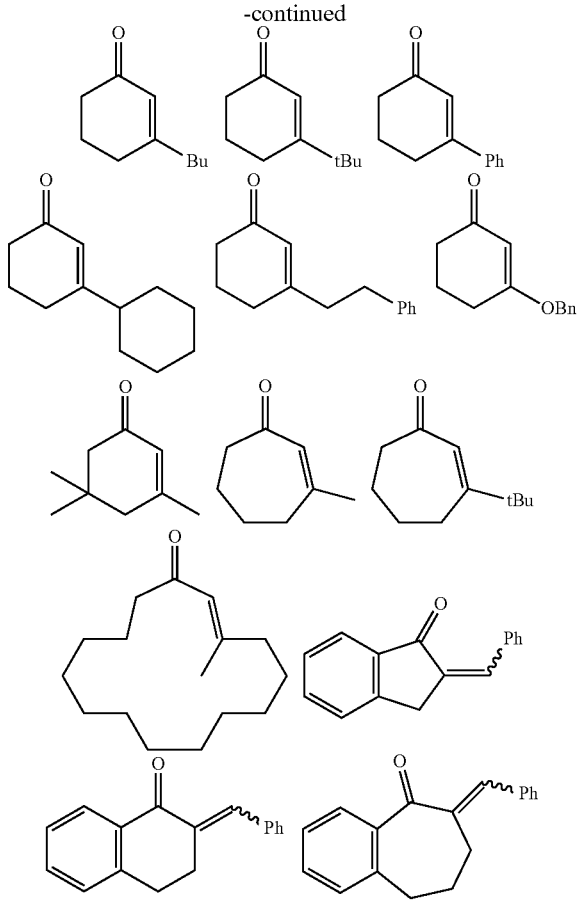

<Production Method of Optically Active Carbonyl Compound>

According to the invention, an optically active carbonyl compound such as an optically active aldehyde or an optically active ketone can be obtained by subjecting an α,β-unsaturated carbonyl compound to asymmetric hydrogenation reaction in the presence of the aforementioned catalyst.

The amounts of the metal powder and metal-supported substance to be used as catalyst components of the invention vary depending on various reaction conditions, but total weight of the metal powder and total weight of the metal-supported substance are, for example, from 0.01 to 10% by weight, preferably from 0.02 to 5% by weight, based on the weight of the α,β-unsaturated carbonyl compound as the substrate.

The amount of the optically active cyclic nitrogen-containing compound to be used as a catalyst component of the invention vary depending on various reaction conditions, but is, for example, from 0.01 to 20% by weight, preferably from 0.04 to 10% by weight, based on the α,β-unsaturated carbonyl compound as the substrate.

The amount of the acid to be used as catalyst components of the invention vary depending on various reaction conditions, but is, for example, 0.01 to 10 times by mol, preferably 0.2 to 4 times by mol based on the optically active cyclic nitrogen-containing compound.

When an optically active carbonyl compound is produced by carrying out asymmetric hydrogenation of the α,β-unsaturated carbonyl compound using the catalyst of the invention, it can be carried out in the presence or absence of a solvent, but it is desirable to carry it out in the presence of a solvent.

As the solvent to be used, illustrative preferable examples thereof include aliphatic hydrocarbon-based organic solvents such as hexane, heptane and octane; alicyclic hydrocarbon-based organic solvents such as cyclohexane and methylcyclohexane; aromatic hydrocarbon-based organic solvents such as benzene, toluene and xylene; ether-based organic solvents such as diethyl ether, diisopropyl ether, dimethoxyethane, tetrahydrofuran, dioxane and dioxolan; water; alcohol-based organic solvents such as methanol, ethanol, propanol, isopropanol and tertiary butanol; halogenated hydrocarbon-based organic solvents such as dichloromethane, dichloroethane, chlorobenzene and bromotoluene; dimethylformamide, acetonitrile and the like, and a mixed solvent of these solvents can also be used if necessary. Among these solvents, heptane, toluene, tetrahydrofuran, t-butanol and hydrous t-butanol are particularly desirable.

The amount of the solvent used can be optionally selected depending on the reaction conditions and the like, but is, for example, from 0 to 20 times volume (ml) [(ml/g)], preferably from 0 to 5 times volume (ml) [(ml/g)], based on the weight (g) of the α,β-unsaturated carbonyl compound as the substrate.

The method of the invention is carried out using hydrogen gas as the hydrogen source, and its hydrogen pressure is from 0.01 MPa to 10 MPa, preferably from 0.1 MPa to 1 MPa. Further, instead of the hydrogen gas, a gas mixture of hydrogen gas and inert gas such as nitrogen, helium and argon may be used.

The reaction temperature is from −78 to 100° C., preferably from 10 to 70° C. The reaction time varies depending on the reaction conditions, but is generally from 1 to 30 hours.

The optically active carbonyl compound obtained as described above can be isolated and purified by generally used operations such as extraction, recrystallization, various types of chromatography and the like. In addition, regarding configuration of the thus obtained optically active carbonyl compound, its d-form or l-form (R-form or S-form) can be produced by optionally selecting configuration of the optically active cyclic nitrogen-containing compound.

EXAMPLES

The following describes the invention further illustratively based on examples and comparative examples, though the invention is not restricted thereby.

In the following description, Bu represents a butyl group, tBu represents a t-butyl group, Et represents an ethyl group, Me represents a methyl group, Ph represents a phenyl group, and Oct represents an octyl group.

Measurement of the products was carried out by a gas chromatographic method (GLC). Its conditions are as described in the following.

The used instrument for analysis: G2010 gas chromatography manufactured by Shimadzu Corp.

Column: DB-WAX (0.25 mm×30 m) manufactured by Agilent for conversion ratio measurement β-DEX-225 (0.25 mm×30 m) manufactured by SUPELCO for optical purity Detector: FID Among the optically active cyclic nitrogen-containing compounds represented by the general formula (1), the compounds used in Examples 1 to 52 were synthesized by the following methods.

Synthesis Example 1

Synthesis of (2R,4R)-4-Hydroxyproline-N-ethyl carbamate methyl ester

[Chem. 41]

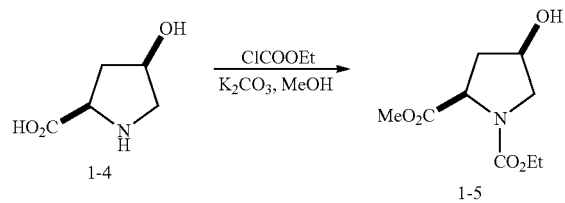

This was carried out in accordance with the synthesis method of Tetrahedron, Vol. 49, No. 23, 5127-5132.

25.0 g (191 mmol) of (2R,4R)-hydroxyproline (manufactured by Watanabe Chemical Industries Ltd.), 150 ml of anhydrous methanol and 26.4 g (191 mmol) of potassium carbonate were put into a 300 ml capacity four neck flask, followed by stirring. Under ice-cooling, 40.2 ml (420 mmol) of ethyl chlorocarbonate was added dropwise thereto at 25° C. or less, followed by stirring at 0° C. for 24 hours. After filtering the reaction solution, methanol was evaporated, the residue was mixed with 150 ml of water and extracted with 150 ml of chloroform, and the water layer was further extracted twice with 150 ml of chloroform. The thus obtained organic layer was washed with saturated brine, dried with anhydrous magnesium sulfate and filtered, and then the solvent was evaporated to obtain 36.5 g of the product of interest with a yield of 94.0%.

Synthesis Example 2

Synthesis of (5R,7R)-[3,3,0]-1-aza-2-oxo-3-oxa-4,4-bis-(4'-t-butylphenyl)-7-hydroxybicyclooctane

[Chem. 42]

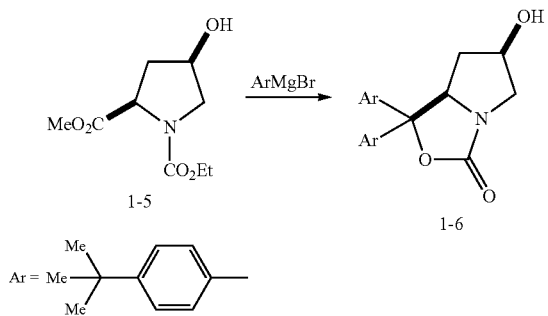

This was carried out in accordance with the synthesis method of (S)-2-(diphenylmethyl)pyrrolidine described in Tetrahedron: Asymmetry, Vol. 8, No. 1, 149-153.

Under a stream of nitrogen, 2.41 g (99 mmol) of magnesium and 15 ml of anhydrous THF were put into a nitrogen-replaced 500 ml capacity reaction flask, followed by stirring. At room temperature, a 75 ml THF solution of 19.2 g (90 mmol) of 4-t-butylphenylbromobenzene was added dropwise thereto, followed by stirring at room temperature for 1 hour (synthesis of a Grignard compound).

Next, the above-mentioned solution was cooled to 5° C. or less, and a 125 ml THF solution of 6.10 g (30 mmol) of the (2R,4R)-4-Hydroxyproline-N-ethyl carbamate methyl ester obtained in Synthesis Example 1 was added dropwise thereto at 10° C. or less and allowed to undergo the reaction. Thereafter, this was heated under reflux for 3 hours and then cooled, and the reaction solution was added to 100 ml of saturated ammonium chloride aqueous solution. After recovering the THF, a concentrate was extracted twice with 200 ml of ethyl acetate, and the combined organic layers were washed twice with saturated brine. After drying the organic layer with anhydrous sodium sulfate, the solvent was evaporated, and the thus obtained concentrate was recrystallized from ethyl acetate/hexane to obtain 8.24 g of the product of interest.

Synthesis Example 3

Synthesis of (5R,7R)-[3,3,0]-1-aza-2-oxo-3-oxa-4,4-bis-(4'-t-butylphenyl)-7-(butylcarbamoyloxy)bicyclooctane

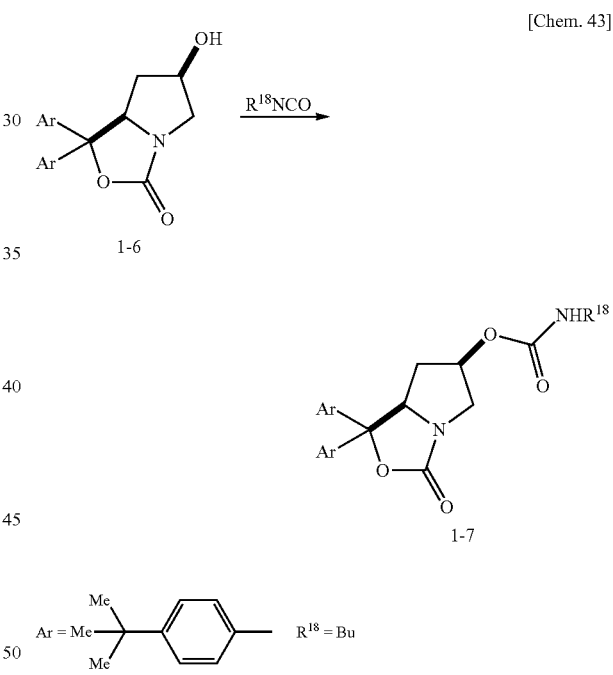

[Chem. 43]

900 mg (2.21 mmol) of (5R,7R)-[3,3,0]-1-aza-2-oxo-3-oxa-4,4-bis-(4'-t-butylphenyl)-7-hydroxybicyclooctane obtained in Synthesis Example 2, 9 ml of anhydrous DMF and 110 mg (1.11 mmol) of copper(I) chloride were put into a 50 ml capacity four neck flask, followed by stirring. At room temperature, 0.37 ml (3.32 mmol) of n-butylisocyanate was added dropwise thereto, followed by stirring at room temperature for 4 hours. After extraction by adding water and toluene to the reaction solution, the combined organic layers were washed with water and saturated brine. The solvent was evaporated, and then purified by a silica gel column chromatography, thereby obtaining 1.10 g of the colorless oily product of interest with a yield of 98.2%.

Synthesis Example 4

Synthesis of (2R,4R)-2-(bis-(4'-t-butylphenyl)methyl)-4-(butylcarbamoyloxy)pyrrolidine Synthesis of the Optically Active Cyclic Nitrogen-Containing Compound Used in Examples 1, 6 and 12

[Chem. 44]

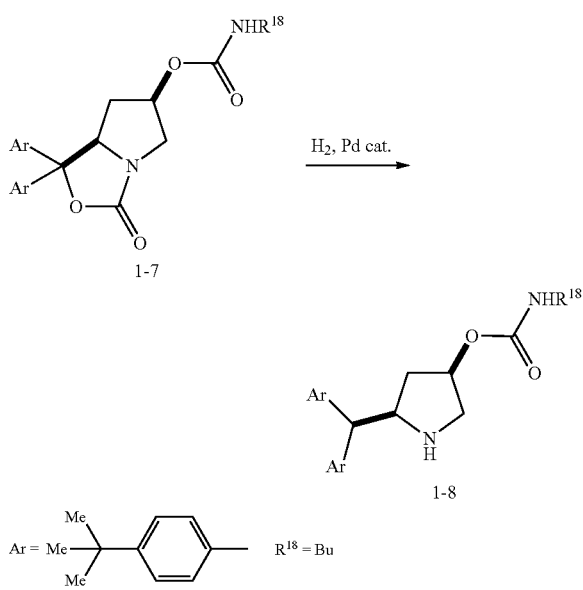

10.8 ml of methanol, 10.8 ml of THF and 135 mg of 10% by weight Pd/C were added to 1.08 g (2.13 mmol) of (5R,7R)-[3,3,0]-1-aza-2-oxo-3-oxa-4,4-bis-(4'-t-butylphenyl)-7-(butylcarbamoyloxy)bicyclooctane obtained in Synthesis Example 3, followed by stirring and carrying out hydrogen replacement. After carrying out 3 days of the reaction at room temperature under a hydrogen atmosphere, Pd/C was removed by filtration and the filtrate was concentrated and purified by a silica gel column chromatography, thereby obtaining 720 mg of the colorless oily product of interest with a yield of 72.7%.

$^1$H-NMR (CD$_3$OD): δ=0.80 to 0.95, t, 3H δ=1.20 to 1.30, s, 18H δ=1.15 to 1.55, m, 6H δ=2.05 to 2.20, m, 1H δ=2.90 to 3.10, m, 4H δ=3.70 to 3.95, m, 2H δ=4.90 to 5.05, bs, 1H δ=7.10 to 7.35, m, 8H

Synthesis Example 5

Synthesis of (5R,7R)-[3,3,0]-1-aza-2-oxo-3-oxa-4,4-bis-(4'-t-butylphenyl)-7-(t-butylcarbamoyloxy)bicyclooctane

[Chem. 45]

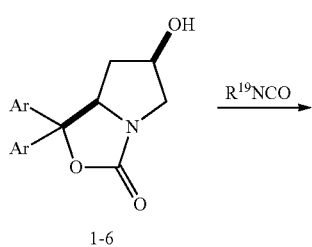

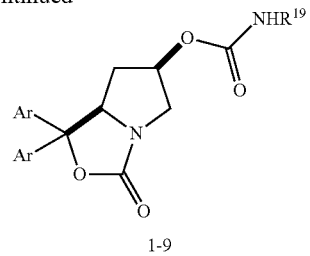

900 mg (2.21 mmol) of (5R,7R)-[3,3,0]-1-aza-2-oxo-3-oxa-4,4-bis-(4'-t-butylphenyl)-7-hydroxybicyclooctane obtained in Synthesis Example 2, 9 ml of anhydrous DMF and 110 mg (1.11 mmol) of copper(I) chloride were put into a 50 ml capacity four neck flask, followed by stirring. At room temperature, 0.39 ml (3.32 mmol) of n-butylisocyanate was added dropwise thereto, followed by stirring at room temperature for 4 hours. After extraction by adding water and toluene to the reaction solution, the combined organic layers were washed with water and saturated brine. The solvent was evaporated, and then purified by a silica gel column chromatography, thereby obtaining 1.09 g of the colorless oily product of interest with a yield of 97.3%.

Synthesis Example 6

Synthesis of (2R,4R)-2-(bis-(4'-t-butylphenyl)methyl)-4-(t-butylcarbamoyloxy)pyrrolidine Synthesis of the Optically Active Cyclic Nitrogen-Containing Compound Used in Examples 7 and 13

[Chem. 46]

10.8 ml of methanol, 10.8 ml of THF and 135 mg of 10% by weight Pd/C were added to 1.08 g (2.13 mmol) of (5R,7R)-[3,3,0]-1-aza-2-oxo-3-oxa-4,4-bis-(4'-t-butylphenyl)-7-(t-butylcarbamoyloxy)bicyclooctane obtained in Synthesis Example 5, followed by stirring and carrying out hydrogen replacement. After carrying out 3 days of the reaction at room temperature under a hydrogen atmosphere, Pd/C was removed by filtration and the filtrate was concentrated and purified by a silica gel column chromatography, thereby obtaining 690 mg of the colorless oily product of interest with a yield of 60.1%.

$^1$H-NMR (CD$_3$Cl$_3$): δ=1.20, s, 9H δ=1.22, s, 9H δ=1.25, s, 9H δ=1.20 to 1.30, m, 1H δ=1.50 to 1.65, m, 1H δ=2.10 to 2.30, m, 1H δ=2.90 to 3.00, m, 2H δ=3.70 to 3.40, m, 2H δ=5.00 to 5.20, bs, 1H δ=7.10 to 7.40, m, 8H

Synthesis Example 7

Synthesis of (5R,7R)-[3,3,0]-1-aza-2-oxo-3-oxa-4,4-bis-(4'-t-butylphenyl)-7-(ethylcarbamoyloxy)bicyclooctane

[Chem. 47]

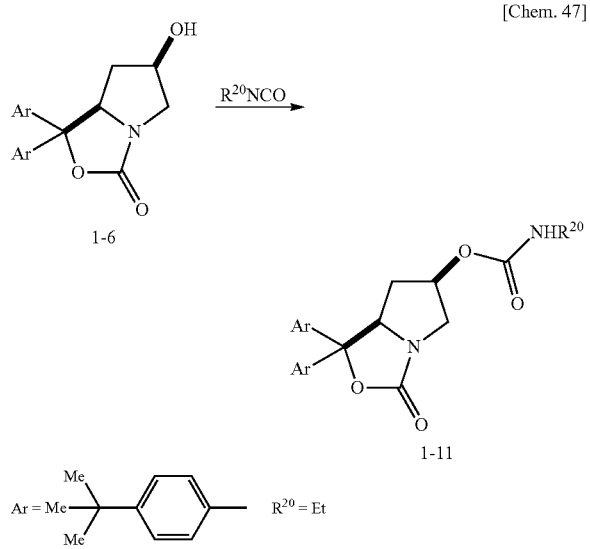

900 mg (2.21 mmol) of (5R,7R)-[3,3,0]-1-aza-2-oxo-3-oxa-4,4-bis-(4'-t-butylphenyl)-7-hydroxybicyclooctane obtained in Synthesis Example 2, 9 ml of anhydrous DMF and 110 mg (1.11 mmol) of copper(I) chloride were put into a 50 ml capacity four neck flask, followed by stirring. At room temperature, 0.26 ml (3.32 mmol) of ethylisocyanate was added dropwise thereto, followed by stirring at room temperature for 4 hours. After extraction by adding water and toluene to the reaction solution, the combined organic layers were washed with water and saturated brine. The solvent was evaporated, and then purified by a silica gel column chromatography, thereby obtaining 680 mg of the colorless oily product of interest with a yield of 64.3%.

Synthesis Example 8

Synthesis of (2R,4R)-2-(bis-(4'-t-butylphenyl)methyl)-4-(ethylcarbamoyloxy)pyrrolidine Synthesis of the Optically Active Cyclic Nitrogen-Containing Compound Used in Examples 2, 8 and 16-51

[Chem. 48]

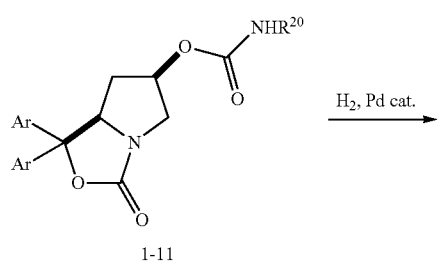

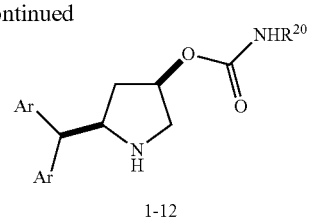

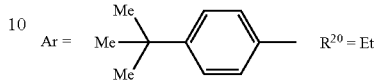

10.8 ml of methanol, 10.8 ml of THF and 135 mg of 10% by weight Pd/C were added to 1.08 g (2.13 mmol) of (5R, 7R)-[3,3,0]-1-aza-2-oxo-3-oxa-4,4-bis-(4'-t-butylphenyl)-7-(ethylcarbamoyloxy)bicyclooctane obtained in Synthesis Example 7, followed by stirring and carrying out hydrogen replacement. After carrying out 3 days of the reaction at room temperature under a hydrogen atmosphere, Pd/C was removed by filtration and the filtrate was concentrated and purified by a silica gel column chromatography, thereby obtaining 480 mg of the colorless oily product of interest with a yield of 80.8%.

$^1$H-NMR (CD$_3$Cl$_3$): δ=1.05 to 1.20, t, 3H δ=1.25, s, 18H δ=1.30 to 1.60, m, 2H δ=2.15 to 2.30, m, 1H δ=2.95 to 3.25, m, 4H δ=3.80, bs, 2H δ=4.60, bs, 1H δ=5.10, bs, 1H δ=7.10 to 7.30, m, 8H

Synthesis Example 9

Synthesis of (5R,7R)-[3,3,0]-1-aza-2-oxo-3-oxa-4,4-bis-(4'-t-butylphenyl)-7-(octylcarbamoyloxy)bicyclooctane

[Chem. 49]

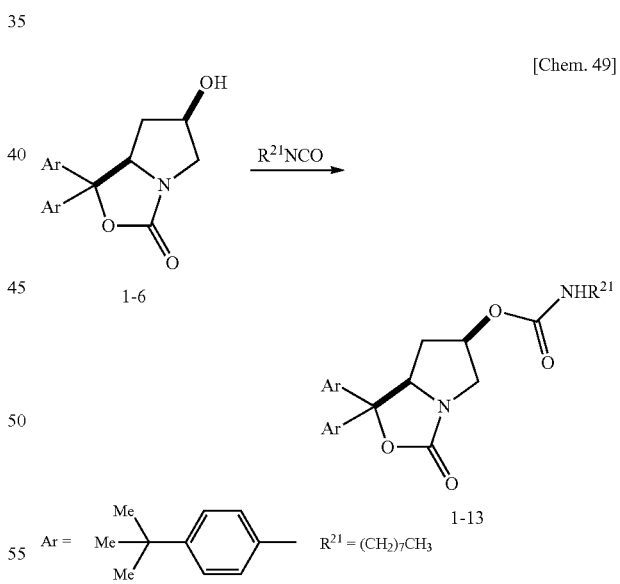

900 mg (2.21 mmol) of (5R,7R)-[3,3,0]-1-aza-2-oxo-3-oxa-4,4-bis-(4'-t-butylphenyl)-7-hydroxybicyclooctane obtained in Synthesis Example 2, 9 ml of anhydrous DMF and 110 mg (1.11 mmol) of copper(I) chloride were put into a 50 ml capacity four neck flask, followed by stirring. At room temperature, 0.59 ml (3.32 mmol) of octylisocyanate was added dropwise thereto, followed by stirring at room temperature for 4 hours. After extraction by adding water and toluene to the reaction solution, the combined organic layers were washed with water and saturated brine. The solvent was evaporated, and then purified by a silica gel column chromatography, thereby obtaining 1.08 g of the colorless oily product of interest with a yield of 86.8%.

Synthesis Example 10

Synthesis of (2R,4R)-2-(bis-(4'-t-butylphenyl)methyl)-4-(octylcarbamoyloxy)pyrrolidine Synthesis of the Optically Active Cyclic Nitrogen-Containing Compound Used in Examples 3 and 9

[Chem. 50]

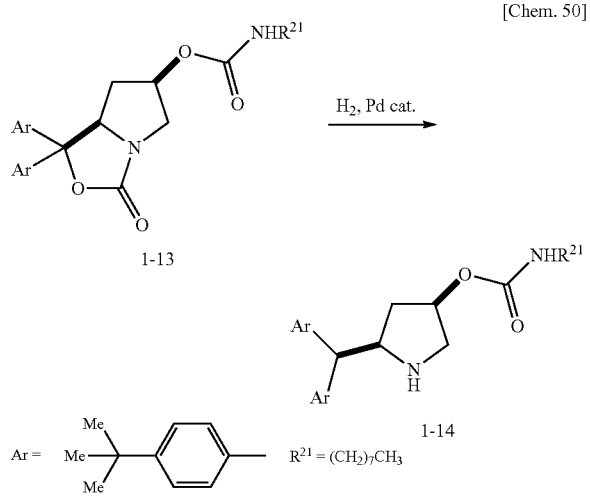

10.8 ml of methanol, 10.8 ml of THF and 135 mg of 10% by weight Pd/C were added to 1.08 g (2.13 mmol) of (5R,7R)-[3,3,0]-1-aza-2-oxo-3-oxa-4,4-bis-(4'-t-butylphenyl)-7-(octylcarbamoyloxy)bicyclooctane obtained in Synthesis Example 9, followed by stirring and carrying out hydrogen replacement. After carrying out 3 days of the reaction at room temperature under a hydrogen atmosphere, Pd/C was removed by filtration and the filtrate was concentrated and purified by a silica gel column chromatography, thereby obtaining 540 mg of the colorless oily product of interest with a yield of 58.3%.

$^1$H-NMR (CD$_3$OD): δ=0.80 to 0.95, t, 3H δ=1.00 to 1.60, m, 14H δ=1.10, s, 18H δ=2.00 to 2.20, m, 1H δ=2.90 to 3.20, m, 4H δ=3.70 to 4.00, m, 2H δ=5.00 to 5.10, bs, 1H δ=7.10 to 7.40, m, 8H

Synthesis Example 11

Synthesis of (5R,7R)-[3,3,0]-1-aza-2-oxo-3-oxa-4,4-bis-(4'-t-butylphenyl)-7-(diphenylcarbamoyloxy)bicyclooctane

[Chem. 51]

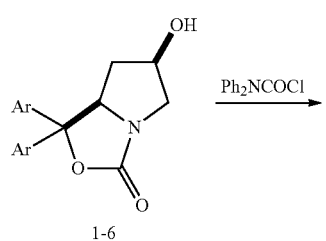

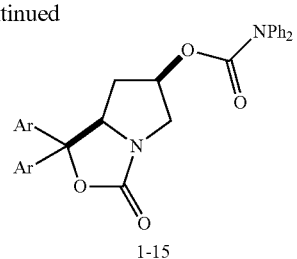

1.00 g (2.45 mmol) of (5R,7R)-[3,3,0]-1-aza-2-oxo-3-oxa-4,4-bis-(4'-t-butylphenyl)-7-hydroxybicyclooctane obtained in Synthesis Example 2, 10 ml of anhydrous DMF and 118 mg (4.90 mmol) of sodium hydride were put into a 50 ml capacity four neck flask, followed by stirring. Under ice-cooling, 626 mg (2.70 mmol) of diphenylcarbamoyl chloride was added dropwise thereto, followed by stirring at room temperature for 2 hours. After extraction by adding water and toluene to the reaction solution, the combined organic layers were washed with water and saturated brine. The solvent was evaporated, and then purified by a silica gel column chromatography, thereby obtaining 920 mg of the colorless oily product of interest with a yield of 62.3%.

Synthesis Example 12

Synthesis of (2R,4R)-2-(bis-(4'-t-butylphenyl)methyl)-4-(diphenylcarbamoyloxy)pyrrolidine Synthesis of the Optically Active Cyclic Nitrogen-Containing Compound Used in Examples 4 and 10

[Chem. 52]

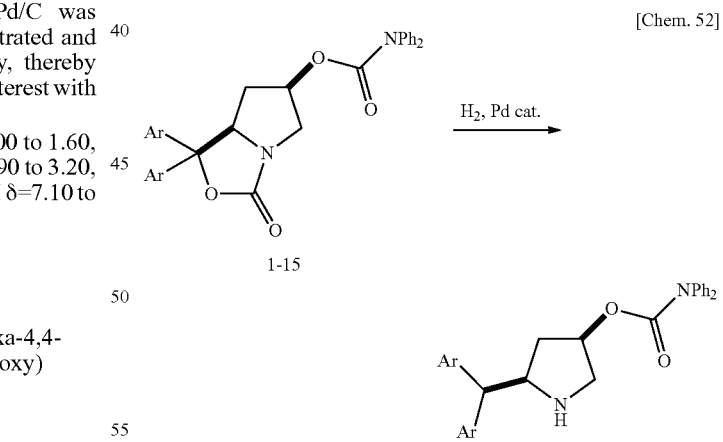

18.4 ml of methanol, 18.4 ml of THF and 115 mg of 10% by weight Pd/C were added to 920 mg (1.53 mmol) of (5R,7R)-[3,3,0]-1-aza-2-oxo-3-oxa-4,4-bis-(4'-t-butylphenyl)-7-(diphenylcarbamoyloxy)bicyclooctane obtained in Synthesis Example 11, followed by stirring and carrying out hydrogen replacement. After carrying out 5 days of the reaction at room temperature under a hydrogen atmosphere, Pd/C was removed by filtration and the filtrate was concentrated and purified by a silica gel column chromatography, thereby obtaining 680 mg of the colorless oily product of interest with a yield of 79.3%.

$^1$H-NMR (CD$_3$OD): δ=1.20 to 1.35, s, 18H δ=1.45 to 1.60, m, 1H δ=2.00 to 2.20, m, 1H δ=2.90 to 3.00, m, 1H δ=3.10 to 3.20, m, 1H δ=3.35 to 3.45, m, 1H δ=3.85 to 4.00, m, 1H δ=5.15 to 5.25, m, 1H δ=6.90 to 7.50, m, 18H

Synthesis Example 13

Synthesis of (5R,7R)-[3,3,0]-1-aza-2-oxo-3-oxa-4,4-diphenyl-7-hydroxybicyclooctane

[Chem. 53]

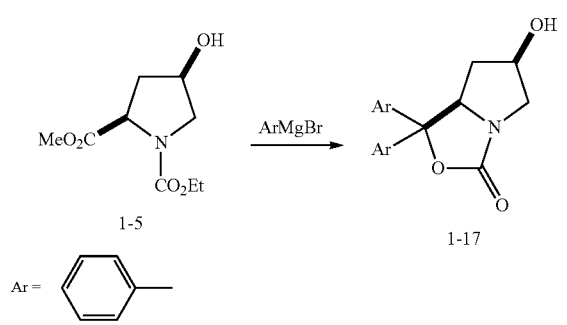

This was carried out in accordance with the synthesis method of (S)-2-(diphenylmethyl)pyrrolidine described in Tetrahedron: Asymmetry, Vol. 8, No. 1, 149-153.

Under a stream of nitrogen, a 50 ml THF solution of 5.10 g (23 mmol) of (2R,4R)-4-Hydoxyproline-N-ethyl carbamate methyl ester obtained in Synthesis Example 1 was put into a nitrogen-replaced 500 ml capacity reaction flask, and cooled to 10° C. or less. A 64 ml THF solution of 1.08 mol/L of phenylmagnesium bromide was added from a dropping funnel dropwise thereto and allowed to undergo the reaction. Thereafter, this was heated under reflux for 3 hours and then cooled, and the reaction solution was added to 100 ml of saturated ammonium chloride aqueous solution. After recovering the THF, a concentrate was extracted twice with 200 ml of ethyl acetate, and the combined organic layers were washed twice with saturated brine. After drying the organic layer with anhydrous sodium sulfate, the solvent was evaporated, and the thus obtained concentrate was isolated and purified by a silica gel column chromatography, thereby obtaining 3.43 g of the product of interest.

Synthesis Example 14

Synthesis of (5R,7R)-[3,3,0]-1-aza-2-oxo-3-oxa-4,4-diphenyl-7-(butylcarbamoyloxy)bicyclooctane

[Chem. 54]

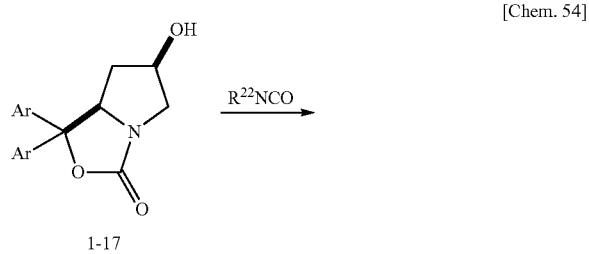

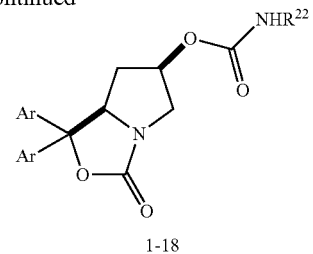

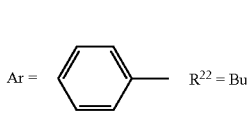

3.43 g (11.6 mmol) of (5R,7R)-[3,3,0]-1-aza-2-oxo-3-oxa-4,4-diphenyl-7-hydroxybicyclooctane obtained in Synthesis Example 13, 17 ml of anhydrous DMF and 115 mg (1.16 mmol) of copper(I) chloride were put into a 100 ml capacity four neck flask, followed by stirring. At room temperature, 1.55 ml (1.39 mmol) of n-butylisocyanate was added dropwise thereto, followed by stirring at room temperature for 4 hours. After extraction by adding water and toluene to the reaction solution, the combined organic layers were washed with water and saturated brine. The solvent was evaporated, and then purified by a silica gel column chromatography, thereby obtaining 1.91 g of the colorless oily product of interest with a yield of 41.9%.

Synthesis Example 15

Synthesis of (2R,4R)-2-diphenylmethyl-4-(butylcarbamoyloxy)pyrrolidine

Synthesis of the Optically Active Cyclic Nitrogen-Containing Compound Used in Examples 5 and 11

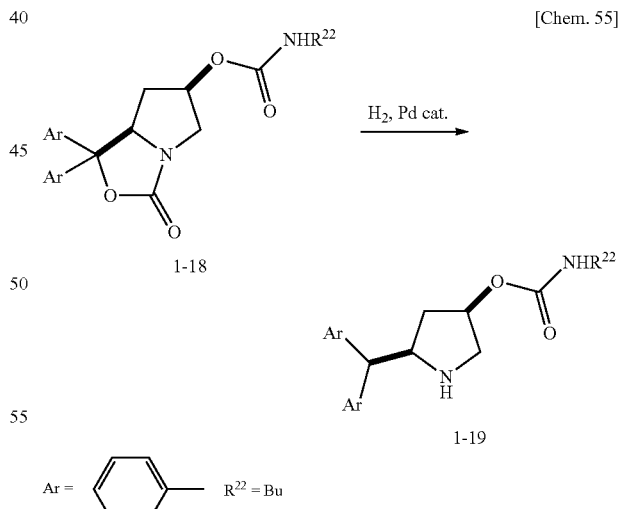

19 ml of methanol and 95.6 mg of 10% by weight Pd/C were added to 1.91 g (4.87 mmol) of (5R,7R)-[3,3,0]-1-aza-2-oxo-3-oxa-4,4-diphenyl-7-(butylcarbamoyloxy)bicyclooctane obtained in Synthesis Example 14, followed by stirring and carrying out hydrogen replacement. After carrying out 3 days of the reaction at 40° C. under a hydrogen atmosphere, Pd/C was removed by filtration and the filtrate was concentrated and purified by a silica gel column chromatography, thereby obtaining 690 mg of the colorless oily product of interest with a yield of 40.3%.

$^1$H-NMR (CD$_3$OD): δ=0.90 to 0.96, t, 3H δ=1.30 to 1.59, m, 5H δ=2.10 to 2.21, qui, 1H δ=3.00 to 3.11, m, 4H δ=3.86 to 4.05, m, 2H δ=5.00 to 5.05, m, 1H δ=7.14 to 7.41, m, 10H Synthesis Example 16

Synthesis of (5R,7R)-[3,3,0]-1-aza-2-oxo-3-oxa-4,4-bis-(4'-t-butylphenyl)-7-(t-butylcarbonyloxy)bicyclooctane

[Chem. 56]

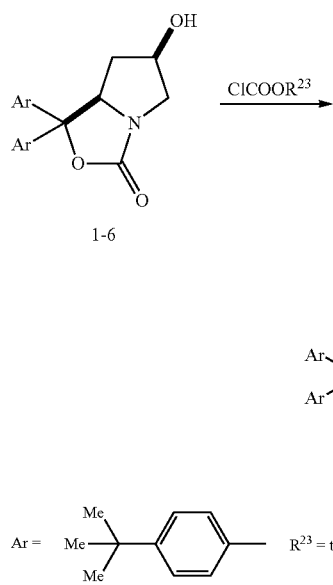

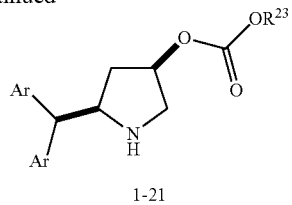

1020 mg (2.50 mmol) of (5R,7R)-[3,3,0]-1-aza-2-oxo-3-oxa-4,4-bis-(4'-t-butylphenyl)-7-hydroxybicyclooctane obtained in Synthesis Example 2, 10.2 ml of anhydrous THF and 6 mg (0.05 mmol) of N,N-dimethyl-4-aminopyridine were put into a 50 ml capacity four neck flask, followed by stirring. At room temperature, 600 mg (2.76 mmol) of di-t-butyl-dicarbonate was added dropwise thereto, followed by stirring at room temperature for 4 hours. After extraction by adding water and toluene to the reaction solution, the combined organic layers were washed with water and saturated brine. The solvent was evaporated, and then purified by a silica gel column chromatography, thereby obtaining 0.96 g of the product of interest with a yield of 75.6%.

Synthesis Example 17

Synthesis of (2R,4R)-2-(bis-(4'-t-butylphenyl)methyl)-4-(t-butylcarbonyloxy)pyrrolidine Synthesis of the Optically Active Cyclic Nitrogen-Containing Compound Used in Example 14

[Chem. 57]

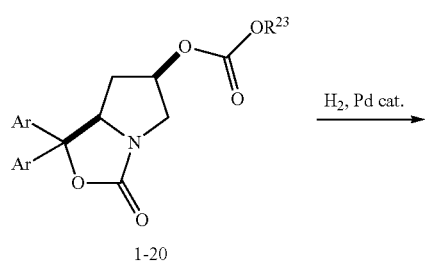

13.5 ml of methanol, 13.5 ml of THF and 150 mg of 5% by weight Pd/C were added to 900 mg (1.77 mmol) of (5R,7R)-[3,3,0]-1-aza-2-oxo-3-oxa-4,4-bis-(4'-t-butylphenyl)-7-(t-butylcarbonyloxy)bicyclooctane obtained in Synthesis Example 16, followed by stirring and carrying out hydrogen replacement. After carrying out 24 hours of the reaction at 35° C. under a hydrogen atmosphere, Pd/C was removed by filtration and the filtrate was concentrated and purified by a silica gel column chromatography, thereby obtaining 580 mg of the product of interest with a yield of 70.4%.

$^1$H-NMR (CD$_3$OD): δ=1.00 to 1.35, s, 18H δ=1.35 to 1.65, m, 11H δ=2.10 to 2.30, m, 1H δ=3.00 to 3.10, m, 1H δ=3.10 to 3.20, m, 1H δ=3.80, s, 2H δ=5.00, s, 1H δ=7.10 to 7.30, m, 8H

Synthesis Example 18

Synthesis of (Z)-((6R,7aR)-1,1-bis(4-t-butylphenyl)-3-oxohexahydropyrrolo[1,2-c]oxazol-6yl)N,N'-diisopropylcarbamimidate

[Chem. 58]

2000 mg (4.91 mmol) of (5R,7R)-[3,3,0]-1-aza-2-oxo-3-oxa-4,4-bis-(4'-t-butylphenyl)-7-hydroxybicyclooctane obtained in Synthesis Example 2, 10.0 ml of anhydrous DMF, 740 mg (5.86 mmol) of N,N'-diisopropylcarbodiimide, and 48.6 mg (0.49 mmol) of copper(I) chloride were put into a 50 ml capacity four neck flask, followed by stirring. After stirring at room temperature for 24 hours, the extraction was carried out by adding a saturated ammonium chloride aqueous solution and ethyl acetate to the reaction solution, and the organic layer was washed with a saturated ammonium chloride aqueous solution. After drying with anhydrous sodium sulfate, the solvent was evaporated, and then purified by a silica gel column chromatography, thereby obtaining 1.41 g of the product of interest with a yield of 53.8%.

Synthesis Example 19

Synthesis of (Z)-((3R,5R)-5-(bis(4-t-butylphenyl)methyl)pyrrolidine-3-yl)N,N'-diisopropylcarbamimidate (Synthesis of the Optically Active Cyclic Nitrogen-Containing Compound Used in Example 15)

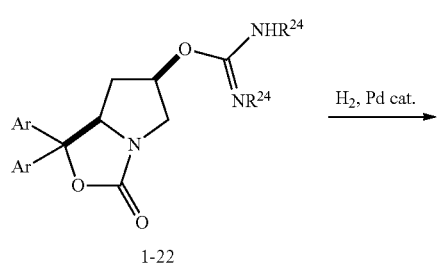

[Chem. 59]

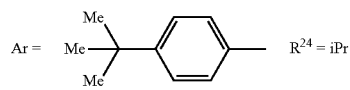

14.0 ml of methanol, 14.0 ml of THF and 140 mg of 10% by weight Pd/C were added to 1400 mg (2.62 mmol) of (Z)-((6R,7aR)-1,1-bis(4-t-butylphenyl)-3-oxohexahydropyrrolo[1,2-c]oxazol-6yl)N,N'-diisopropylcarbamimidate obtained in Synthesis Example 18, followed by stirring and carrying out hydrogen replacement. After carrying out 24 hours of the reaction at room temperature under a hydrogen atmosphere, Pd/C was removed by filtration and the filtrate was concentrated and purified by a alumina column chromatography, thereby obtaining 648 mg of the product of interest with a yield of 50.2%.

$^1$H-NMR (CD$_3$OD): δ=1.00 to 1.25, m, 30H δ=1.45 to 1.65, m, 2H δ=2.00 to 2.20, m, 1H δ=3.00 to 3.15, m, 3H δ=3.35, br, 1H δ=3.70 to 3.90, m, 2H δ=5.20, br, 1H δ=7.20 to 7.30, m, 8H

Synthesis Example 20

Synthesis of (2S,4S)-4-Hydoxyproline-N-ethyl carbamate methyl ester

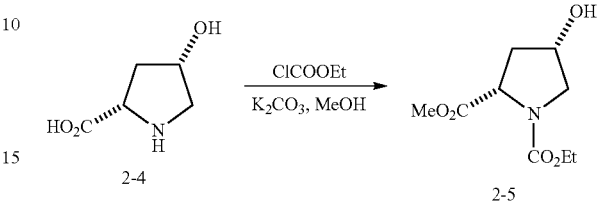

[Chem. 60]

This was carried out in accordance with the synthesis method of Tetrahedron, Vol. 49, No. 23, 5127-5132.

25.0 g (191 mmol) of (2S,4S)-hydroxyproline (manufactured by Watanabe Chemical Industries Ltd.), 150 ml of anhydrous methanol and 26.4 g (191 mmol) of potassium carbonate were put into a 300 ml capacity four neck flask, followed by stirring. Under ice-cooling, 40.2 ml (420 mmol) of ethyl chlorocarbonate was added dropwise thereto at 25° C. or less, followed by stirring at 0° C. for 24 hours. After filtering the reaction solution, methanol was evaporated, the residue was mixed with 150 ml of water and extracted with 150 ml of chloroform, and the water layer was further extracted twice with 150 ml of chloroform. The thus obtained organic layer was washed with saturated brine, dried with anhydrous magnesium sulfate and filtered, and then the solvent was evaporated to obtain 35.9 g of the product of interest with a yield of 86.7%.

Synthesis Example 21

Synthesis of (5S,7S)-[3,3,0]-1-aza-2-oxo-3-oxa-4,4-bis-(4'-t-butylphenyl)-7-hydroxybicyclooctane

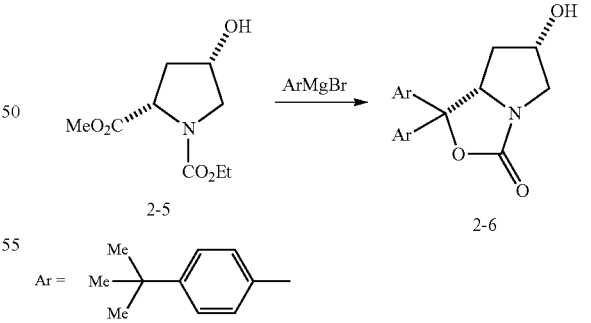

[Chem. 61]

This was carried out in accordance with the synthesis method of (S)-2-(diphenylmethyl)pyrrolidine described in Tetrahedron: Asymmetry, Vol. 8, No. 1, 149-153.

Under a stream of nitrogen, 2.41 g (99 mmol) of magnesium and 15 ml of anhydrous THF were put into a nitrogen-replaced 500 ml capacity reaction flask, followed by stirring. At room temperature, a 75 ml THF solution of 19.2 g (90 mmol) of 4-t-butylphenylbromobenzene was added dropwise thereto, followed by stirring at room temperature for 1 hour (synthesis of a Grignard compound).

Next, the above-mentioned solution was cooled to 5° C. or less, and a 125 ml THF solution of 6.10 g (30 mmol) of the (2S,4S)-4-Hydroxyproline-N-ethyl carbamate methyl ester obtained in Synthesis Example 20 was added dropwise thereto at 10° C. or less and allowed to undergo the reaction. Thereafter, this was heated under reflux for 3 hours and then cooled, and the reaction solution was added to 100 ml of saturated ammonium chloride aqueous solution. After recovering the THF, a concentrate was extracted twice with 200 ml of ethyl acetate, and the combined organic layers were washed twice with saturated brine. After drying the organic layer with anhydrous sodium sulfate, the solvent was evaporated, and the thus obtained concentrate was recrystallized from ethyl acetate/hexane to obtain 8.01 g of the product of interest.

Synthesis Example 22

Synthesis of (5S,7S)-[3,3,0]-1-aza-2-oxo-3-oxa-4,4-bis-(4'-t-butylphenyl)-7-(butylcarbamoyloxy)bicyclooctane

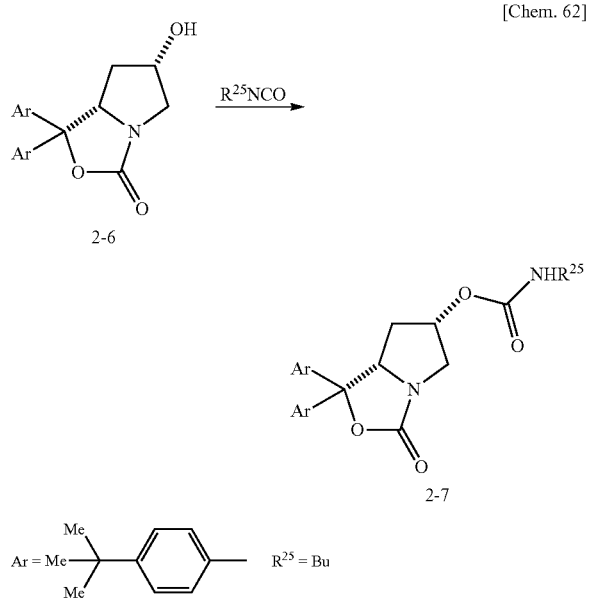

[Chem. 62]

900 mg (2.21 mmol) of (5S,7S)-[3,3,0]-1-aza-2-oxo-3-oxa-4,4-bis-(4'-t-butylphenyl)-7-hydroxybicyclooctane obtained in Synthesis Example 21, 9 ml of anhydrous DMF and 110 mg (1.11 mmol) of copper(I) chloride were put into a 50 ml capacity four neck flask, followed by stirring. At room temperature, 0.37 ml (3.32 mmol) of n-butylisocyanate was added dropwise thereto, followed by stirring at room temperature for 4 hours. After extraction by adding water and toluene to the reaction solution, the combined organic layers were washed with water and saturated brine. The solvent was evaporated, and then purified by a silica gel column chromatography, thereby obtaining 1.08 g of the colorless oily product of interest with a yield of 96.5%.

Synthesis Example 23

Synthesis of (2S,4S)-2-(bis-(4'-t-butylphenyl)methyl)-4-butylcarbamoyloxy)pyrrolidine Synthesis of the Optically Active Cyclic Nitrogen-Containing Compound Used in Examples 52

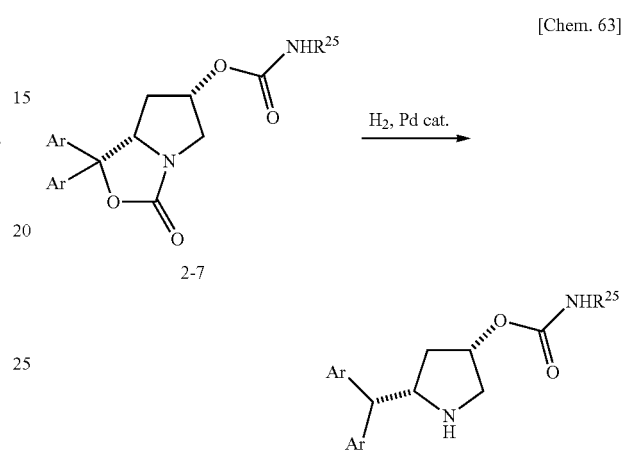

[Chem. 63]

10.8 ml of methanol, 10.8 ml of THF and 135 mg of 10% by weight Pd/C were added to 1.08 g (2.13 mmol) of (5S,7S)-[3,3,0]-1-aza-2-oxo-3-oxa-4,4-bis-(4'-t-butylphenyl)-7-(butylcarbamoyloxy)bicyclooctane obtained in Synthesis Example 22, followed by stirring and carrying out hydrogen replacement. After carrying out 3 days of the reaction at room temperature under a hydrogen atmosphere, Pd/C was removed by filtration and the filtrate was concentrated and purified by a silica gel column chromatography, thereby obtaining 755 mg of the colorless oily product of interest with a yield of 76.2%.

$^1$H-NMR (CD$_3$OD): δ=0.80 to 0.95, t, 3H δ=1.20 to 1.30, s, 18H δ=1.15 to 1.55, m, 6H δ=2.05 to 2.20, m, 1H δ=2.90 to 3.10, m, 4H δ=3.70 to 3.95, m, 2H δ=4.90 to 5.05, bs, 1H δ=7.10 to 7.35, m, 8H

Example 1

2 g (13.14 mmol) of citral, 25 mg of 5% by weight Pd/barium sulfate (1.25% by weight based on citral), 110 mg (0.24 mmol, 5.5% by weight based on citral) of (2R,4R)-2-(bis-(4'-t-butylphenyl)methyl)-4-(butylcarbamoyloxy)pyrrolidine, 27.0 mg (0.24 mmol) of trifluoroacetic acid (TFA) and 2 ml of 10% by weight hydrous t-butanol were put into a 50 ml capacity reaction flask, followed by stirring under an atmosphere of hydrogen. After stirring at 50° C. for 21 hours and subsequent removal of the catalyst by filtration, the resulting filtrate was analyzed by a gas chromatography to find that a conversion ratio of citral into citronellal was 78.0%, the thus obtained citronellal was d-form and its optical purity was 90.3% e.e. In this connection, a mixing ratio of geranial to neral of the used citral was 50:50.

Examples 2 to 5

Reactions were carried out in the same manner as in Example 1, except that the optically active cyclic nitrogen-containing compound were changed. In this connection, 110 mg of each optically active cyclic nitrogen-containing compound and the same amount (mol) of each acid based on the optically active cyclic nitrogen-containing compound were used. The results are shown in Table 3.

TABLE 3

| Example | Optically active cyclic nitrogen-containing compound represented by the general formula (1) | Acid | Conversion ratio (%) | Configuration of citronellal | Optical purity (% e.e.) |
|---|---|---|---|---|---|
| 1 | (structure with NHBu carbamate) | TFA | 78.0 | d | 90.3 |
| 2 | (structure with NHEt carbamate) | TFA | 98.8 | d | 89.8 |
| 3 | (structure with NHOct carbamate) | TFA | 86.9 | d | 90.2 |

TABLE 3-continued

| Example | Optically active cyclic nitrogen-containing compound represented by the general formula (1) | Acid | Conversion ratio (%) | Configuration of citronellal | Optical purity (% e.e.) |
|---|---|---|---|---|---|
| 4 | (structure: (2R,4R)-2-(bis-(4'-t-butylphenyl)methyl)-4-(diphenylcarbamoyloxy)pyrrolidine) | TFA | 80.3 | d | 89.4 |
| 5 | (structure: (2R,4R)-2-(diphenylmethyl)-4-(butylcarbamoyloxy)pyrrolidine) | TFA | 100 | d | 82.1 |

Example 6

2 g (13.14 mmol) of citral, 25 mg of 5% by weight Pd/barium sulfate (1.25% by weight based on citral), 110 mg (0.24 mmol, 5.5% by weight based on citral) of (2R,4R)-2-(bis-(4'-t-butylphenyl)methyl)-4-(butylcarbamoyloxy)pyrrolidine, 27.0 mg (0.24 mmol) of trifluoroacetic acid and 2 ml of 10% by weight hydrous t-butanol were put into a 50 ml capacity reaction flask, followed by stirring under an atmosphere of hydrogen. After stirring at 60° C. for 21 hours and subsequent removal of the catalyst by filtration, the resulting filtrate was analyzed by a gas chromatography to find that a conversion ratio of citral into citronellal was 100%, the thus obtained citronellal was d-form and its optical purity was 89.6% e.e. In this connection, a mixing ratio of geranial to neral of the used citral was 50:50.

Examples 7 to 11

Reactions were carried out in the same manner as in Example 6, except that the optically active cyclic nitrogen-containing compound were changed. In this connection, 110 mg of each optically active cyclic nitrogen-containing compound and the same amount (mol) of each acid based on the optically active cyclic nitrogen-containing compound were used. The results are shown in Table 4.

TABLE 4

| Example | Optically active cyclic nitrogen-containing compound represented by the general formula (1) | Acid | Conversion ratio (%) | Configuration of citronellal | Optical purity (% e.e.) |
|---|---|---|---|---|---|
| 6 | (structure: (2R,4R)-2-(bis-(4'-t-butylphenyl)methyl)-4-(butylcarbamoyloxy)pyrrolidine) | TFA | 100 | d | 89.6 |

TABLE 4-continued
| Example | Optically active cyclic nitrogen-containing compound represented by the general formula (1) | Acid | Conversion ratio (%) | Configuration of citronellal | Optical purity (% e.e.) |
|---|---|---|---|---|---|
| 7 | 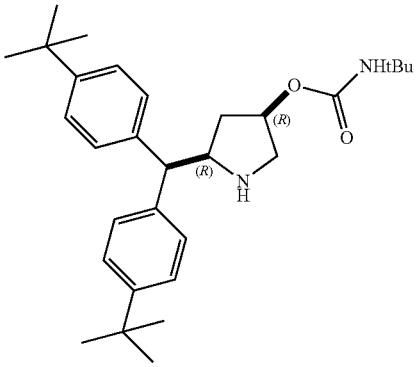 | TFA | 100 | d | 89.2 |
| 8 | 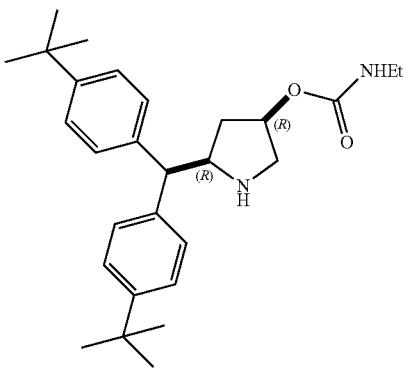 | TFA | 100 | d | 90.7 |
| 9 | 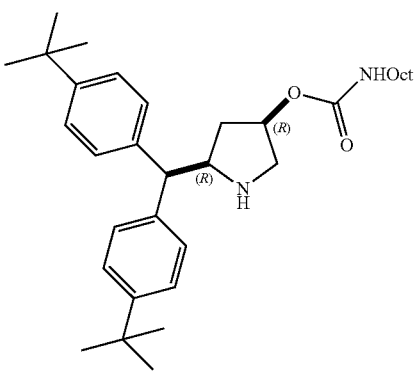 | TFA | 100 | d | 89.9 |
| 10 | 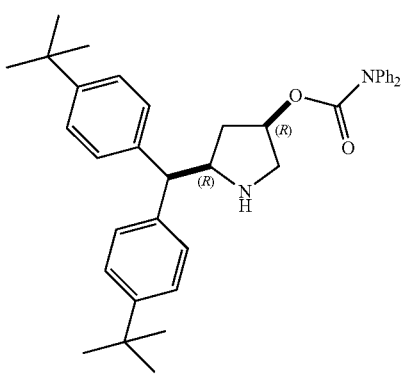 | TFA | 100 | d | 89.7 |

TABLE 4-continued

| Example | Optically active cyclic nitrogen-containing compound represented by the general formula (1) | Acid | Conversion ratio (%) | Configuration of citronellal | Optical purity (% e.e.) |
|---|---|---|---|---|---|
| 11 | (R)-2-(diphenylmethyl)-4-(butylcarbamoyloxy)pyrrolidine structure | TFA | 100 | d | 82.1 |

Example 12

2 g (13.14 mmol) of citral, 25 mg of 5% by weight Pd/barium sulfate (1.25% by weight based on citral), 50 mg (0.11 mmol, 2.5% by weight based on citral) of (2R,4R)-2-(bis-(4'-t-butylphenyl)methyl)-4-(butylcarbamoyloxy)pyrrolidine, 12.3 mg (0.11 mmol) of trifluoroacetic acid and 2 ml of 10% by weight hydrous t-butanol were put into a 50 ml capacity reaction flask, followed by stirring under an atmosphere of hydrogen. After stirring at 60° C. for 21 hours and subsequent removal of the catalyst by filtration, the resulting filtrate was analyzed by a gas chromatography to find that a conversion ratio of citral into citronellal was 98.9%, the thus obtained citronellal was d-form and its optical purity was 90.5% e.e. In this connection, a mixing ratio of geranial to neral of the used citral was 50:50.

Example 13

The reaction was carried out in the same manner as in Example 12, except that the optically active cyclic nitrogen-containing compound was changed. In this connection, 50 mg of the optically active cyclic nitrogen-containing compound and the same amount (mol) of acid based on the optically active cyclic nitrogen-containing compound were used. The results are shown in Table 5.

TABLE 5

| Example | Optically active cyclic nitrogen-containing compound represented by the general formula (1) | Acid | Conversion ratio (%) | Configuration of citronellal | Optical purity (% e.e.) |
|---|---|---|---|---|---|
| 12 | (2R,4R)-2-(bis-(4'-t-butylphenyl)methyl)-4-(butylcarbamoyloxy)pyrrolidine structure | TFA | 98.9 | d | 90.5 |
| 13 | (2R,4R)-2-(bis-(4'-t-butylphenyl)methyl)-4-(t-butylcarbamoyloxy)pyrrolidine structure | TFA | 96.1 | d | 88.4 |

Example 14

2 g (13.14 mmol) of citral, 25 mg of 5% by weight Pd/barium sulfate (1.25% by weight based on citral), 100 mg (0.21 mmol, 5.0% by weight based on citral) of (2R,4R)-2-(bis-(4'-t-butylphenyl)methyl)-4-(butylcarbamoyloxy)pyrrolidine, 24.5 mg (0.21 mmol) of trifluoroacetic acid and 2 ml of 10% by weight hydrous t-butanol were put into a 50 ml capacity reaction flask, followed by stirring under an atmosphere of hydrogen. After stirring at 60° C. for 21 hours and subsequent removal of the catalyst by filtration, the resulting filtrate was analyzed by a gas chromatography to find that a conversion ratio of citral into citronellal was 100%, the thus obtained citronellal was d-form and its optical purity was 91.1% e.e. In this connection, a mixing ratio of geranial to neral of the used citral was 50:50.

Example 15

The reaction was carried out in the same manner as in Example 14, except that the optically active cyclic nitrogen-containing compound was changed. In this connection, 100 mg of the optically active cyclic nitrogen-containing compound and the same amount (mol) of acid based on the optically active cyclic nitrogen-containing compound were used. The results are shown in Table 6.

Example 16

2 g (13.14 mmol) of citral, 20 mg of 5% by weight Pd/barium sulfate (1.0% by weight based on citral), 40 mg (0.09 mmol, 2.0% by weight based on citral) of (2R,4R)-2-(bis-(4'-t-butylphenyl)methyl)-4-(ethylcarbamoyloxy)pyrrolidine, 10.5 mg (0.09 mmol) of trifluoroacetic acid and 2 ml of 10% by weight hydrous t-butanol were put into a 50 ml capacity reaction flask, followed by stirring under an atmosphere of hydrogen. After stirring at 60° C. for 21 hours and subsequent removal of the catalyst by filtration, the resulting filtrate was analyzed by a gas chromatography to find that a conversion ratio of citral into citronellal was 97.1%, the thus obtained citronellal was d-form and its optical purity was 90.8% e.e. In this connection, a mixing ratio of geranial to neral of the used citral was 50:50.

Examples 17 to 24

Reactions were carried out in the same manner as in Example 16, except that the amount and type of acid added were changed. Further, the amount of acid used was determined based on the optically active cyclic nitrogen-containing compound. The results are shown in Table 7.

TABLE 6

| Example | Optically active cyclic nitrogen-containing compound represented by the general formula (1) | Acid | Conversion ratio (%) | Configuration of citronellal | Optical purity (% e.e.) |
|---|---|---|---|---|---|
| 14 | [structure] | TFA | 100 | d | 91.1 |
| 15 | [structure] | TFA | 86.4 | d | 80.9 |

TABLE 7

| Example | Acid | Amount of Acid (times by mol) | Conversion ratio (%) | Configuration of citronellal | Optical purity (% e.e.) |
|---|---|---|---|---|---|
| 16 | TFA | 1 | 97.1 | d | 90.8 |
| 17 | TFA | 2 | 100 | d | 90.9 |
| 18 | HCl | 1 | 70.5 | d | 90.9 |
| 19 | salicylic acid | 1 | 100 | d | 81.1 |
| 20 | salicylic acid | 2 | 100 | d | 86.5 |
| 21 | salicylic acid | 3 | 100 | d | 86.9 |
| 22 | DL-mandelic acid | 1 | 80.9 | d | 67.5 |
| 23 | DL-mandelic acid | 2 | 100 | d | 86.2 |
| 24 | DL-mandelic acid | 3 | 100 | d | 88.3 |

Example 25

2 g (13.14 mmol) of citral, 20 mg of 5% by weight Pd/barium sulfate (1.0% by weight based on citral), 40 mg (0.09 mmol, 2.0% by weight based on citral) of (2R,4R)-2-(bis-(4'-t-butylphenyl)methyl)-4-(ethylcarbamoyloxy)pyrrolidine, 13.6 mg (0.09 mmol) of L-tartaric acid and 2 ml of 10% by weight hydrous t-butanol were put into a 50 ml capacity reaction flask, followed by stirring under an atmosphere of hydrogen. After stirring at 60° C. for 5 hours and subsequent removal of the catalyst by filtration, the resulting filtrate was analyzed by a gas chromatography to find that a conversion ratio of citral into citronellal was 71.9%, the thus obtained citronellal was d-form and its optical purity was 75.9% e.e. In this connection, a mixing ratio of geranial to neral of the used citral was 50:50.

Examples 26 to 30

Reactions were carried out in the same manner as in Example 25, except that the amount and type of acid added were changed. Further, the amount of acid used was determined based on the optically active cyclic nitrogen-containing compound. The results are shown in Table 8.

TABLE 8

| Example | Acid | Amount of Acid (times by mol) | Conversion ratio (%) | Configuration of citronellal | Optical purity (% e.e.) |
|---|---|---|---|---|---|
| 25 | L-tartaric acid | 1 | 71.9 | d | 75.9 |
| 26 | L-tartaric acid | 2 | 100 | d | 85.9 |
| 27 | L-tartaric acid | 3 | 100 | d | 88.1 |
| 28 | citric acid | 1 | 79.2 | d | 77.7 |
| 29 | citric acid | 2 | 100 | d | 87.7 |
| 30 | citric acid | 3 | 100 | d | 88.9 |

Example 31

2 g (13.14 mmol) of citral, 20 mg of 5% by weight Pd/barium sulfate (1.0% by weight based on citral), 40 mg (0.09 mmol, 2.0% by weight based on citral) of (2R,4R)-2-(bis-(4'-t-butylphenyl)methyl)-4-(ethylcarbamoyloxy)pyrrolidine, 5.2 mg (0.05 mmol) of trifluoroacetic acid, 13.9 mg (0.09 mmol) of DL-mandelic acid and 2 ml of 10% by weight hydrous t-butanol were put into a 50 ml capacity reaction flask, followed by stirring under an atmosphere of hydrogen. After stirring at 60° C. for 21 hours and subsequent removal of the catalyst by filtration, the resulting filtrate was analyzed by a gas chromatography to find that a conversion ratio of citral into citronellal was 100%, the thus obtained citronellal was d-form and its optical purity was 89.0% e.e. In this connection, a mixing ratio of geranial to neral of the used citral was 50:50.

Examples 32 to 33

Reactions were carried out in the same manner as in Example 31, except that the amount of DL-mandelic acid added was changed. Further, the amount of DL-mandelic acid used was determined based on the optically active cyclic nitrogen-containing compound. The results are shown in Table 9.

TABLE 9

| Example | Amount of DL-mandelic acid (times by mol) | Conversion ratio (%) | Configuration of citronellal | Optical purity (% e.e.) |
|---|---|---|---|---|
| 31 | 1 | 100 | d | 89.0 |
| 32 | 2 | 100 | d | 89.8 |
| 33 | 3 | 100 | d | 89.8 |

Example 34

2 g (13.14 mmol) of citral, 20 mg of 5% by weight Pd/barium sulfate (1.0% by weight based on citral), 40 mg (0.09 mmol, 2.0% by weight based on citral) of (2R,4R)-2-(bis-(4'-t-butylphenyl)methyl)-4-(ethylcarbamoyloxy)pyrrolidine, 5.2 mg (0.05 mmol) of trifluoroacetic acid, 17.6 mg (0.09 mmol) of citric acid and 2 ml of 10% by weight hydrous t-butanol were put into a 50 ml capacity reaction flask, followed by stirring under an atmosphere of hydrogen. After stirring at 60° C. for 5 hours and subsequent removal of the catalyst by filtration, the resulting filtrate was analyzed by a gas chromatography to find that a conversion ratio of citral into citronellal was 89.5%, the thus obtained citronellal was d-form and its optical purity was 86.7% e.e. In this connection, a mixing ratio of geranial to neral of the used citral was 50:50.

Examples 35 and 36

Reactions were carried out in the same manner as in Example 34, except that the amount of citric acid added was changed. Further, the amount of citric acid used was determined based on the optically active cyclic nitrogen-containing compound. The results are shown in Table 10.

TABLE 10

| Example | Amount of citric acid (times by mol) | Conversion ratio (%) | Configuration of citronellal | Optical purity (% e.e.) |
|---|---|---|---|---|
| 34 | 1 | 89.5 | d | 86.7 |
| 35 | 2 | 100 | d | 88.9 |
| 36 | 3 | 100 | d | 88.9 |

Example 37

2 g (13.14 mmol) of citral, 20 mg of 5% by weight Pd/barium sulfate (1.0% by weight based on citral), 40 mg (0.09 mmol, 2.0% by weight based on citral) of (2R,4R)-2-(bis-(4'-t-butylphenyl)methyl)-4-(ethylcarbamoyloxy)pyrrolidine, 1.7 mg (0.05 mmol) of hydrochloric acid, 13.9 mg (0.09 mmol) of DL-mandelic acid and 2 ml of 10% by weight hydrous t-butanol were put into a 50 ml capacity reaction flask, followed by stirring under an atmosphere of hydrogen. After stirring at 60° C. for 21 hours and subsequent removal of the catalyst by filtration, the resulting filtrate was analyzed by a gas chromatography to find that a conversion ratio of citral into citronellal was 92.5%, the thus obtained citronellal was d-form and its optical purity was 88.8% e.e. Further, a mixing ratio of geranial to neral of the used citral was 50:50.

Examples 38 and 39

Reactions were carried out in the same manner as in Example 37, except that the amount of DL-mandelic acid added was changed. Further, the amount of DL-mandelic acid used was determined based on the optically active cyclic nitrogen-containing compound. The results are shown in Table 11.

TABLE 11

| Example | Amount of DL-mandelic acid (times by mol) | Conversion ratio (%) | Configuration of citronellal | Optical purity (% e.e.) |
|---|---|---|---|---|
| 37 | 1 | 92.5 | d | 88.8 |
| 38 | 2 | 100 | d | 91.6 |
| 39 | 3 | 100 | d | 91.2 |

Example 40

2 g (13.14 mmol) of citral, 20 mg of 5% by weight Pd/barium sulfate (1.0% by weight based on citral), 40 mg (0.09 mmol, 2.0% by weight based on citral) of (2R,4R)-2-(bis-(4'-t-butylphenyl)methyl)-4-(ethylcarbamoyloxy)pyrrolidine, 1.7 mg (0.05 mmol) of hydrochloric acid, 17.6 mg (0.09 mmol) of citric acid and 2 ml of 10% by weight hydrous t-butanol were put into a 50 ml capacity reaction flask, followed by stirring under an atmosphere of hydrogen. After stirring at 60° C. for 5 hours and subsequent removal of the catalyst by filtration, the resulting filtrate was analyzed by a gas chromatography to find that a conversion ratio of citral into citronellal was 98.9%, the thus obtained citronellal was d-form and its optical purity was 85.3% e.e. In this connection, a mixing ratio of geranial to neral of the used citral was 50:50.

Examples 41 and 42

Reactions were carried out in the same manner as in Example 40, except that the amount of citric acid added was changed. Further, the amount of citric acid used was determined based on the optically active cyclic nitrogen-containing compound. The results are shown in Table 12.

TABLE 12

| Example | Amount of citric acid (times by mol) | Conversion ratio (%) | Configuration of citronellal | Optical purity (% e.e.) |
|---|---|---|---|---|
| 40 | 1 | 98.9 | d | 85.3 |
| 41 | 2 | 100 | d | 88.4 |
| 42 | 3 | 94.5 | d | 89.8 |

Example 43

2 g (13.14 mmol) of citral, 20 mg of 5% by weight Pd/barium sulfate (1.0% by weight based on citral), 40 mg (0.09 mmol, 2.0% by weight based on citral) of (2R,4R)-2-(bis-(4'-t-butylphenyl)methyl)-4-(ethylcarbamoyloxy)pyrrolidine, 1.7 mg (0.05 mmol) of hydrochloric acid, 13.8 mg (0.09 mmol) of L-tartaric acid and 2 ml of 10% by weight hydrous t-butanol were put into a 50 ml capacity reaction flask, followed by stirring under an atmosphere of hydrogen. After stirring at 60° C. for 5 hours and subsequent removal of the catalyst by filtration, the resulting filtrate was analyzed by a gas chromatography to find that a conversion ratio of citral into citronellal was 76.0%, the thus obtained citronellal was d-form and its optical purity was 88.5% e.e. In this connection, a mixing ratio of geranial to neral of the used citral was 50:50.

Examples 44 and 45

Reactions were carried out in the same manner as in Example 43, except that the amount of L-tartaric acid added was changed. Further, the amount of L-tartaric acid used was determined based on the optically active cyclic nitrogen-containing compound. The results are shown in Table 13.

TABLE 13

| Example | Amount of L-tartaric acid (times by mol) | Conversion ratio (%) | Configuration of citronellal | Optical purity (% e.e.) |
|---|---|---|---|---|
| 43 | 1 | 76.0 | d | 88.5 |
| 44 | 2 | 86.4 | d | 89.2 |
| 45 | 3 | 80.8 | d | 89.7 |

Example 46

2 g (13.14 mmol) of citral, 20 mg of 5% by weight Pd/barium sulfate (1.0% by weight based on citral), 20 mg (0.05 mmol, 1.0% by weight based on citral) of (2R,4R)-2-(bis-(4'-t-butylphenyl)methyl)-4-(ethylcarbamoyloxy)pyrrolidine, 3.3 mg (0.09 mmol) of hydrochloric acid, 8.8 mg (0.05 mmol) of citric acid and 2 ml of 10% by weight hydrous t-butanol were put into a 50 ml capacity reaction flask, followed by stirring under an atmosphere of hydrogen. After stirring at 60° C. for 21 hours and subsequent removal of the catalyst by filtration, the resulting filtrate was analyzed by a gas chromatography to find that a conversion ratio of citral into citronellal was 88.0%, the thus obtained citronellal was d-form and its optical purity was 86.3% e.e. In this connection, a mixing ratio of geranial to neral of the used citral was 50:50.

Examples 47 and 48

Reactions were carried out in the same manner as in Example 46, except that the amount of citric acid added was changed. Further, the amount of citric acid used was determined based on the optically active cyclic nitrogen-containing compound. The results are shown in Table 14.

TABLE 14

| Example | Amount of citric acid (times by mol) | Conversion ratio (%) | Configuration of citronellal | Optical purity (% e.e.) |
|---|---|---|---|---|
| 46 | 1 | 88.0 | d | 86.3 |
| 47 | 2 | 100 | d | 88.7 |
| 48 | 3 | 100 | d | 87.6 |

Example 49

2 g (13.14 mmol) of citral, 20 mg of 5% by weight Pd/barium sulfate (1.0% by weight based on citral), 20 mg (0.05 mmol, 1.0% by weight based on citral) of (2R,4R)-2-(bis-(4'-t-butylphenyl)methyl)-4-(ethylcarbamoyloxy)pyrrolidine, 3.3 mg (0.09 mmol) of hydrochloric acid, 6.9 mg (0.05 mmol) of L-tartaric acid and 2 ml of 10% by weight hydrous t-butanol were put into a 50 ml capacity reaction flask, followed by stirring under an atmosphere of hydrogen. After stirring at 60° C. for 21 hours and subsequent removal of the catalyst by filtration, the resulting filtrate was analyzed by a gas chromatography to find that a conversion ratio of citral into citronellal was 98.5%, the thus obtained citronellal was d-form and its optical purity was 89.2% e.e. In this connection, a mixing ratio of geranial to neral of the used citral was 50:50.

Examples 50 and 51

Reactions were carried out in the same manner as in Example 49, except that the amount of L-tartaric acid added was changed. Further, the amount of L-tartaric acid used was determined based on the optically active cyclic nitrogen-containing compound. The results are shown in Table 15.

TABLE 15

| Example | Amount of L-tartaric acid (times by mol) | Conversion ratio (%) | Configuration of citronellal | Optical purity (% e.e.) |
|---|---|---|---|---|
| 49 | 1 | 98.5 | d | 89.2 |
| 50 | 2 | 100 | d | 89.0 |
| 51 | 3 | 100 | d | 89.6 |

Example 52

2 g (13.14 mmol) of citral, 25 mg of 5% by weight Pd/barium sulfate (1.25% by weight based on citral), 110 mg (0.24 mmol, 5.5% by weight based on citral) of (2S,4S)-2-(bis-(4'-t-butylphenyl)methyl)-4-(butylcarbamoyloxy)pyrrolidine, 27.0 mg (0.24 mmol) of trifluoroacetic acid and 2 ml of 10% by weight hydrous t-butanol were put into a 50 ml capacity reaction flask, followed by stirring under an atmosphere of hydrogen. After stirring at 50° C. for 21 hours and subsequent removal of the catalyst by filtration, the resulting filtrate was analyzed by a gas chromatography to find that a conversion ratio of citral into citronellal was 85.8%, the thus obtained citronellal was l-form and its optical purity was 91.1% e.e. In this connection, a mixing ratio of geranial to neral of the used citral was 50:50.

While the invention has been described in detail and with reference to specific embodiments thereof, it will be apparent to one skilled in the art that various changes and modifications can be made therein without departing from the spirit and scope thereof.

This application is based on Japanese Patent Application No. 2010-265556 filed on Nov. 29, 2010, and the entire subject matter of which is incorporated herein by reference.

INDUSTRIAL APPLICABILITY

The catalyst for asymmetric hydrogenation to be used in the invention, which is prepared by simply mixing a metal powder or metal-supported substance, an optically active cyclic nitrogen-containing compound and an acid, can produce an optically active α,β-carbonyl compound by conveniently carrying out asymmetric hydrogenation of its substrate, i.e. an α,β-unsaturated carbonyl compound.

That is, optically active citronellal can be obtained by conducting selective asymmetric hydrogenation of α,β-carbon-carbon double bond of citral (a mixture of geranial and neral), geranial or neral. The optically active citronellal is not only useful by itself as a flavor or fragrance but is also an important raw material of optically active citronellol, optically active isopulegol and optically active menthol.

According to the invention, even when a mixture (so-called citral) of the Z-configuration compound and E-configuration compound is used as the substrate, there is no need to carry out the asymmetric hydrogenation after distilling citral to obtain high purity neral or geranial. Accordingly, an optically active carbonyl compound having the same configuration can be produced.

In addition, since the catalyst of the invention is not soluble in the reaction solution, the metal or metal-supported substance and optically active cyclic nitrogen-containing compound can be easily recovered and recycled, which is industrially advantageous.

The invention claimed is:
1. A catalyst, which comprises:
(1) a powder of at least one metal selected from metals belonging to Group 8 to Group 10 of the Periodic Table, or at least one supported metal selected from metals belonging to Group 8 to Group 10 of the Periodic Table;
(2) an optically active compound represented by formula (1):

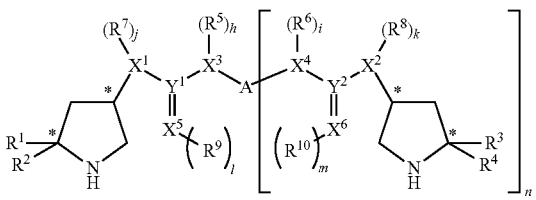

(1)

wherein $R^1$, $R^2$, $R^3$, $R^4$, $R^5$, $R^6$, $R^7$, $R^8$, $R^9$ and $R^{10}$ each independently represent a hydrogen atom, an alkyl group which can have a substituent group, a cycloalkyl group which can have a substituent group, an alkenyl group which can have a substituent group, an aryl group which can have a substituent group, an aralkyl group which can have a substituent group, an alkoxy group which can have a substituent group, an alkoxycarbonyl group which can have a substituent group, a siloxy group which can have a substituent group, an aromatic heterocyclic group which can have a substituent group or an aliphatic heterocyclic group which can have a substituent group, wherein $R^1$ and $R^2$ are different from each other, and $R^3$ and $R^4$ are different from each other, h, i, j, k, l and m represents an integer of 0 or 1, n represents an integer of 0 to 3, and * represents an asymmetric carbon atom, A represents, when n=0, a hydrogen atom, a hetero atom which can have a substituent group, an alkyl group which can have a substituent group, a cycloalkyl group which can have a substituent group, an alkenyl group which can have a substituent group, an aryl group which can have a substituent group, an aralkyl group which can have a substituent group, an alkoxy group which can have a substituent group, a carboxyl group which can have a substituent group, an alkoxycarbonyl group which can have a substituent group, an amido group which can have a substituent group, an aromatic heterocyclic group which can have a substituent group, an aliphatic heterocyclic group which can have a substituent group, an oligomer chain, or a polymer chain, and A represents, when n=1 to 3, a hetero atom which can have a substituent group, an alkylene group which can have a substituent group, an alkylene group which includes an arylene group and can have a substituent group, an alkylene group which includes a cycloalkylene group and can have a substituent group, an alkylene group which includes a hetero atom and can have a substituent group, a divalent aliphatic hydrocarbon cyclic group which can have a substituent group, a divalent aliphatic heterocyclic group which can have a substituent group, a divalent aromatic hydrocarbon cyclic group which can have a substituent group, a divalent aromatic heterocyclic group which can have a substituent group, an oligomer chain, or a polymer chain, $R^5$ and $R^6$, $R^5$ and A, or $R^6$ and A may form a ring, $X^1$, $X^2$, $X^3$, $X^4$, $X^5$ and $X^6$ each independently represent an oxygen atom, a nitrogen atom, a phosphorus atom or a sulfur atom, and $Y^1$ and $Y^2$ each independently represent a carbon atom, a silicon atom or a sulfur atom; and (3) an acid.

2. The catalyst for asymmetric hydrogenation according to claim 1, wherein the metal is selected from the group consisting of nickel, ruthenium, rhodium, iridium, palladium and platinum.

3. A method for manufacturing an optically active carbonyl compound represented by formula (3):

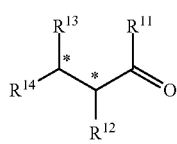

(3)

wherein $R^{11}$, $R^{12}$, $R^{13}$ and $R^{14}$ are the same as defined in formula (2), and two * mean that at least one * represents an asymmetric carbon atom, wherein the method comprises conducting asymmetric hydrogenation of an α, β-unsaturated carbonyl compound represented by formula (2) by using the catalyst for asymmetric hydrogenation according to claim 1 or 2:

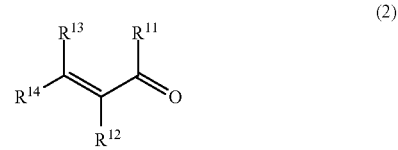

(2)

wherein $R^{11}$, $R^{12}$, $R^{13}$ and $R^{14}$ each independently represent a hydrogen atom, an alkyl group which can have a substituent group, a cycloalkyl group which can have a substituent group, an alkenyl group which can have a substituent group, an aryl group which can have a substituent group, an aromatic heterocyclic group which can have a substituent group, an aliphatic heterocyclic group which can have a substituent group, an acyl group which can have a substituent group, an alkoxycarbonyl group which can have a substituent group, or an aralkyloxy group which can have a substituent group; $R^{11}$ and $R^{12}$, $R^{11}$ and $R^{13}$, $R^{11}$ and $R^{14}$, $R^{12}$ and $R^{14}$, or $R^{13}$ and $R^{14}$ may form a ring; when a ring is not formed by $R^{11}$ and $R^{12}$ or $R^{11}$ and $R^{13}$, and $R^{12}$ does not represent a hydrogen atom, $R^{13}$ and $R^{14}$ may be the same or different from each other; and when a ring is not formed by $R^{11}$ and $R^{12}$ or $R^{11}$ and $R^{13}$, and $R^{12}$ represents a hydrogen atom, $R^{13}$ and $R^{14}$ do not represent a hydrogen atom and are different from each other.

4. The method according to claim 3, wherein the α, β-unsaturated carbonyl compound is geranial, neral or a mixture thereof comprising citral.

5. The method according to claim 3, wherein the α, β-unsaturated carbonyl compound is an α, β-unsaturated ketone having from 5 to 18 carbon atoms.

6. The catalyst for asymmetric hydrogenation according to claim 1, wherein the support for the metal or metals is selected from the group consisting of carbon, silica, alumina, silica-alumina, zeolite, a metal oxide, a metal halide, a metal sulfide, a metal sulfonate, a metal nitrate, a metal carbonate and a metal phosphate.

* * * * *